(12) United States Patent
Kobayashi

(10) Patent No.: US 9,404,040 B2
(45) Date of Patent: Aug. 2, 2016

(54) LIQUID CRYSTAL COMPOUND HAVING FLUORINE-CONTAINING ALKENYL TERMINAL GROUP, LIQUID CRYSTAL COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventor: Masahide Kobayashi, Ichihara (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

(21) Appl. No.: 14/544,778

(22) Filed: Feb. 18, 2015

(65) Prior Publication Data

US 2015/0232759 A1    Aug. 20, 2015

(30) Foreign Application Priority Data

Feb. 18, 2014    (JP) .................................. 2014-28524

(51) Int. Cl.

| | | |
|---|---|---|
| G02F 1/1333 | (2006.01) | |
| C09K 19/34 | (2006.01) | |
| C09K 19/30 | (2006.01) | |
| C07D 309/06 | (2006.01) | |
| C07D 309/04 | (2006.01) | |
| C07C 25/24 | (2006.01) | |
| C07D 309/08 | (2006.01) | |
| C09K 19/04 | (2006.01) | |
| C09K 19/12 | (2006.01) | |
| C09K 19/20 | (2006.01) | |

(52) U.S. Cl.
CPC ............. *C09K 19/3402* (2013.01); *C07C 25/24* (2013.01); *C07D 309/04* (2013.01); *C07D 309/06* (2013.01); *C07D 309/08* (2013.01); *C09K 19/3003* (2013.01); *C09K 19/3028* (2013.01); *C09K 19/3066* (2013.01); *C09K 19/3068* (2013.01); *C09K 2019/0444* (2013.01); *C09K 2019/122* (2013.01); *C09K 2019/123* (2013.01); *C09K 2019/2064* (2013.01); *C09K 2019/301* (2013.01); *C09K 2019/3004* (2013.01); *C09K 2019/3009* (2013.01); *C09K 2019/3036* (2013.01); *C09K 2019/3078* (2013.01); *C09K 2019/3422* (2013.01); *C09K 2019/3425* (2013.01)

(58) Field of Classification Search
CPC ........... C09K 19/3402; C09K 19/3003; C09K 19/3068; C09K 19/3028; C09K 19/3066; C09K 2019/3004; C09K 2019/3009; C09K 2019/301; C09K 2019/3078; C09K 2019/3036; C09K 2019/3422; C09K 2019/0444; C09K 2019/122; C09K 2019/123; C09K 2019/3425; C09K 2019/2064; C07D 309/06; C07D 309/04; C07D 309/08; C07C 25/24
USPC ............... 252/299.01, 299.6, 299.61, 299.63, 252/299.66; 428/1.1
See application file for complete search history.

(56) References Cited

U.S. PATENT DOCUMENTS 7,081,279 B2 * 7/2006 Kato .................... C07C 17/2635
                                                    252/299.61
2011/0291047 A1   12/2011 Yano

FOREIGN PATENT DOCUMENTS

| EP | 0969071 A1 | 1/2000 |
|---|---|---|
| JP | 2002193852 A | 7/2002 |
| JP | 2009149667 A | 7/2009 |
| JP | 2011246411 A | 12/2011 |

* cited by examiner

*Primary Examiner* — Geraldina Visconti
(74) *Attorney, Agent, or Firm* — Hogan Lovells US LLP

(57) ABSTRACT

To provide a liquid crystal compound satisfying at least one of high stability to heat, light and so forth, a high clearing point, a low minimum temperature of a liquid crystal phase, small viscosity, suitable optical anisotropy, large dielectric anisotropy, a suitable elastic constant and excellent compatibility with other liquid crystal compounds, a liquid crystal composition containing the compound, and a liquid crystal display device including the composition.

The compound is represented by formula (1):

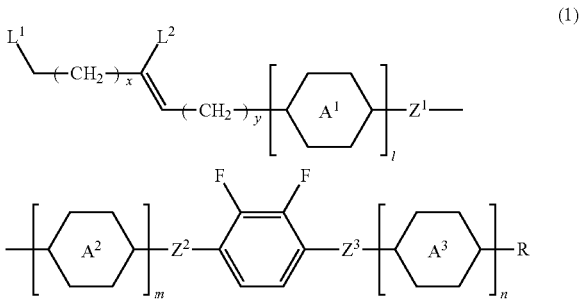

wherein, for example, R is alkyl having 1 to 10 carbons or alkoxy having 1 to 9 carbons; ring $A^1$, ring $A^2$ and ring $A^3$ is 1,4-cyclohexylene, 1,4-phenylene or 2,3-difluoro-1,4-phenylene; at least one of $L^1$ and $L^2$ is fluorine and the remainder is hydrogen; $Z^1$, $Z^2$ and $Z^3$ are a single bond, $-(CH_2)_2-$, $-CH_2O-$ or $-COO-$; x and y are an integer from 0 to 10; and l, m and n are 0 or 1.

19 Claims, No Drawings

LIQUID CRYSTAL COMPOUND HAVING FLUORINE-CONTAINING ALKENYL TERMINAL GROUP, LIQUID CRYSTAL COMPOSITION AND LIQUID CRYSTAL DISPLAY DEVICE

TECHNICAL FIELD

The invention relates to a liquid crystal compound, a liquid crystal composition and a liquid crystal display device. More specifically, the invention relates to a compound that has a fluorine-containing alkenyl terminal group and 2,3-difluoro-1,4-phenylene, and has a negative dielectric anisotropy, a liquid crystal composition containing the compound, and a liquid crystal display device including the composition.

BACKGROUND ART

A liquid crystal display device is widely utilized for a display of a personal computer, a television and so forth. The device utilizes optical anisotropy, dielectric anisotropy or the like of a liquid crystal compound. As an operating mode of the liquid crystal display device, various modes are known, such as a phase change (PC) mode, a twisted nematic (TN) mode, a super twisted nematic (STN) mode, a bistable twisted nematic (BTN) mode, an electrically controlled birefringence (ECB) mode, an optically compensated bend (OCB) mode, an in-plane switching (IPS) mode, a vertical alignment (VA) mode, a fringe field switching (FFS) mode and a polymer sustained alignment (PSA) mode.

Among the modes, the IPS mode, the FFS mode and the VA mode are known to improve narrowness of a viewing angle being a disadvantage of the operating mode such as the TN mode and the STN mode. In the liquid crystal display device having the mode of the kind, a liquid crystal composition having a negative dielectric anisotropy is mainly used. In order to further improve characteristics of the liquid crystal display device, the liquid crystal compound contained in the composition preferably has physical properties described in (1) to (8) below:
(1) high stability to heat, light and so forth;
(2) high clearing point;
(3) low minimum temperature of a liquid crystal phase;
(4) small viscosity ($\eta$);
(5) suitable optical anisotropy ($\Delta n$);
(6) large negative dielectric anisotropy ($\Delta\epsilon$);
(7) suitable elastic constant ($K_{33}$: bend elastic constant); and
(8) excellent compatibility with other liquid crystal compounds.

An effect of the physical properties of the liquid crystal compound on the characteristics of the device is as described below. A compound having a high stability to heat, light and so forth as described in (1) increases a voltage holding ratio of the device. Thus, a service life of the device becomes long. A compound having a high clearing point as described in (2) extends a temperature range in which the device can be used. A compound having a low minimum temperature of the liquid crystal phase such as a nematic phase and a smectic phase, as described in (3), particularly, a compound having a low minimum temperature of the nematic phase also extends a temperature range in which the device can be used. A compound having a small viscosity as described in (4) shortens a response time of the device.

A compound having a suitable optical anisotropy as described in (5) improves a contrast of the device. According to a design of the device, a compound having a large optical anisotropy or a small optical anisotropy, mare specifically, a compound having a suitable optical anisotropy is required. When the response time is shortened by decreasing a cell gap of the device, a compound having a large optical anisotropy is suitable. A compound having a large negative dielectric anisotropy as described in (6) decreases a threshold voltage of the device. Thus, an electric power consumption of the device becomes small.

With regard to (7), a compound having a large elastic constant shortens the response time of the device. A compound having a small elastic constant decreases the threshold voltage of the device. Accordingly, a suitable elastic constant is required according to characteristics to be desirably improved. A compound having an excellent compatibility with other liquid crystal compounds as described in (8) is preferred. The reason is that physical properties of the composition are adjusted by mixing liquid crystal compounds having different physical properties.

Various kinds of liquid crystal compounds having a negative dielectric anisotropy have been synthesized so far (Patent literature Nos. 1 to 2, for example). Patent literature No. 1 discloses compound (A) and compound (B). Patent literature No. 2 discloses compound (C). Patent literature No. 3 discloses compound (D). However, the compounds are far from being fully suitable for a mode of a liquid crystal display device in recent years.

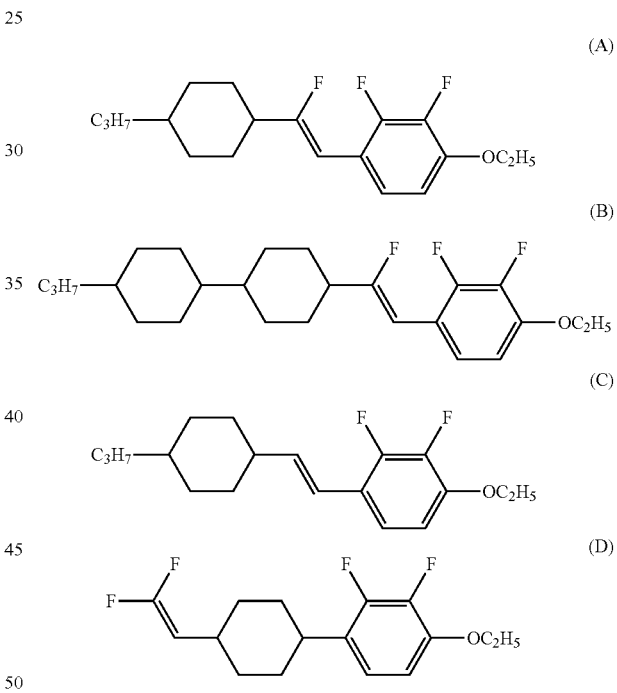

A new compound can be expected to have excellent physical properties that are not found in a conventional compound. The new compound is expected to have a suitable balance regarding two of physical properties required upon preparing the liquid crystal composition. In view of such a situation, development has been desired for a compound having excellent physical properties and a suitable balance regarding the physical properties with regard to (1) to (8) as described above.

CITATION LIST

Patent Literature

Patent literature No. 1: JP 2011-246411 A.
Patent literature No. 2: JP 2002-193852 A.
Patent literature No. 3: JP 2009-149667 A.

SUMMARY OF INVENTION

Technical Problem

A first object of the invention is to provide a liquid crystal compound having a high stability to heat, light and so forth, a high clearing point, a low minimum temperature of a liquid crystal phase, a small viscosity, a suitable optical anisotropy, a large negative dielectric anisotropy, a suitable elastic constant and an excellent compatibility with other liquid crystal compounds. The object is to provide a compound having a particularly large negative dielectric anisotropy. The object is to provide a compound having a particularly excellent compatibility. A second object is to provide a liquid crystal composition that contains the compound and has a high maximum temperature of a nematic phase, a low minimum temperature of the nematic phase, a small viscosity, a suitable optical anisotropy, the large negative dielectric anisotropy and a suitable elastic constant. The object is to provide a liquid crystal composition having a suitable balance regarding at least two of the physical properties. A third object is to provide a liquid crystal display device that includes the composition and has a wide temperature range in which the device can be used, a short response time, a large voltage holding ratio, a low threshold voltage, a large contrast ratio and a long service life.

The invention concerns a compound represented by formula (1), a liquid crystal composition containing the compound, and a liquid crystal display device including the composition:

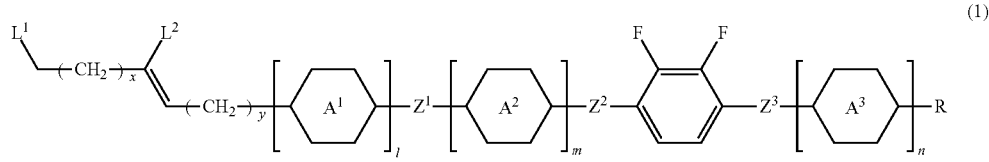

$$(1)$$

wherein, in formula (1),

R is hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;

ring $A^1$, ring $A^2$ and ring $A^3$ are independently 1,4-cyclohexylene, 1,4-cyclohexenylene, tetrahydropyran-2,5-diyl, 1,3-dioxane-2,5-diyl, pyrimidine-2,5-diyl, pyridine-2,5-diyl, naphthalene-2,6-diyl, decahydronaphthalene-2,6-diyl, 1,2,3,4-tetrahydronaphthalene-2,6-diyl, 1,4-phenylene, 2-fluoro-1,4-phenylene or 2,3-difluoro-1,4-phenylene;

$L^1$ and $L^2$ are independently hydrogen, fluorine or chlorine, and at least one of $L^1$ and the $L^2$ is fluorine;

$Z^1$, $Z^2$, and $Z^3$ are independently a single bond, —$(CH_2)_2$—, —$CH_2O$—, —$OCH_2$—, —COO—, —OCO—, —$CF_2O$— or —$OCF_2$—;

x and y are independently an integer from 0 to 10; and l, m and n are 0, 1 or 2, and a sum of l, m and n is 1, 2 or 3.

The invention also concerns use of at least one compound as a component of a liquid crystal composition.

Advantageous Effects of Invention

A first advantage of the invention is to provide a liquid crystal compound having a high stability to heat, light and so forth, a high clearing point, a low minimum temperature of a liquid crystal phase, a small viscosity, a suitable optical anisotropy, the large negative dielectric anisotropy, a suitable elastic constant and an excellent compatibility with other liquid crystal compounds. The advantage is to provide a compound having a particularly large negative dielectric anisotropy. The advantage is to provide a compound having a particularly excellent compatibility. A second advantage is to provide a liquid crystal composition that contains the compound and has a high maximum temperature of a nematic phase, a low minimum temperature of the nematic phase, a small viscosity, a suitable optical anisotropy, a large negative dielectric anisotropy and a suitable elastic constant. The advantage is a liquid crystal composition having a suitable balance regarding at least two of physical properties. A third advantage is to provide a liquid crystal display device that includes the composition and has a wide temperature range in which the device can be used, a short response time, a large voltage holding ratio, a low threshold voltage, a large contrast ratio and a long service life.

DESCRIPTION OF EMBODIMENTS

Usage of terms herein is as described below. A liquid crystal compound is a generic term for a compound having a liquid crystal phase such as a nematic phase or a smectic phase, and also a compound having no liquid crystal phase but being useful as a component of the liquid crystal composition. The liquid crystal compound, the liquid crystal composition and a liquid crystal display device may be occasionally abbreviated as "compound," "composition" and "device," respectively. The liquid crystal display device is a generic term for a liquid crystal display panel and a liquid crystal display module. A clearing point is a transition temperature between the liquid crystal phase and an isotropic phase in the liquid crystal compound. A minimum temperature of the liquid crystal phase is a transition temperature between a solid and the liquid crystal phase (the smectic phase, the nematic phase or the like) in the liquid crystal compound. A maximum temperature of the nematic phase is a transition temperature between the nematic phase and the isotropic phase in the liquid crystal composition, and may be occasionally abbreviated as the maximum temperature. The minimum temperature of the nematic phase may be occasionally abbreviated as the minimum temperature. "Compound represented by formula (1)" may be occasionally abbreviated as "compound (1)." The abbreviation may be occasionally applied also to a compound represented by formula (2) or the like. In formula (1), formula (2) or the like, a symbol such as $A^1$ and $D^1$ surrounded by a hexagonal shape corresponds to ring $A^1$, ring $D^1$ or the like, respectively. A plurality of ring $A^1$ are described in one formula or in different formulas. In the compounds, two groups represented by two of arbitrary ring $A^1$ may be identical or different. The rule is also applied to a symbol such as ring $A^2$ and $Z^2$. Moreover, the rule is also applied to two of ring $A^1$ when l is 2. An amount of the compound expressed in terms of "percent" is expressed in terms of "weight percent (% by weight)" based on the total amount of the composition.

An expression "at least one of "A" may be replaced by "B"" means that a position of "A" is arbitrary when the number of "A" is 1, and also when the number of "A" is 2 or more, positions thereof can be selected without limitation. An expression "at least one of A may be replaced by B, C or D" means a case where arbitrary A is replaced by B, a case where arbitrary A is replaced by C, a case where arbitrary A is replaced by D, and further a case where a plurality of A are replaced by at least two of B, C and D. For example, alkyl in which at least one of —$CH_2$— may be replaced by —O— or —CH=CH— includes alkyl, alkenyl, alkoxy, alkoxyalkyl, alkoxyalkenyl and alkenyloxyalkyl. In addition, replacement of two successive —$CH_2$— by —O— to form —O—O— or the like is not preferred. In alkyl or the like, replacement of —$CH_2$— of a methyl part (—$CH_2$—H) by —O— to form —O—H is not preferred, either.

Then, 2-fluoro-1,4-phenylene means two divalent groups described below. Fluorine may be leftward or rightward. The rule is also applied to an asymmetric divalent ring such as tetrahydropyran-2,5-diyl.

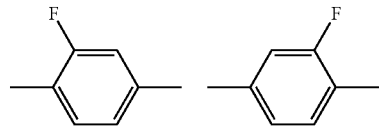

The invention includes the content as described in item 1 to item 12 as described below.

Item 1. A compound represented by formula (1):

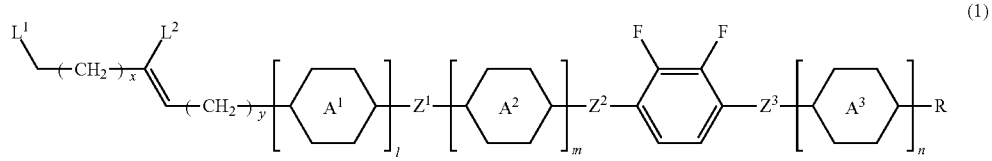

wherein, in formula (1),

R is hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;

ring $A^1$, ring $A^2$ and ring $A^3$ are independently 1,4-cyclohexylene, 1,4-cyclohexenylene, tetrahydropyran-2,5-diyl, 1,3-dioxane-2,5-diyl, pyrimidine-2,5-diyl, pyridine-2,5-diyl, naphthalene-2,6-diyl, decahydronaphthalene-2,6-diyl, 1,2,3,4-tetrahydronaphthalene-2,6-diyl, 1,4-phenylene, 2-fluoro-1,4-phenylene or 2,3-difluoro-1,4-phenylene;

$L^1$ and $L^2$ are independently hydrogen, fluorine or chlorine, and at least one of $L^1$ and $L^2$ is fluorine;

$Z^1$, $Z^2$ and $Z^3$ are independently a single bond, —$(CH_2)_2$—, —$CH_2O$—, —$OCH_2$—, —COO—, —OCO—, —$CF_2O$— or —$OCF_2$—;

x and y are independently an integer from 0 to 10; and l, m and n are independently 0, 1 or 2, and a sum of l, m and n is 1, 2 or 3.

Item 2. The compound according to item 1, represented by formula (1-1):

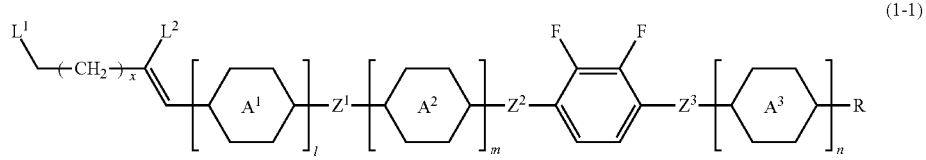

wherein, in formula (1-1),

R is hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;

ring $A^1$, ring $A^2$ and ring $A^3$ are independently 1,4-cyclohexylene, 1,4-cyclohexenylene, tetrahydropyran-2,5-diyl, 1,3-dioxane-2,5-diyl, pyridine-2,5-diyl, naphthalene-2,6-diyl, 1,4-phenylene, 2-fluoro-1,4-phenylene or 2,3-difluoro-1,4-phenylene;

$L^1$ and $L^2$ are independently hydrogen, fluorine or chlorine, and at least one of $L^1$ and $L^2$ is fluorine;

$Z^1$, $Z^2$ and $Z^3$ are independently a single bond, —$(CH_2)_2$—, —$CH_2O$—, —$OCH_2$—, —COO— or —OCO—;

x is an integer from 0 to 10; and l, m and n are independently 0, 1 or 2, and a sum of l, m and n is 1, 2 or 3.

Item 3. The compound according to item 1, represented by formula (1-2):

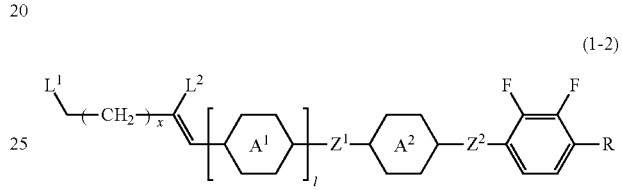

wherein, in formula (1-2),

R is hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;

ring $A^1$ and ring $A^2$ are independently 1,4-cyclohexylene, 1,4-cyclohexenylene, tetrahydropyran-2,5-diyl, 1,4-phenylene, 2-fluoro-1,4-phenylene or 2,3-difluoro-1,4-phenylene;

$L^1$ and $L^2$ are independently hydrogen or fluorine, and at least one of $L^1$ and $L^2$ is fluorine;

$Z^1$ and $Z^2$ are independently a single bond, —$(CH_2)_2$—, —$CH_2O$—, —$OCH_2$—, —COO— or —OCO—; and l is 0 or 1 and x is an integer from 0 to 10.

Item 4. The compound according to item 1, represented by formula (1-3):

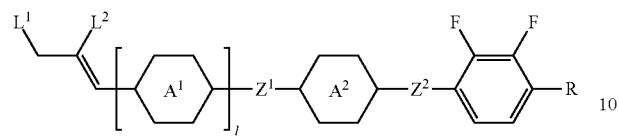 (1-3)

wherein, in formula (1-3),

R is hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;

ring $A^1$ and ring $A^2$ are independently 1,4-cyclohexylene, 1,4-cyclohexenylene, tetrahydropyran-2,5-diyl, 1,4-phenylene, 2-fluoro-1,4-phenylene or 2,3-difluoro-1,4-phenylene;

$L^1$ and $L^2$ are independently hydrogen or fluorine, and at least one of $L^1$ and $L^2$ is fluorine;

$Z^1$ and $Z^2$ are independently a single bond, —(CH$_2$)$_2$—, —CH$_2$O—, —OCH$_2$—, —COO— or —OCO—; and l is 0 or 1.

Item 5. The compound according to item 4, represented by any one of formulas (1-4-1) to (1-4-6) and formulas (1-5-1) to (1-5-6):

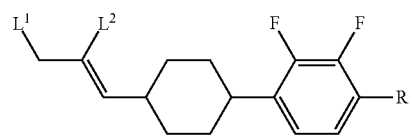 (1-4-1)

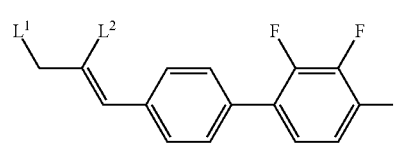 (1-4-2)

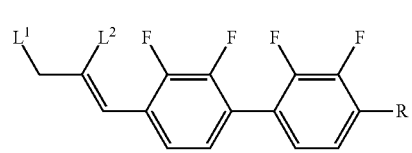 (1-4-3)

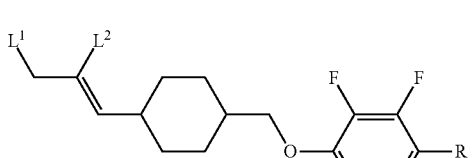 (1-4-4)

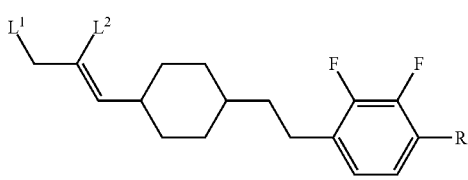 (1-4-5)

 (1-4-6)

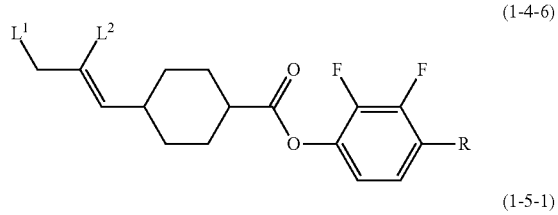 (1-5-1)

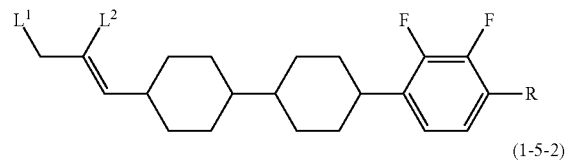 (1-5-2)

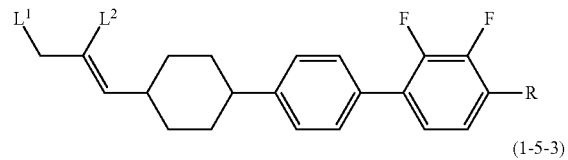 (1-5-3)

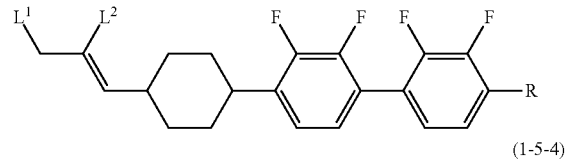 (1-5-4)

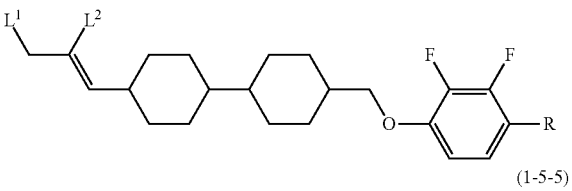 (1-5-5)

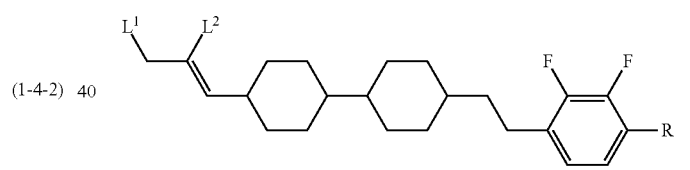 (1-5-6)

wherein, in formulas (1-4-1) to (1-4-6) and formulas (1-5-1) to (1-5-6),

R is independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; and $L^1$ and $L^2$ are independently hydrogen or fluorine, and at least one of $L^1$ and $L^2$ is fluorine.

Item 6. Use of at least one compound according to any one of items 1 to 5 as a component of a liquid crystal composition.

Item 7. A liquid crystal composition, containing at least one compound according to any one of items 1 to 5.

Item 8. The liquid crystal composition according to item 7, further containing at least one compound selected from the group of compounds represented by formulas (2), (3) and (4):

(2)

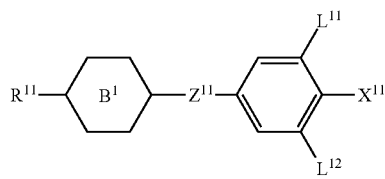

(3)

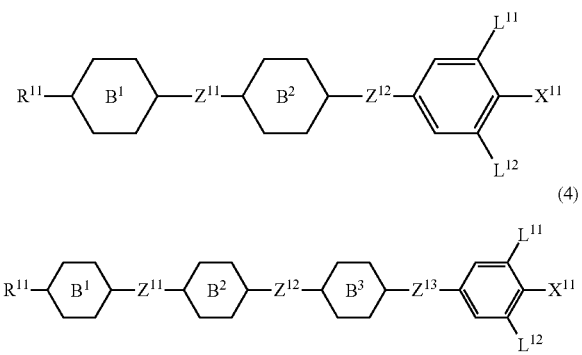

(4)

wherein, in formulas (2) to (4), $R^{11}$ is alkyl having 1 to 10 carbons or alkenyl having 2 to 10 carbons, and in the alkyl and the alkenyl, at least one of hydrogen may be replaced by fluorine and at least one of —$CH_2$— may be replaced by —O—;

$X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$;

ring $B^1$, ring $B^2$ and ring $B^3$ are independently 1,4-cyclohexylene, 1,4-phenylene in which at least one of hydrogen may be replaced by fluorine, or tetrahydropyran-2,5-diyl, 1,3-dioxane-2,5-diyl or pyrimidine-2,5-diyl;

$Z^{11}$, $Z^{12}$ and $Z^{13}$ are independently a single bond, —$CH_2CH_2$—, —CH=CH—, —COO—, —$CF_2O$—, —$OCF_2$—, —$CH_2O$— or —$(CH_2)_4$—; and $L^{11}$ and $L^{12}$ are independently hydrogen or fluorine; in formula (4), when both of ring $B^1$ and ring $B^2$ are 2,3-difluoro-1,4-phenylene, ring $B^3$ is not 1-pyrane-2,5-diyl, and when both of ring $B^2$ and ring $B^3$ are 2,3-difluoro-1,4-phenylene and $Z^5$ is a single bond, ring $B^1$ is not 1-pyrane-2,5-diyl.

Item 9. The liquid crystal composition according to item 7, further containing at least one compound selected from the group of compounds represented by formula (5):

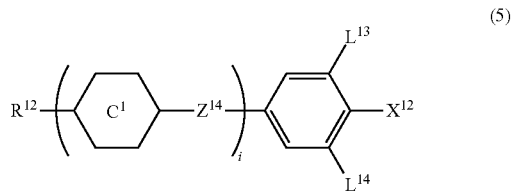

(5)

wherein, in formula (5), $R^{12}$ is alkyl having 1 to 10 carbons or alkenyl having 2 to 10 carbons, and in the alkyl and the alkenyl, at least one of hydrogen may be replaced by fluorine, and at least one of —$CH_2$— may be replaced by —O—;

$X^{12}$ is —C≡N or —C≡C—C≡N;

ring $C^1$ is 1,4-cyclohexylene, 1,4-phenylene in which at least one of hydrogen may be replaced by fluorine, or tetrahydropyran-2,5-diyl, 1,3-dioxane-2,5-diyl or pyrimidine-2,5-diyl;

$Z^{14}$ is a single bond, —$CH_2CH_2$—, —COO—, —$CF_2O$—, —$OCF_2$— or —$CH_2O$—;

$L^{13}$ and $L^{14}$ are independently hydrogen or fluorine; and i is 1, 2, 3 or 4.

Item 10. The liquid crystal composition according to item 7, further containing at least one compound selected from the group of compounds represented by formulas (6) to (12):

(6)

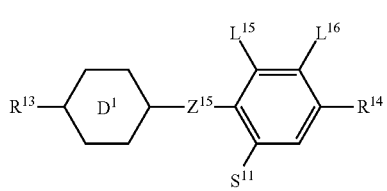

(7)

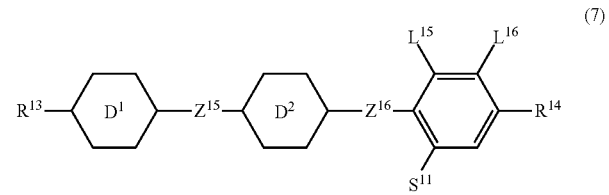

(8)

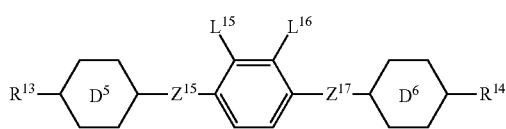

(9)

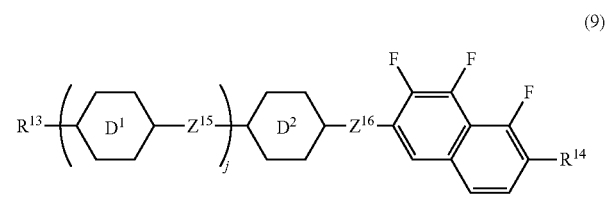

(10)

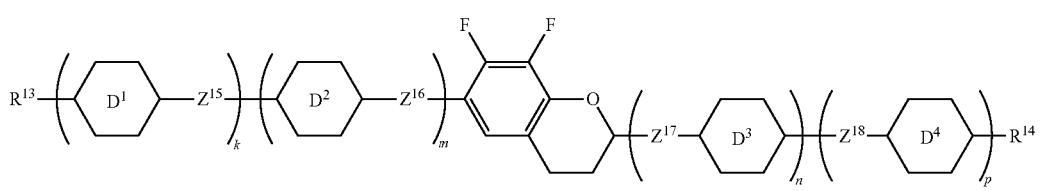

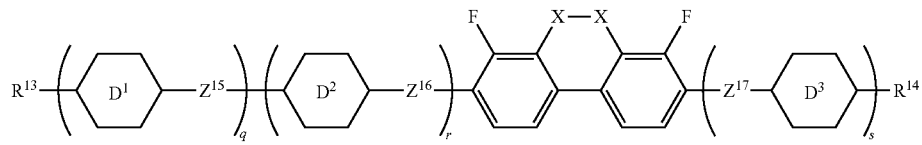
(11)

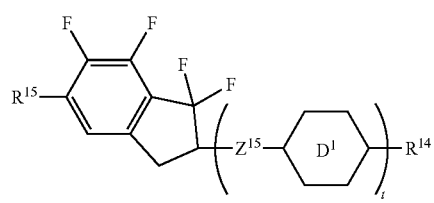
(12)

wherein, in formulas (6) to (12), $R^{13}$ and $R^{14}$ are independently alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;

$R^{15}$ is hydrogen, fluorine, alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;

$S^{11}$ is hydrogen or methyl;

X is —$CF_2$—, —O— or —CHF—;

ring $D^1$, ring $D^2$, ring $D^3$ and ring $D^4$ are independently 1,4-cyclohexylene, 1,4-cyclohexenylene, 1,4-phenylene in which at least one of hydrogen may be replaced by fluorine, or tetrahydropyran-2,5-diyl or decahydronaphthalene-2,6-diyl;

ring $D^5$ and ring $D^6$ are independently 1,4-cyclohexylene, 1,4-cyclohexenylene, 1,4-phenylene, tetrahydropyran-2,5-diyl or decahydronaphthalene-2,6-diyl;

$Z^{15}$, $Z^{16}$, $Z^{17}$ and $Z^{18}$ are independently a single bond, —$CH_2CH_2$—, —COO—, —$CH_2O$—, —$OCF_2$— or —$OCF_2CH_2CH_2$—;

$L^{15}$ and $L^{16}$ are independently fluorine or chlorine; and j, k, m, n, p, q, r and s are independently 0 or 1, a sum of k, m, n and p is 1 or 2, a sum of q, r and s is 0, 1, 2 or 3, and t is 1, 2 or 3.

Item 11. The liquid crystal composition according to item 7, further containing at least one compound selected from the group of compounds represented by formulas (13) to (15):

wherein, in formulas (13) to (15), $R^{16}$ and $R^{17}$ are independently alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;

ring $E^1$, ring $E^2$, ring $E^3$ and ring $E^4$ are independently 1,4-cyclohexylene, 1,4-phenylene, 2-fluoro-1,4-phenylene, 2,5-difluoro-1,4-phenylene or pyrimidine-2,5-diyl; and $Z^{19}$, $Z^{20}$ and $Z^{21}$ are independently a single bond, —$CH_2CH_2$—, —CH=CH—, or —COO—.

Item 12. The liquid crystal composition according to item 10, further containing at least one compound selected from the group of compounds represented by formulas (13), (14) and (15) according to item 11.

Item 13. The liquid crystal composition according to any one of items 7 to 12, further containing at least one optically active compound and/or at least one polymerizable compound.

Item 14. The liquid crystal composition according to any one of items 7 to 13, further containing at least one antioxidant and/or at least one ultraviolet light absorber.

Item 15. A liquid crystal display device, including the liquid crystal composition according to any one of items 7 to 14.

The compound, the liquid crystal composition and the liquid crystal display device according to the invention will be described in the order.

1-1. Compound (1)

Compound (1) of the invention will be described. Preferred examples of a terminal group, a ring structure and a bonding group in compound (1), and an effect of the groups on physical properties are also applied to a subordinate formula of compound (1).

(13)

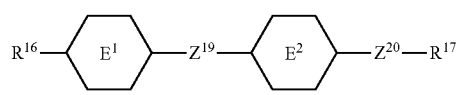

(14)

(15)

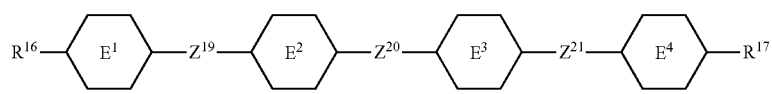

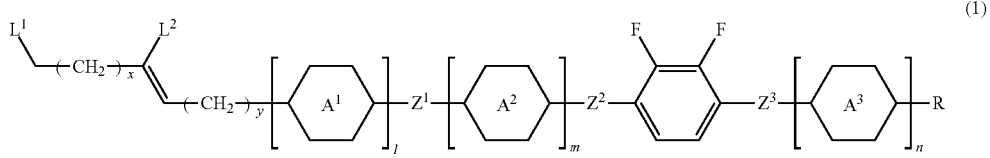

(1)

In formula (1), R is hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons. The groups have a straight chain or a branched chain, and do not include a cyclic group such as cyclohexyl. In the groups, the straight chain is preferred to the branched chain.

Preferred examples of R include alkyl, alkoxy, alkoxyalkyl and alkenyl. Further preferred examples of R include alkyl, alkoxy and alkenyl.

Specific examples of alkyl include —$CH_3$, —$C_2H_5$, —$C_3H_7$, —$C_4H_9$, —$O_5H_{11}$, —$C_6H_{13}$ and —$C_7H_{15}$. Specific examples of alkoxy include —$OCH_3$, —$OC_2H_5$, —$OC_3H_7$, —$OC_4H_9$, —$OC_5H_{11}$ and —$OC_6H_{13}$. Specific examples of alkoxyalkyl include —$CH_2OCH_3$, —$CH_2OC_2H_5$, —$CH_2OC_3H_7$, —$(CH_2)_2OCH_3$, —$(CH_2)_2OC_2H_5$, —$(CH_2)_2OC_3H_7$, —$(CH_2)_3OCH_3$, —$(CH_2)_4OCH_3$ and —$(CH_2)_5OCH_3$. Specific examples of alkenyl include —$CH=CH_2$, —$CH=CHCH_3$, —$CH_2CH=CH_2$, —$CH=CHC_2H_5$, —$CH_2CH=CHCH_3$, —$(CH_2)_2CH=CH_2$, —$CH=CHC_3H_7$, —$CH_2CH=CHC_2H_5$, —$(CH_2)_2CH=CHCH_3$ and —$(CH_2)_3CH=CH_2$. Specific examples of alkenyloxy include —$OCH_2CH=CH_2$, —$OCH_2CH=CHCH_3$ and —$OCH_2CH=CHC_2H_5$.

Preferred examples of R include —$CH_3$, —$C_2H_5$, —$C_3H_7$, —$C_4H_9$, —$C_5H_{11}$, —$OCH_3$, —$OC_2H_5$, —$OC_3H_7$, —$OC_4H_9$, —$OC_5H_{11}$, —$CH_2OCH_3$, —$(CH_2)_2OCH_3$, —$(CH_2)_3OCH_3$, —$CH_2CH=CH_2$, —$CH_2CH=CHCH_3$, —$(CH_2)_2CH=CH_2$, —$CH_2CH=CHC_2H_5$, —$(CH_2)_2CH=CHCH_3$, —$(CH_2)_3CH=CH_2$, —$(CH_2)_3CH=CHCH_3$, —$(CH_2)_3CH=CHC_2H_5$, —$(CH_2)_3CH=CHC_3H_7$, —$OCH_2CH=CH_2$, —$OCH_2CH=CHCH_3$ and —$OCH_2CH=CHC_2H_5$. Further preferred examples of $R^1$ or $R^2$ include —$CH_3$, —$C_2H_5$, —$C_3H_7$, —$OCH_3$, —$OC_2H_5$, —$OC_3H_7$, —$OC_4H_9$, —$(CH_2)_2CH=CH_2$, —$(CH_2)_2CH=CHCH_3$ and —$(CH_2)_2CH=CHC_3H_7$.

When R has the straight chain, a temperature range of the liquid crystal phase is wide and viscosity is small. When R has the branched chain, compatibility with other liquid crystal compounds is good. A compound in which R is optically active is useful as a chiral dopant. A reverse twisted domain that is generated in the liquid crystal display device can be prevented by adding the compound to the composition. A compound in which R is not optically active is useful as a component of the composition.

A preferred configuration of —CH=CH— in alkenyl depends on a position of a double bond. A trans configuration is preferred in alkenyl having the double bond in an odd-numbered position, such as —CH=$CHCH_3$, —CH=$CHC_2H_5$, —CH=$CHC_3H_7$, —CH=$CHC_4H_9$, —$C_2H_4$CH=$CHCH_3$ and —$C_2H_4$CH=$CHC_2H_5$. A cis configuration is preferred in alkenyl having the double bond at an even-numbered position, such as —$CH_2$CH=$CHCH_3$, —$CH_2$CH=$CHC_2H_5$ and —$CH_2$CH=$CHC_3H_7$. The alkenyl compound having a preferred configuration has a wide temperature range of the liquid crystal phase, a small viscosity and a large elastic constant.

However, if stability of the compound is taken into consideration, a group in which oxygen and oxygen are adjacent, such as $CH_3$—O—O—$CH_2$—, or a group in which double bond sites are adjacent, such as $CH_3$—CH=CH—CH=CH—, are not preferred.

In formula (1), ring $A^1$, ring $A^2$ and ring $A^3$ are independently 1,4-cyclohexylene, 1,4-cyclohexenylene, tetrahydropyran-2,5-diyl, 1,3-dioxane-2,5-diyl, pyrimidine-2,5-diyl, pyridine-2,5-diyl, naphthalene-2,6-diyl, decahydronaphthalene-2,6-diyl, 1,2,3,4-tetrahydronaphthalene-2,6-diyl, 1,4-phenylene, 2-fluoro-1,4-phenylene or 2,3-difluoro-1,4-phenylene.

Preferred examples of ring $A^1$, ring $A^2$ or ring $A^3$ include 1,4-cyclohexylene, 1,4-phenylene and 2,3-difluoro-1,4-phenylene. Further preferred examples include 1,4-cyclohexylene and 1,4-phenylene. Particularly preferred examples include 1,4-cyclohexylene. Then, 1,4-cyclohexylene has cis and trans configurations. From a viewpoint of a high maximum temperature, the trans configuration is preferred.

When at least one of ring $A^1$, ring $A^2$ and ring $A^3$ is 1,4-cyclohexylene, the viscosity is small. When the compound is added, the viscosity of the composition can be decreased. Moreover, when at least one of ring $A^1$, ring $A^2$ and ring $A^3$ is tetrahydropyran-2,5-diyl, the compound is excellent in compatibility with other liquid crystal compounds. When the compound is added, the compatibility of the composition can be improved. When at least one of ring $A^1$, ring $A^2$ and ring $A^3$ is 2,3-difluoro-1,4-phenylene, dielectric anisotropy is negatively large. When the compound is added, the dielectric anisotropy of the composition can be negatively increased.

In formula (1), $Z^1$, $Z^2$ and $Z^3$ are independently a single bond, —$(CH_2)_2$—, —$CH_2O$—, —$OCH_2$—, —COO—, —OCO—, —$CF_2O$— or —$OCF_2$—.

A compound in which $Z^1$, $Z^2$ or $Z^3$ is —COO— or —OCO— has a high maximum temperature, and therefore such a compound is preferred. A compound in which $Z^1$, $Z^2$ or $Z^3$ is —$CH_2O$— or —$OCH_2$— has a large negative dielectric anisotropy, and therefore such a compound is preferred. A compound in which $Z^1$, $Z^2$ or $Z^3$ is a single bond or —$(CH_2)_2$—, —$CF_2O$— or —$OCF_2$— has the small viscosity, and therefore such a compound is preferred.

If the stability of the compound is taken into consideration, a single bond, —$(CH_2)_2$—, —$CH_2O$— or —$OCH_2$— is preferred, and a single bond or —$(CH_2)_2$— is further preferred. If an increase in the clearing point is taken into consideration, when any one of $Z^1$, $Z^2$ and $Z^3$ is —$(CH_2)_2$—, —$CH_2O$—, —$OCH_2$—, —COO— or —OCO—, a remainder is preferably a single bond. A case where all of $Z^1$, $Z^2$ and $Z^3$ are a single bond is further preferred.

In formula (1), $L^1$ and $L^2$ are independently hydrogen, fluorine or chlorine, and at least one of $L^1$ and $L^2$ is fluorine.

A compound in which both of $L^1$ and $L^2$ are fluorine has a high maximum temperature and the negatively large dielectric anisotropy, and therefore such a compound is preferred.

In formula (1), l, m and n are independently 0, 1 or 2, and a sum of l, m and n is 1, 2 or 3. When the sum of l, m and n is 1, the viscosity is small. When the sum of l, m and n is 2, a balance between the viscosity and the maximum temperature is excellent. When the sum of l, m and n is 3, the maximum temperature is high.

Compound (1) has a fluorine-containing alkenyl group, and 2,3-difluoro-1,4-phenylene. Due to such a structural effect, the compound has a suitable optical anisotropy, the large negative dielectric anisotropy and a suitable elastic constant. The compound has the large negative dielectric anisotropy due to an effect of a fluorine-substituted alkenyl group. The compound is particularly excellent from a viewpoint of a high maximum temperature and the large negative dielectric anisotropy.

As described above, a compound having objective physical properties can be obtained by suitably selecting kinds of the terminal group, the ring structure, the bonding group or the like. Compound (1) may contain an isotope such as $^2$H (deuterium) and $^{13}$C in an amount larger than an amount of natural abundance because no significant difference exists in physical properties of the compound.

1-2. Preferred Compound

Specific examples of preferred compound (1) include compound (1-1) described in item 2, compound (1-2) described in item 3, compound (1-3) described in item 4 and compounds (1-4-1) to (1-5-6) described in item 5.

Compounds (1-1) to (1-3) have fluorine-containing alkenyl and 2,3-difluoro-1,4-phenylene, and are asymmetrical in structure. Therefore, the compounds are preferred from a viewpoint of a high stability to heat or light, a low minimum temperature of the liquid crystal phase, a high maximum temperature of the liquid crystal phase, the large negative dielectric anisotropy and the suitable elastic constant. A case where $Z^2$ is a single bond in compounds (1-1) to (1-3) is further preferred from a viewpoint of a high maximum temperature. A case where $Z^2$ is —(CH$_2$)$_2$— is further preferred from a viewpoint of the small viscosity. A case where $Z^2$ is —CH$_2$O— or —OCH$_2$— is further preferred from a viewpoint of the large negative dielectric anisotropy. A case where $Z^2$ is —COO— or —OCO— is still further preferred from a viewpoint of a high maximum temperature.

Compounds (1-4-1) to (1-4-6) and compounds (1-5-1) to (1-5-6) as described in item 5 have fluorine-containing alkenyl and 2,3-difluoro-1,4-phenylene, and therefore are still further preferred from a viewpoint of a high stability to heat or light, a low minimum temperature of the liquid crystal phase, the suitable optical anisotropy, the large negative dielectric anisotropy and the suitable elastic constant.

A composition containing compound (1-1), in particular, compounds (1-1) to (1-3), compounds (1-4-1) to (1-4-6) or compounds (1-5-1) to (1-5-6) has a high maximum temperature, a low minimum temperature, the small viscosity, the suitable optical anisotropy, the large negative dielectric anisotropy and the suitable elastic constant. The composition is stable under conditions in which the liquid crystal display device is ordinarily used, and the compound is not precipitated as a crystal (or a smectic phase) even when the composition is kept at a low temperature. Accordingly, compound (1-1) can be suitably applied to a liquid crystal composition used for a liquid crystal display device having an operating mode such as IPS, VA or PSA.

1-3. Synthesis of Compound (1)

A method for synthesizing compound (1) will be described. Compound (1-1) can be prepared by suitably combining techniques of synthetic organic chemistry. A method for introducing an objective terminal group, ring and bonding group into a starting material is described in books such as Organic Syntheses (John Wiley & Sons, Inc.), Organic Reactions (John Wiley & Sons, Inc.), Comprehensive Organic Synthesis (Pergamon Press) and New Experimental Chemistry Course (Shin Jikken Kagaku Koza, in Japanese) (Maruzen Co., Ltd.).

1-3-1. Formation of a Bonding Group

An example of a method for forming a bonding group in compound (1) is as described in a scheme below. In the scheme, MSG$^1$ (or MSG$^2$) is a monovalent organic group having at least one ring. Monovalent organic groups represented by a plurality of MSG$^1$ (or MSG$^2$) may be identical or different. Compounds (1A) to (1D) correspond to compound (1-1).

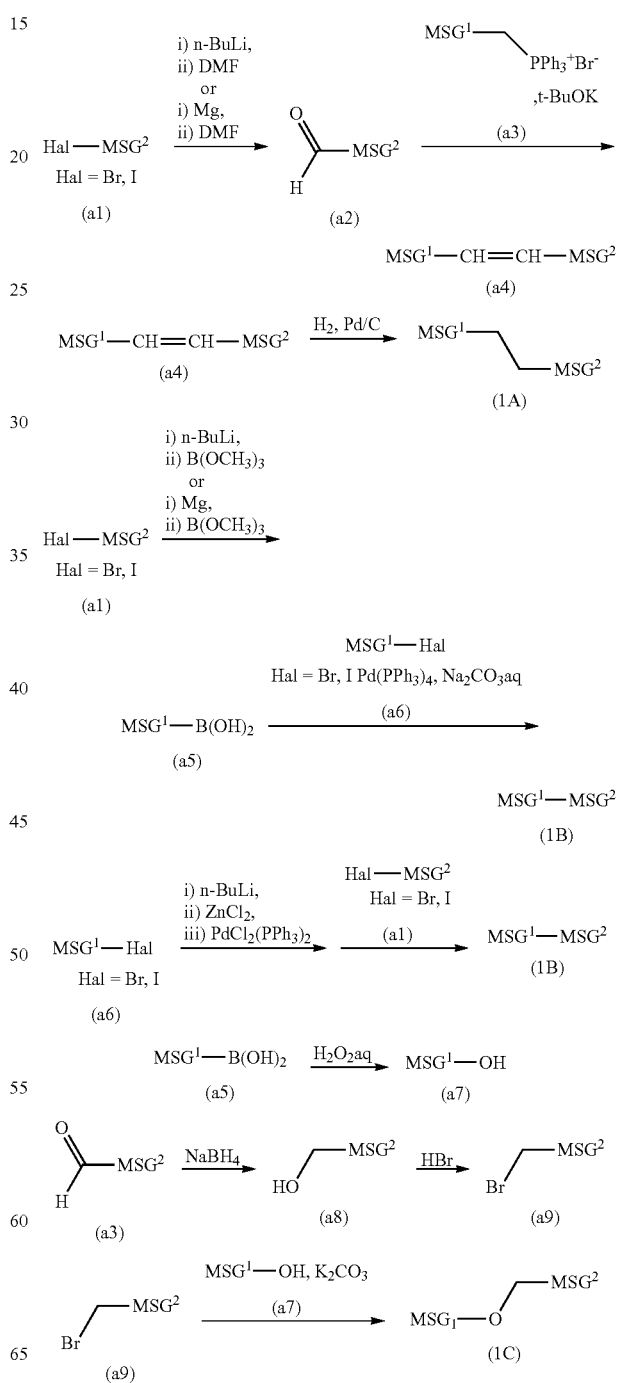

-continued

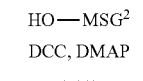
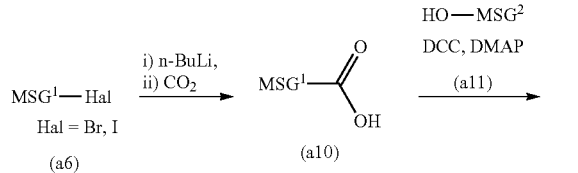

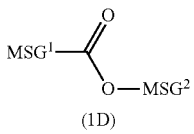

(1) Formation of —(CH$_2$)$_2$—

Aldehyde (a2) is obtained by allowing organohalogen compound (a1) to react with butyllithium (or magnesium), and then allowing the resulting intermediate to react with formamide such as N,N-dimethylformamide (DMF). Compound (a4) having a double bond is obtained by allowing the aldehyde (a2) to react with phosphorus ylide obtained by treating phosphonium salt (a3) with a base such as potassium t-butoxide. Compound (1A) is prepared by hydrogenating compound (a4) in the presence of a catalyst such as palladium on carbon (NYC).

(2) Formation of a Single Bond

A Grignard reagent (or a lithium salt) is prepared by allowing organohalogen compound (a1) to react with magnesium (or butyllithium). Dihydroxyborane (a5) is obtained by allowing the Grignard reagent (or the lithium salt) to react with a boric acid ester such as trimethyl borate, and then by hydrolyzing the resulting product in the presence of acid such as hydrochloric acid. Compound (1B) is prepared by allowing compound (a5) to react with organohalogen compound (a6) in an aqueous carbonate solution in the presence of a tetrakis (triphenylphosphine)palladium (Pd(PPh$_3$)$_4$) catalyst.

A method described below can also be applied. Organohalogen compound (a6) is allowed to react with butyl lithium and further with zinc chloride. Compound (1B) is prepared by allowing the resulting intermediate compound to react with compound (a1) in the presence of bistriphenylphosphine dichloropalladium (Pd(PPh$_3$)$_2$Cl$_2$).

(3) Formation of —CH$_2$O— or —OCH$_2$—

Alcohol (a7) is obtained by oxidizing dihydroxyborane (a5) with an oxidizing agent such as hydrogen peroxide. Separately, alcohol (a8) is obtained by reducing aldehyde (a3) with a reducing agent such as sodium borohydride. Halogen compound (a9) is obtained by halogenating the alcohol (a8) with hydrobromic acid or the like. Compound (1C) is prepared by allowing the halide (a9) to react, in the presence of potassium carbonate or the like, with the alcohol (a7) previously obtained.

(4) Formation of —COO— or —OCO—

Carboxylic acid (a10) is obtained by allowing compound (a6) to react with n-butyl lithium and subsequently with carbon dioxide. Compound (1D) having —COO— is prepared by dehydrating the carboxylic acid (a10) and phenol (a11) in the presence of 1,3-dicyclohexylcarbodiimide (DCC) and 4-dimethylaminopyridine (DMAP). Compound having —OCO— can also be prepared according to the method.

1-3-2. Synthesis Example

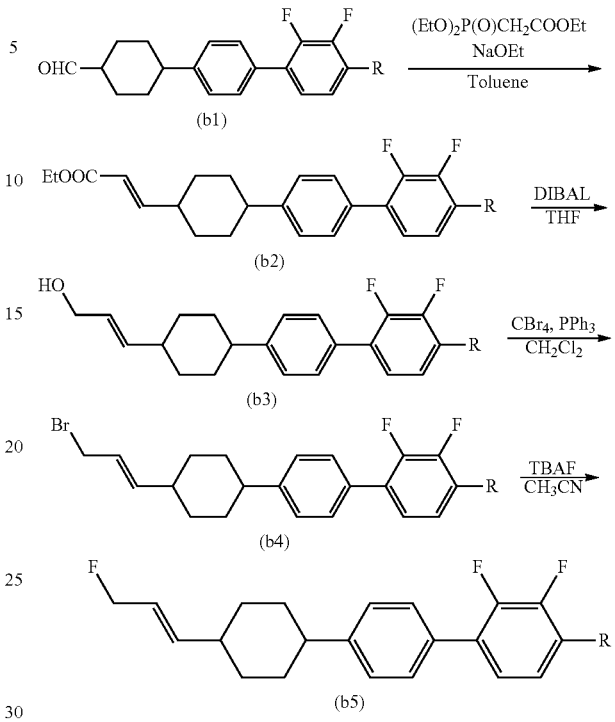

An example of a method for preparing compound (1) is as described below. Compound (b2) is obtained by allowing aldehyde (b1) to react in toluene in the presence of ethyl diethylphosphonoacetate and sodium ethoxide. Compound (b3) is obtained by allowing the compound (b2) to react in THF in the presence of diisobutylaluminium hydride. Compound (b4) is obtained by allowing the compound (b3) to react in dichloromethane in the presence of carbon tetrabromide and triphenyl phosphine. Compound (b5) being one example of compound (1) is prepared by allowing tetrabutylammonium fluoride to react in acetonitrile.

2. Composition (1)

Liquid crystal composition (1) of the invention will be described below. Composition (1) contains at least one compound (1) as component A. Composition (1) may contain two or more kinds of compound (1). Composition (1) may contain only compound (1) as a component of the liquid crystal composition. Composition (1) preferably contains at least one of compound (1) in the range of approximately 1 to approximately 99% by weight in order to develop excellent physical properties. In a composition having a positive dielectric anisotropy, a preferred content of compound (1) is in the range of approximately 5 to approximately 60% by weight. In a composition having the negative dielectric anisotropy, a preferred content of compound (1) is approximately 30% by weight or less. Composition (1) may also contain compound (1) and various kinds of liquid crystal compounds that are not described herein.

A preferred composition contains a compound selected from components B, C, D and E shown below. When composition (1) is prepared, a component thereof can be selected, for example, by taking the dielectric anisotropy of liquid crystal compound (1) into consideration. A composition prepared by suitably selecting a component has a high maximum temperature of the nematic phase, a low minimum temperature of the nematic phase, the small viscosity, the suitable optical anisotropy, a large dielectric anisotropy and the suitable elastic constant.

Component B includes compounds (2) to (4) described in item 8. Component C includes compound (5) described in item 9. Component D includes compounds (6) to (12) described in item 10. Component E includes compounds (13) to (15) described in item 11. The components will be described in the order.

Component B includes a compound having a halogen-containing group or a fluorine-containing group at a right terminal. Preferred examples of component B include compounds (2-1) to (2-16), compounds (3-1) to (3-113) and compounds (4-1) to (4-57).

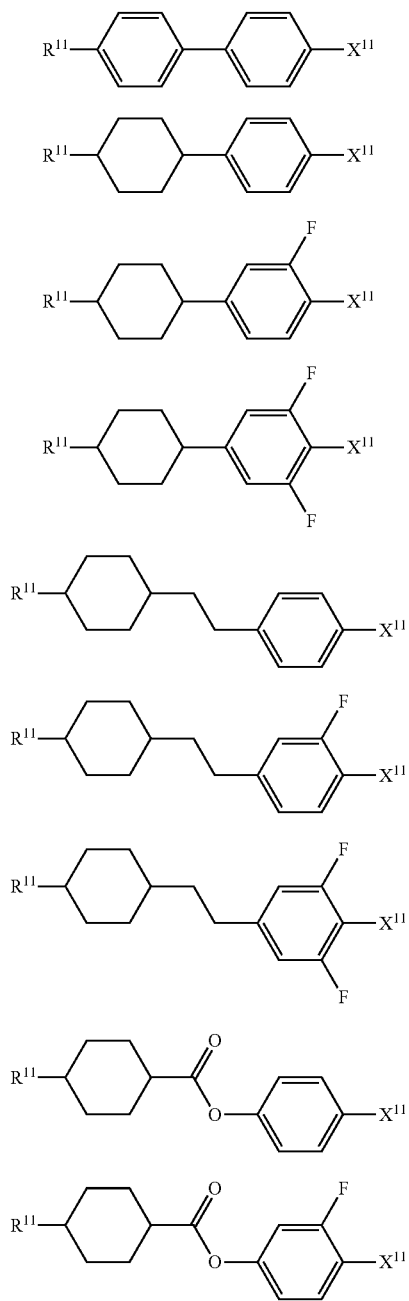

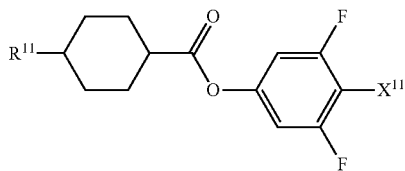

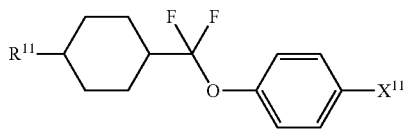

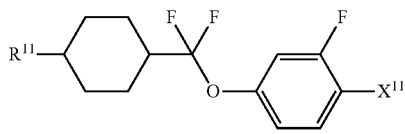

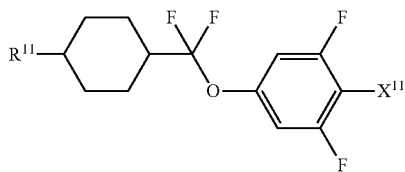

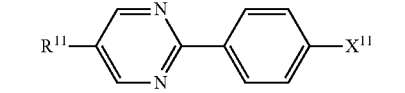

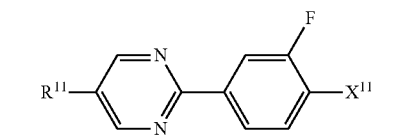

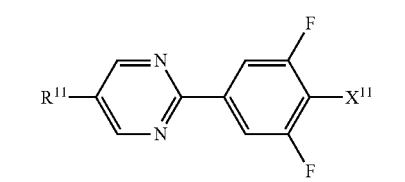

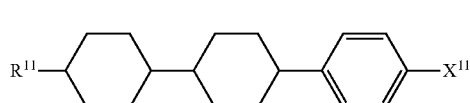

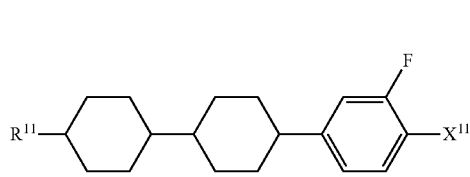

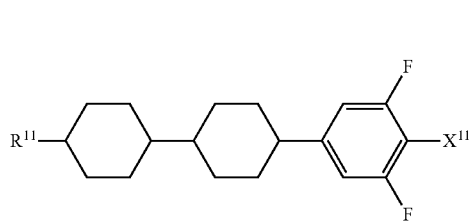

(3-4) 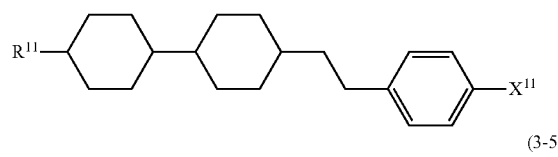
(3-5) 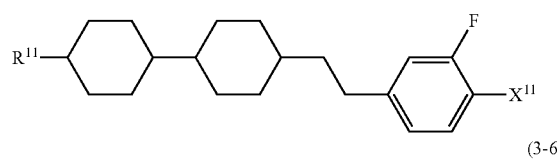
(3-6) 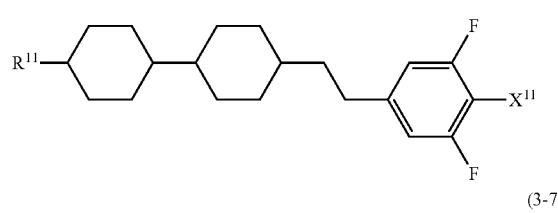
(3-7) 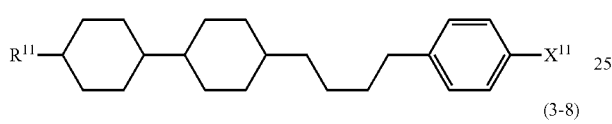
(3-8) 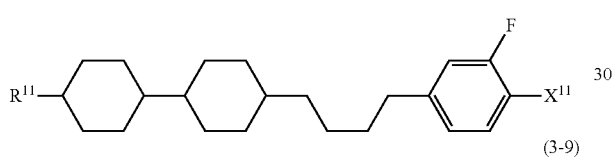
(3-9) 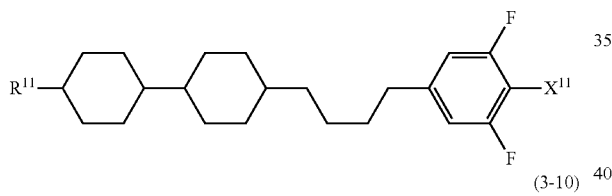
(3-10) 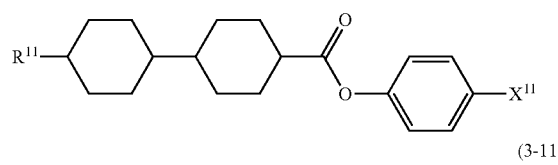
(3-11) 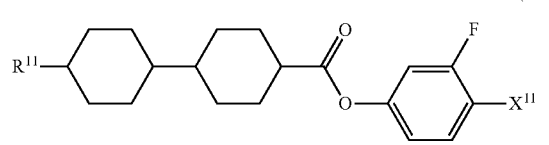
(3-12) 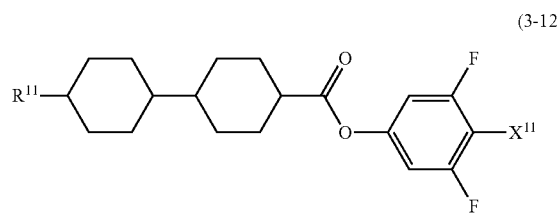
(3-13) 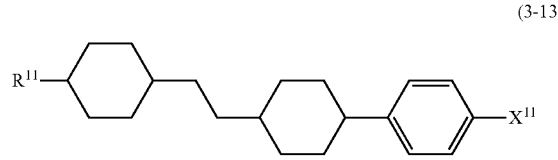
(3-14) 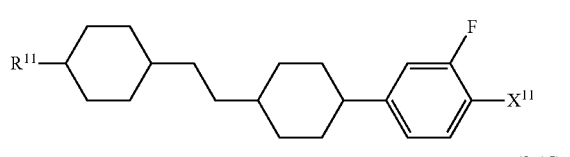
(3-15) 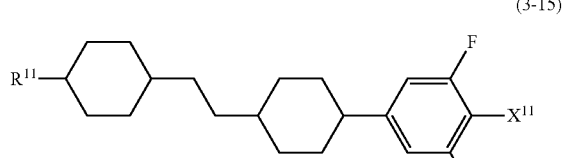
(3-16) 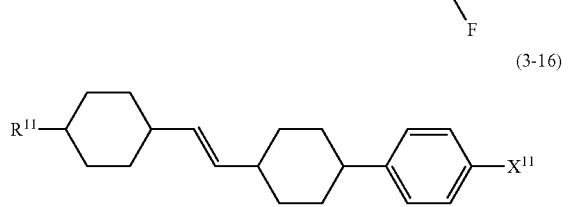
(3-17) 
(3-18) 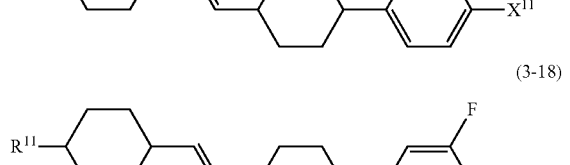
(3-19) 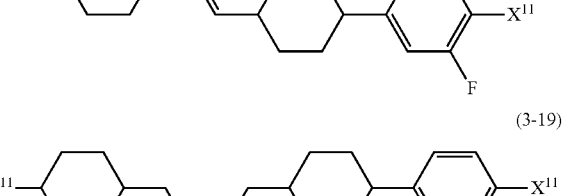
(3-20) 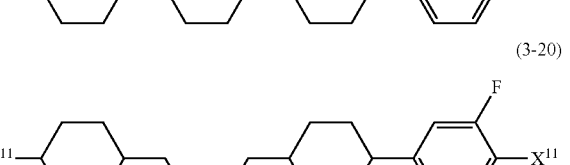
(3-21) 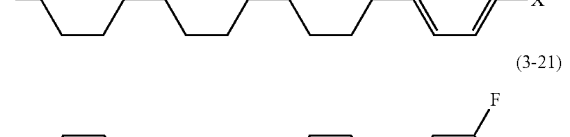
(3-22) 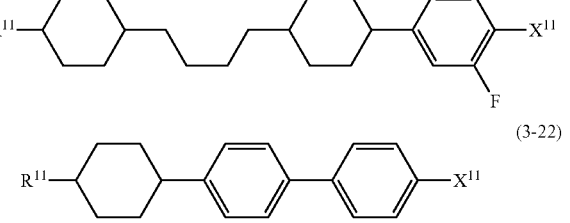
(3-23) 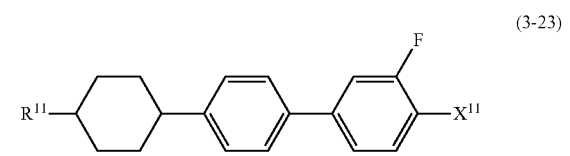

(3-24) 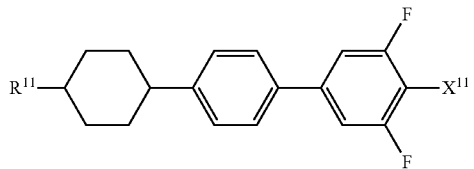
(3-25) 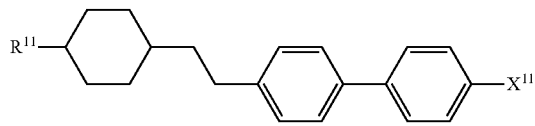
(3-26) 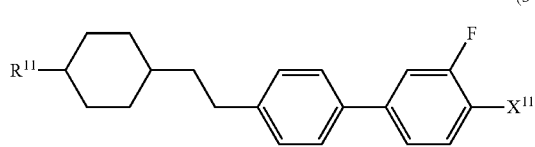
(3-27) 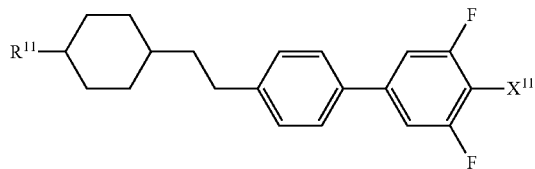
(3-28) 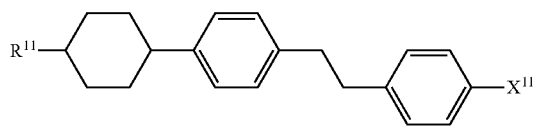
(3-29) 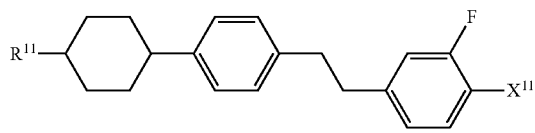
(3-30) 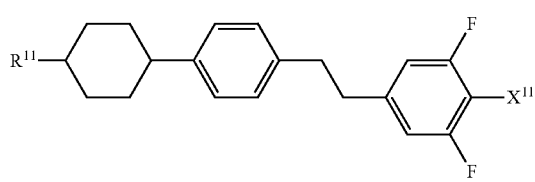
(3-31) 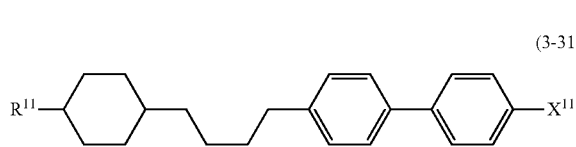
(3-32) 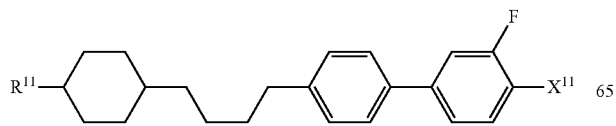
(3-33) 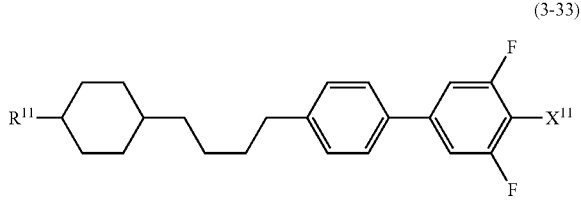
(3-34) 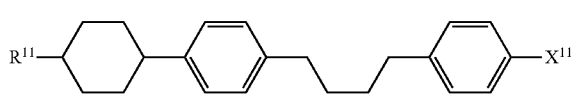
(3-35) 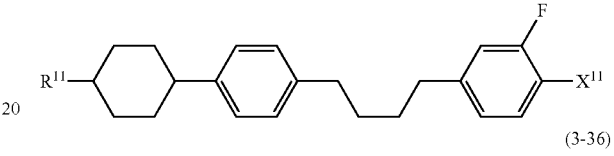
(3-36) 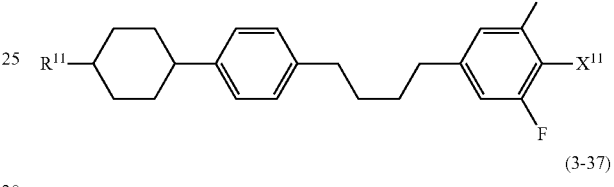
(3-37) 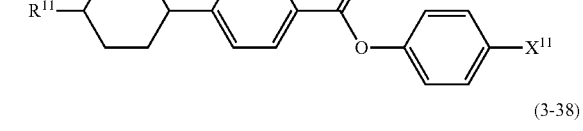
(3-38) 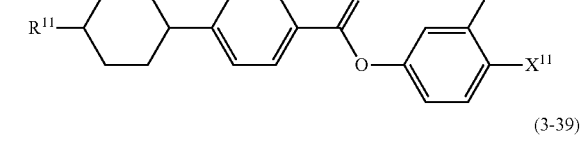
(3-39) 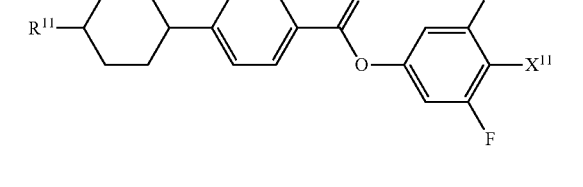
(3-40) 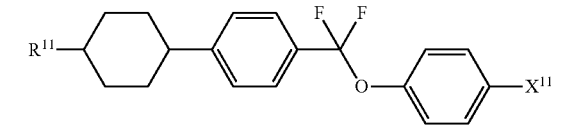
(3-41) 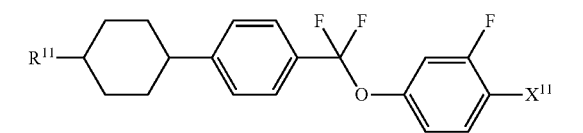

(3-42)
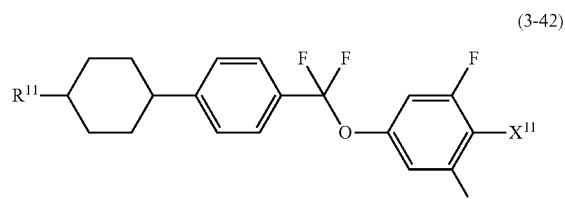
(3-43)
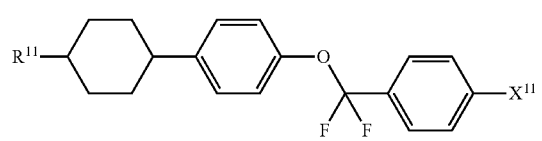
(3-44)
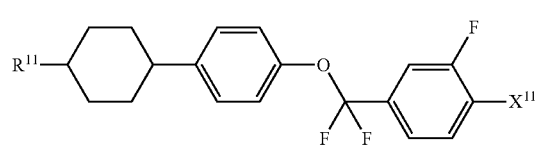
(3-45)
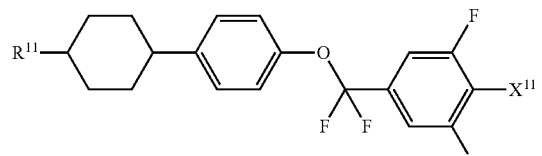
(3-46)
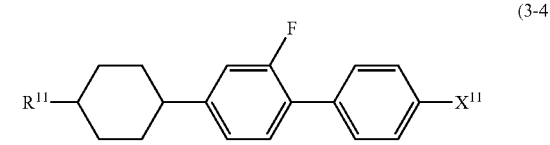
(3-47)
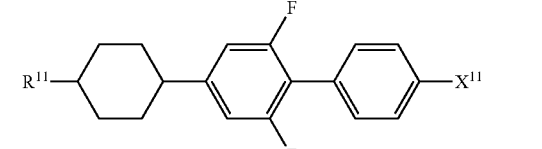
(3-48)
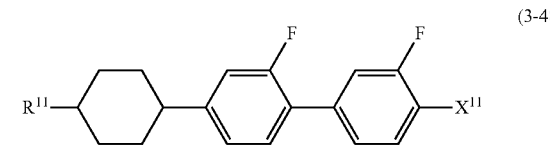
(3-49)
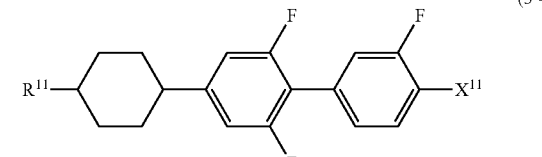
(3-50)
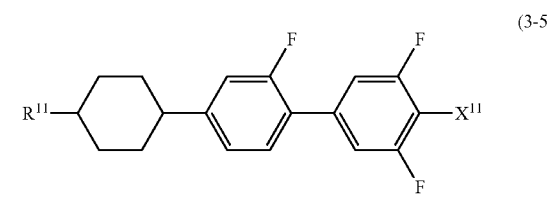
(3-51)
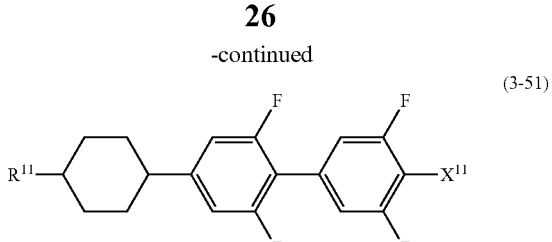
(3-52)
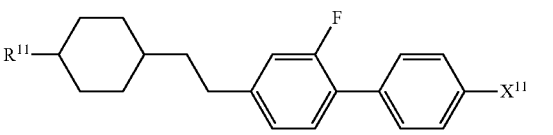
(3-53)
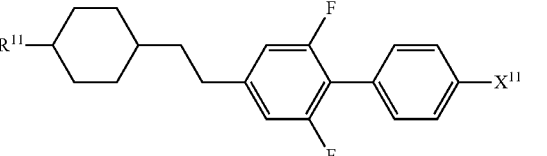
(3-54)
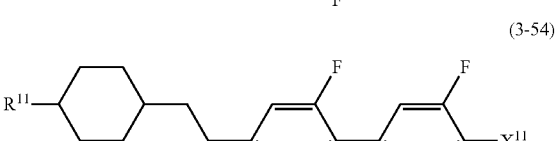
(3-55)
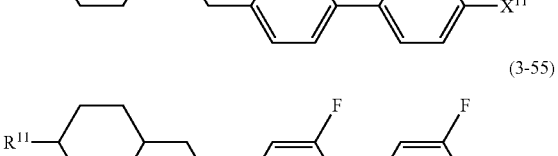
(3-56)
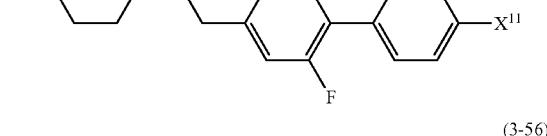
(3-57)
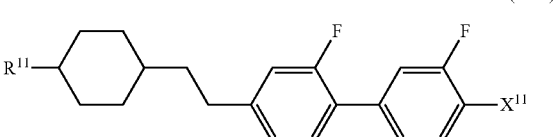
(3-58)
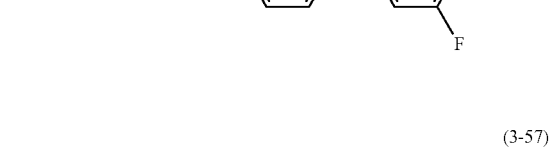

(3-59) 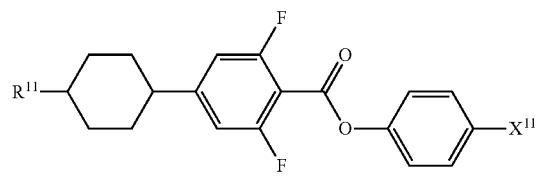
(3-60) 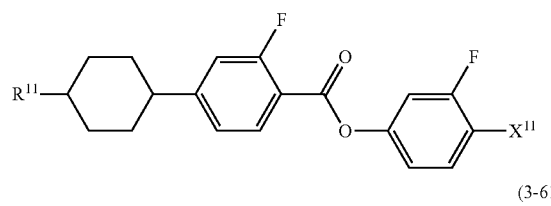
(3-61) 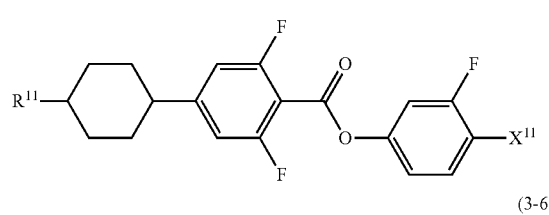
(3-62) 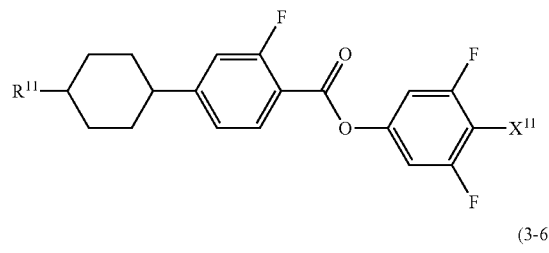
(3-63) 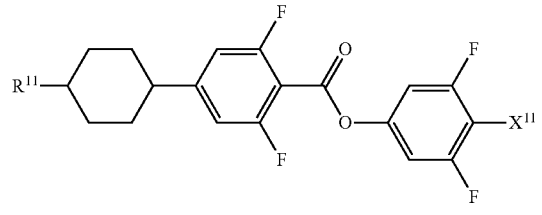
(3-64) 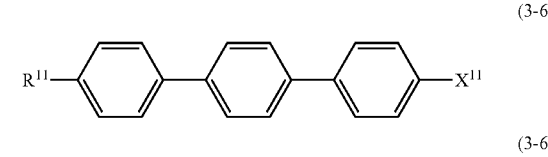
(3-65) 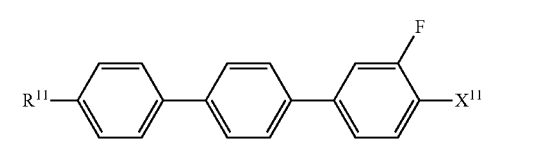
(3-66) 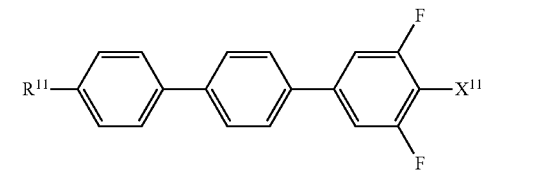
(3-67) 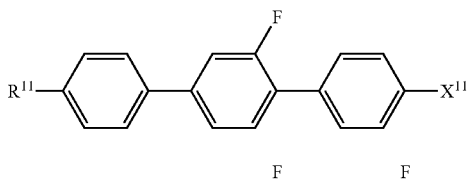
(3-68) 
(3-69) 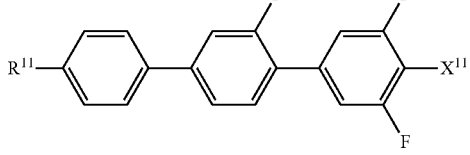
(3-70) 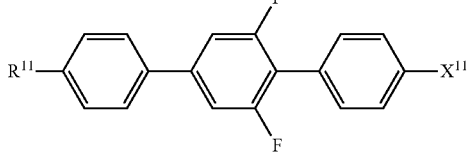
(3-71) 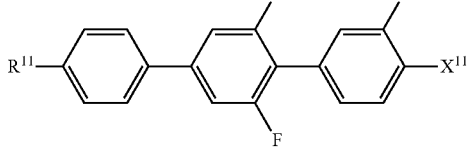
(3-72) 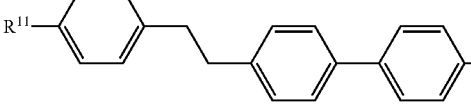
(3-73) 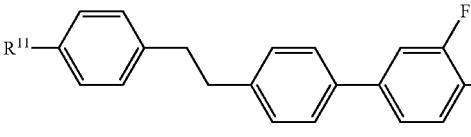
(3-74) 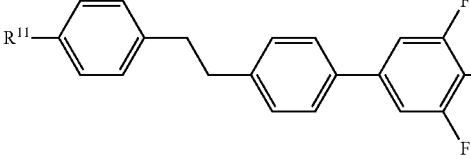
(3-75) 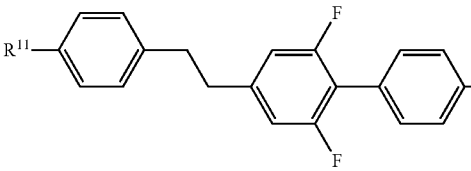

(3-76) 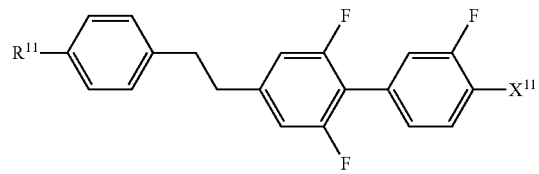
(3-77) 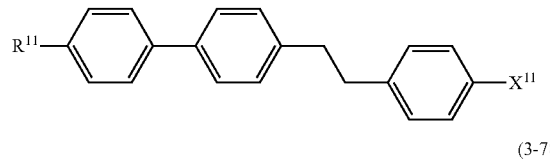
(3-78) 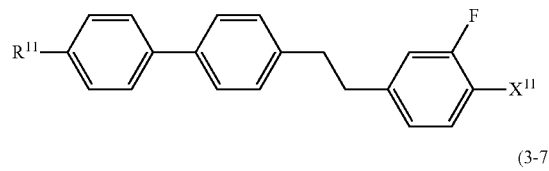
(3-79) 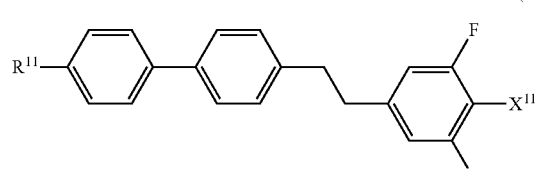
(3-80) 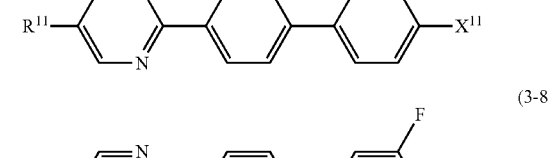
(3-81) 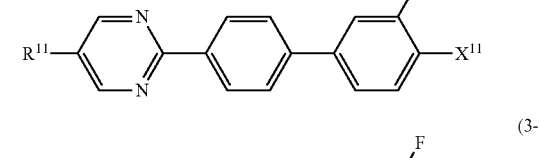
(3-82) 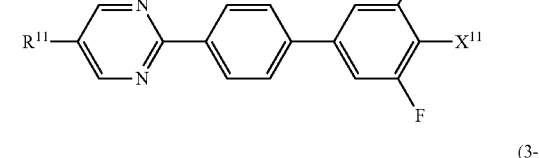
(3-83) 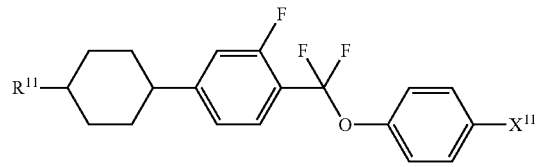
(3-84) 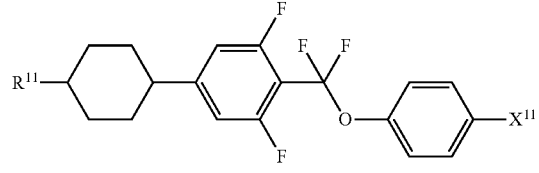
(3-85) 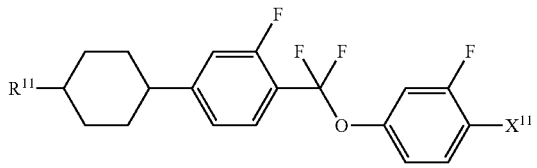
(3-86) 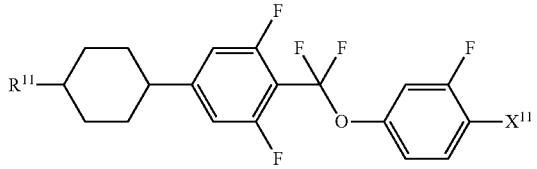
(3-87) 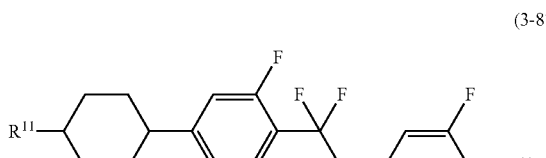
(3-88) 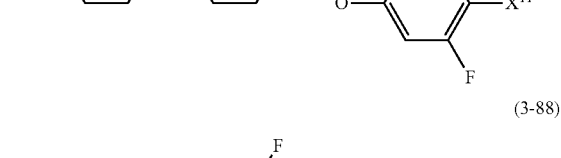
(3-89) 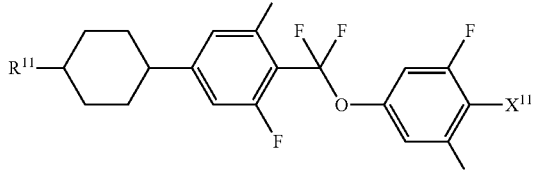
(3-90) 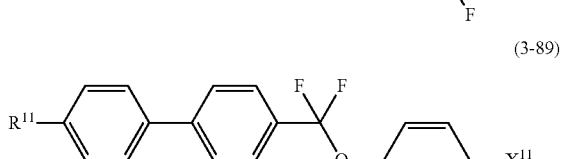
(3-91) 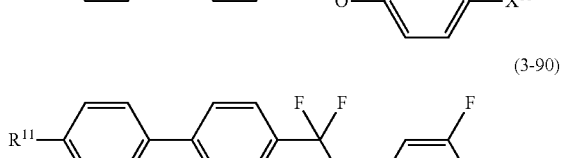
(3-92)

(3-93) 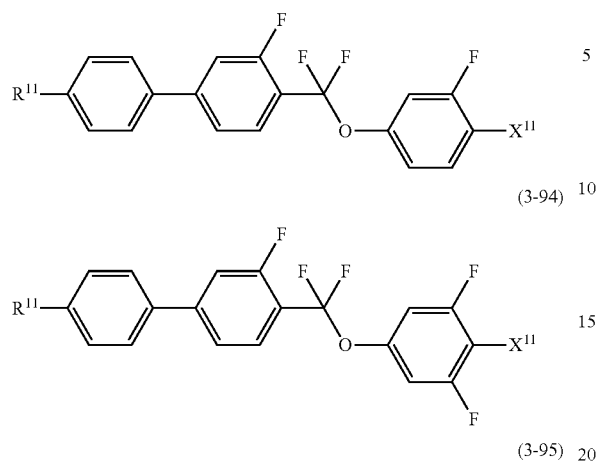
(3-94)
(3-95)
(3-96)
(3-97)
(3-98) 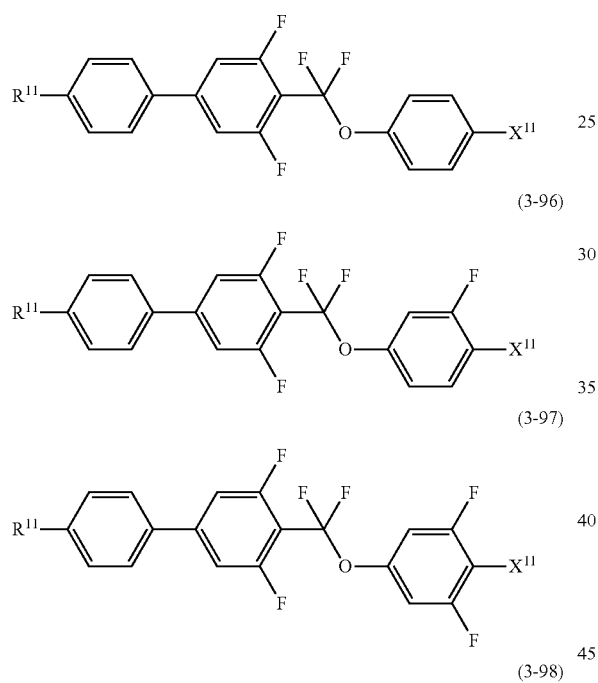
(3-99)
(3-100)
(3-101) 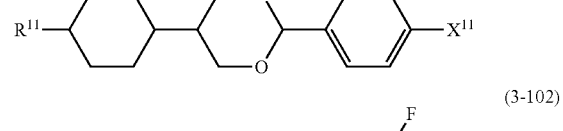
(3-102) 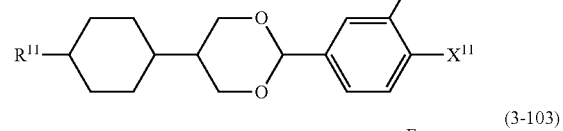
(3-103) 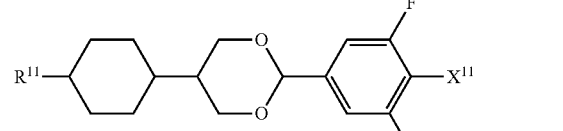
(3-104) 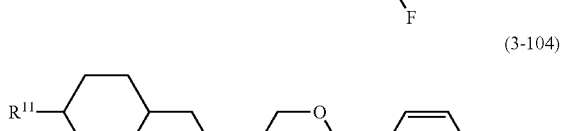
(3-105) 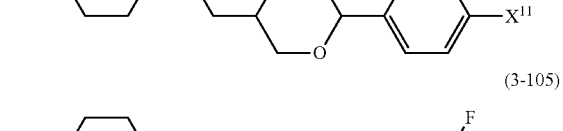
(3-106) 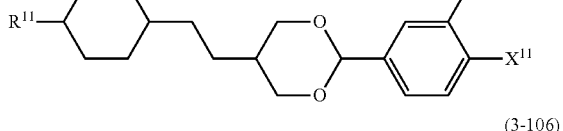
(3-107) 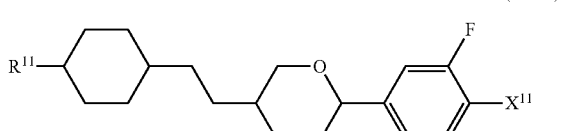
(3-108) 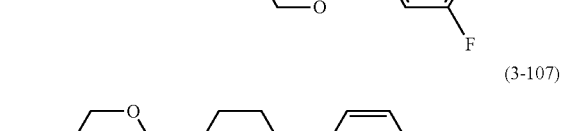
(3-109) 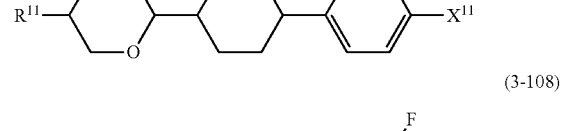
(3-110)

(3-111)
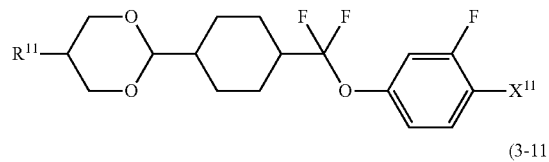
(3-112)
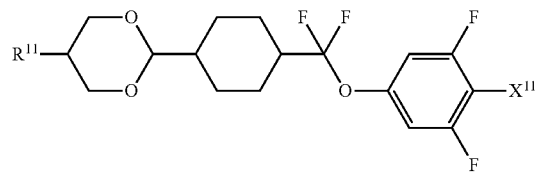
(3-113)
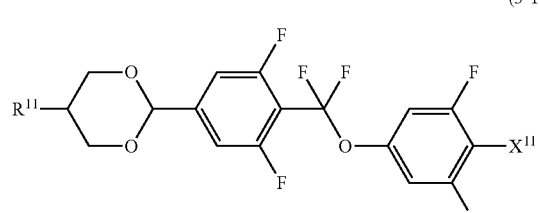
(4-1)
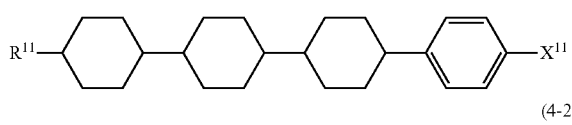
(4-2)
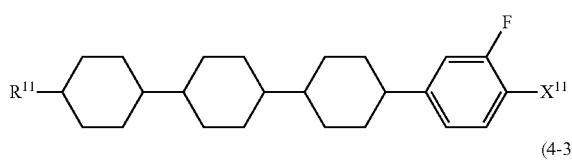
(4-3)
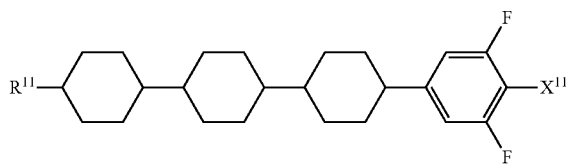
(4-4)
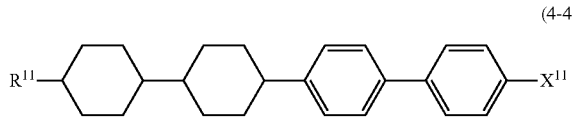
(4-5)
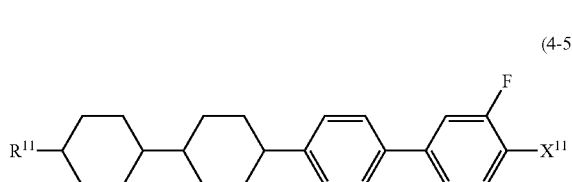
(4-6)
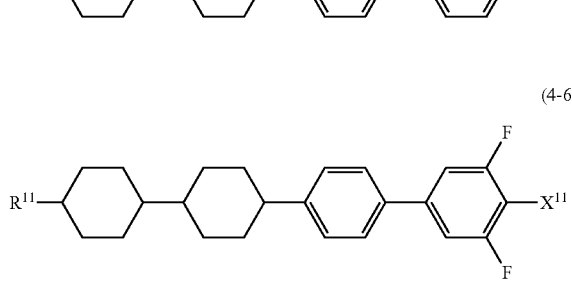
(4-7)
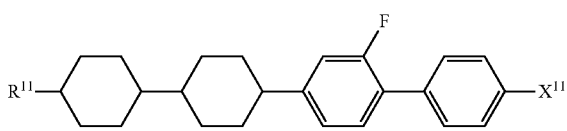
(4-8)
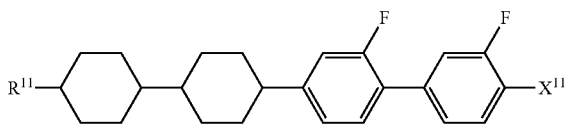
(4-9)
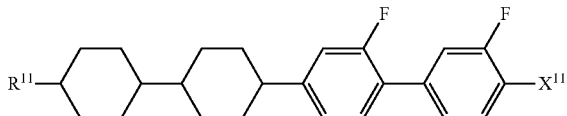
(4-10)
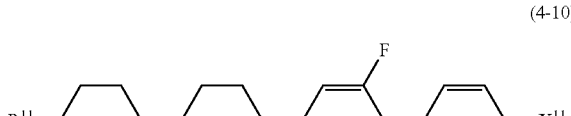
(4-11)
(4-12)
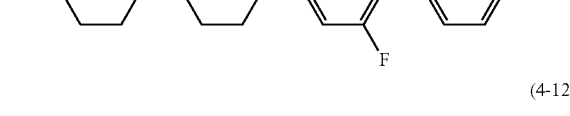
(4-13)
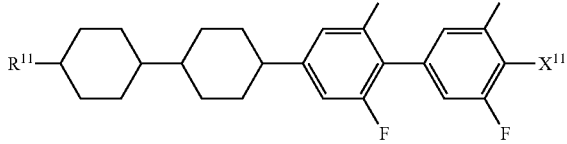
(4-14)
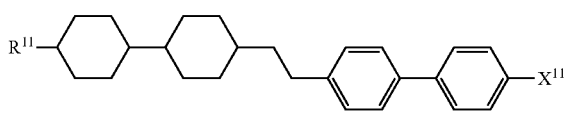
(4-15)
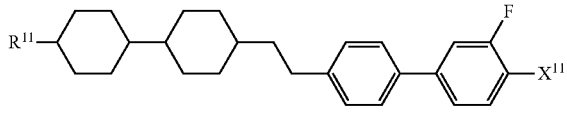

-continued
(4-16)
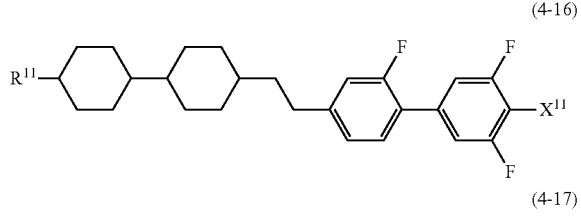
(4-17)
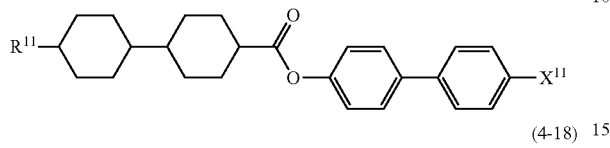
(4-18)
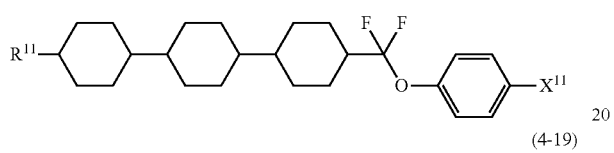
(4-19)
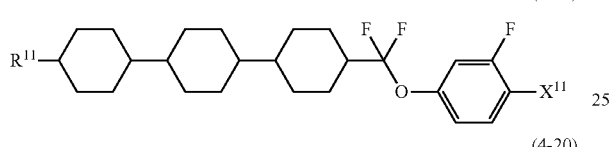
(4-20)
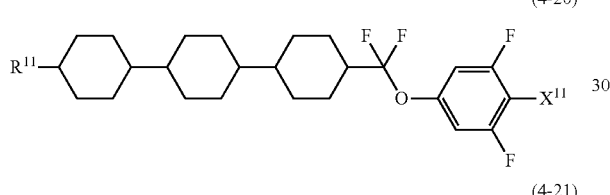
(4-21)
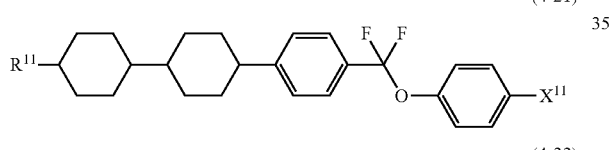
(4-22)
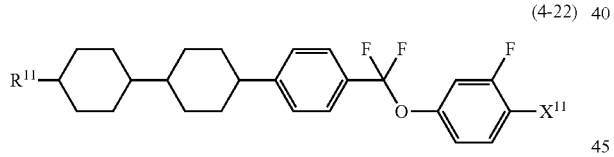
(4-23)
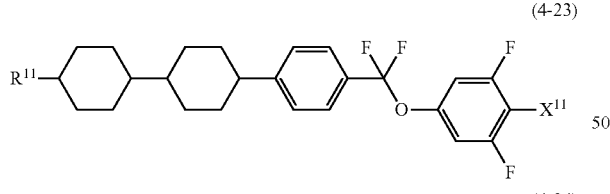
(4-24)
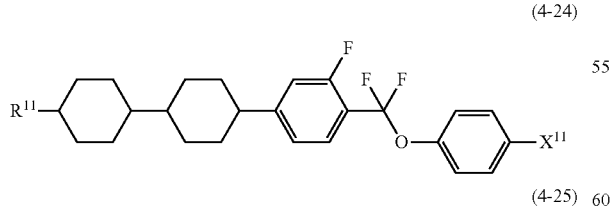
(4-25)
(4-26)
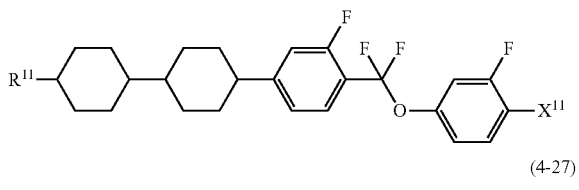
(4-27)
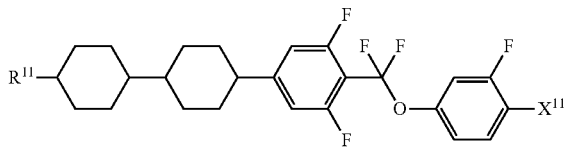
(4-28)
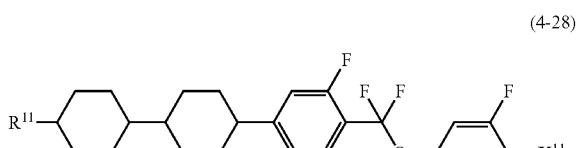
(4-29)
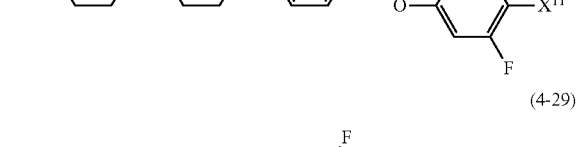
(4-30)
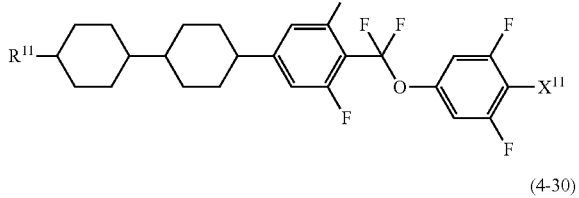
(4-31)
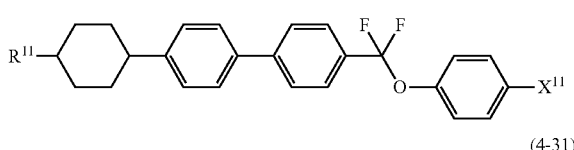
(4-32)
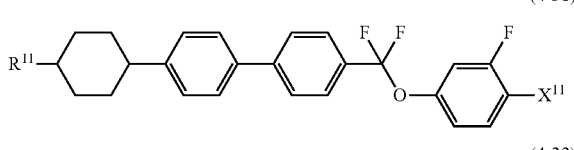
(4-33)
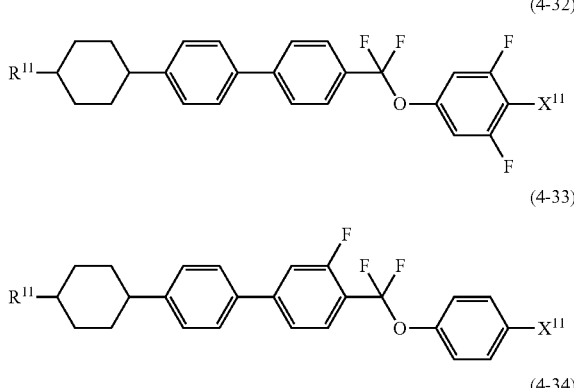
(4-34)
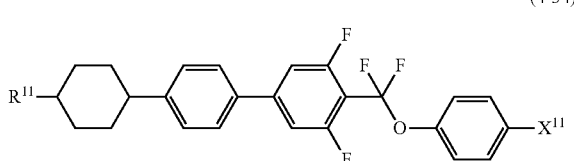

(4-35) 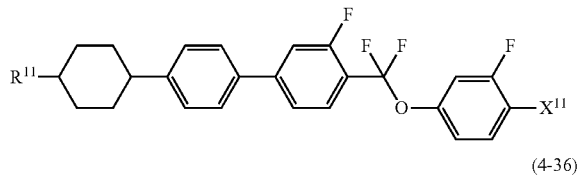
(4-36) 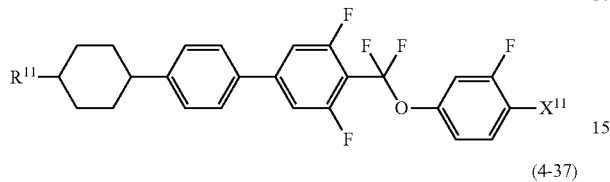
(4-37) 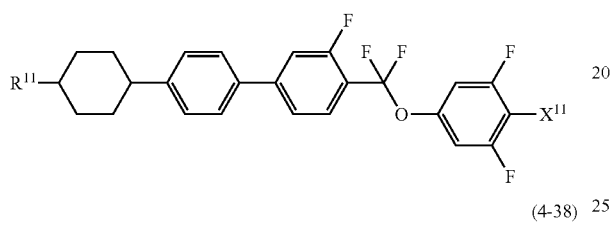
(4-38) 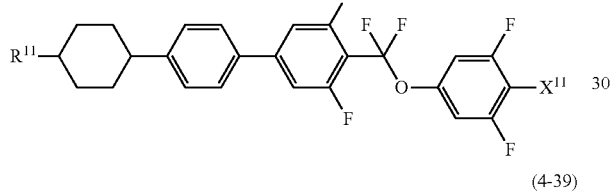
(4-39) 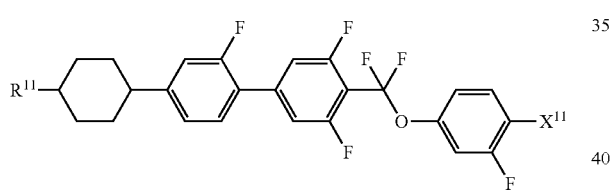
(4-40) 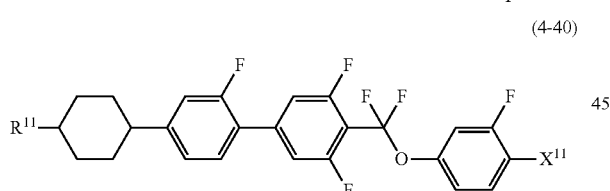
(4-41) 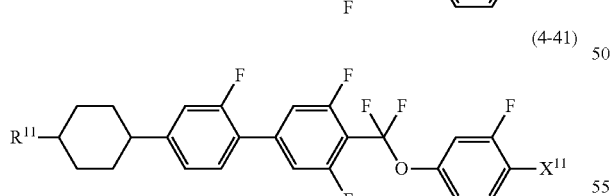
(4-42) 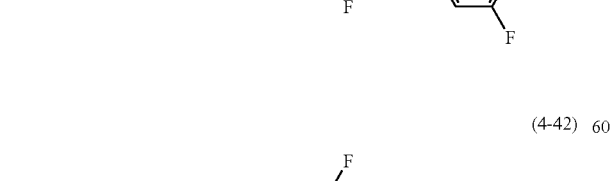
(4-43) 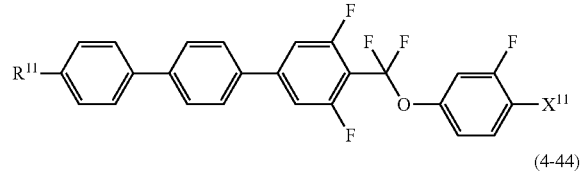
(4-44) 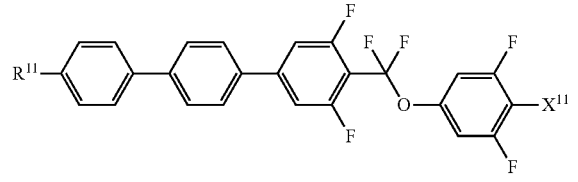
(4-45) 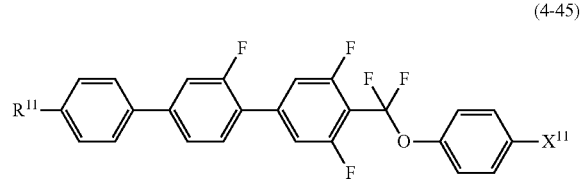
(4-46) 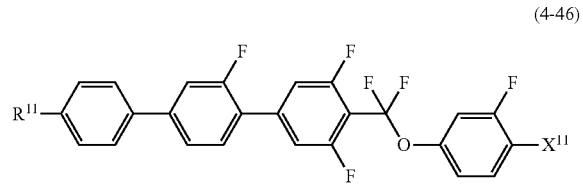
(4-47) 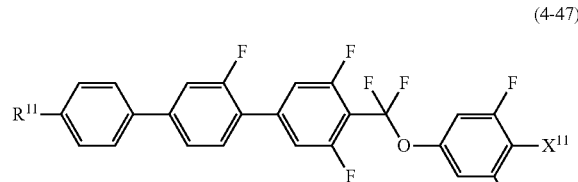
(4-48) 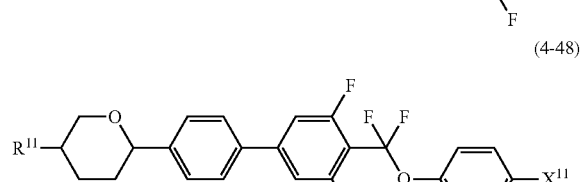
(4-49) 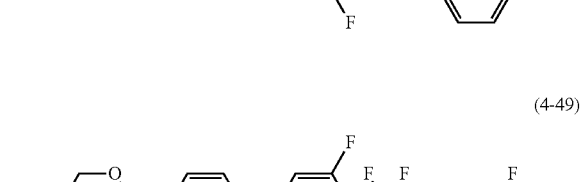
(4-50) 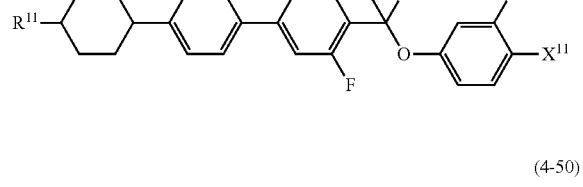

-continued (4-51)
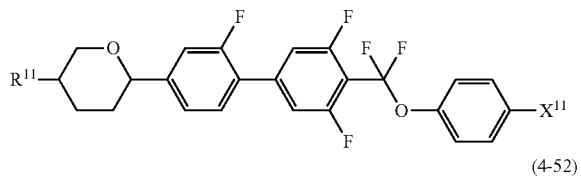

(4-52)
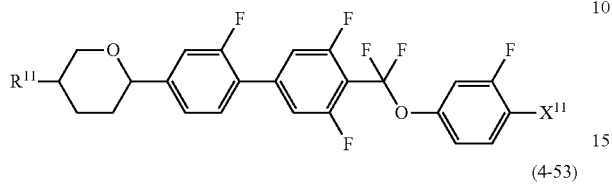

(4-53)
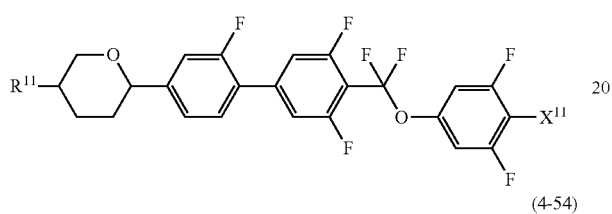

(4-54)
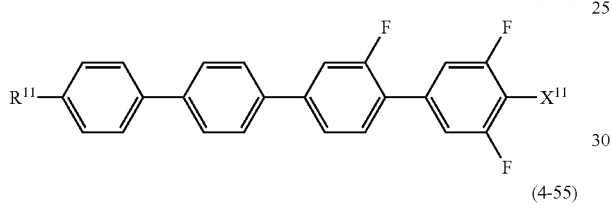

(4-55)
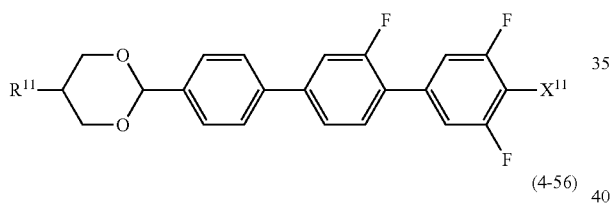

(4-56)
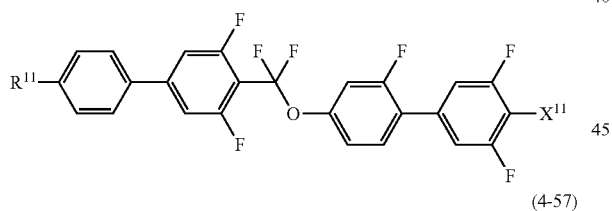

(4-57)
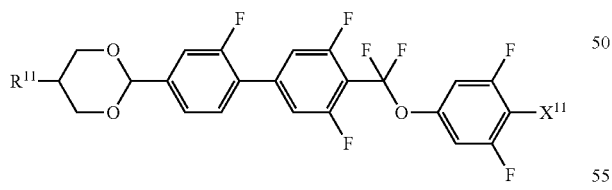

In the compounds (component B), $R^{11}$ and $X^{11}$ are defined in a manner identical with the definitions in formulas (2) to (4) described in item 8.

Component B has the positive dielectric anisotropy and a superb stability to heat, light and so forth, and therefore is used when preparing a composition for the TFT mode or the PSA mode. A content of component B is suitably in the range of approximately 1 to approximately 99% by weight, preferably, in the range of approximately 10 to approximately 97% by weight, and further preferably, in the range of approximately 40 to approximately 95% by weight, based on the total weight of the composition. The viscosity of the composition can be adjusted by further adding compounds (12) to (14) (component E) thereto.

Component C includes compound (5) in which a right-terminal group is —C≡N or —C≡C—C≡N. Preferred examples of component C include compounds (5-1) to (5-64).

(5-1)
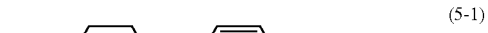

(5-2)

(5-3)
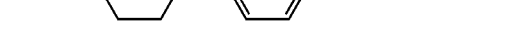

(5-4)
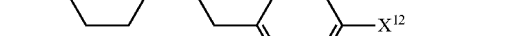

(5-5)
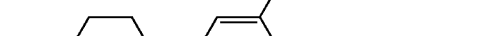

(5-6)

(5-7)

(5-8)

(5-9)

(5-10)

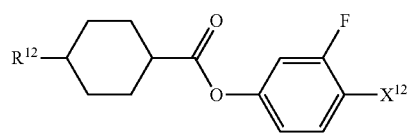 (5-11)
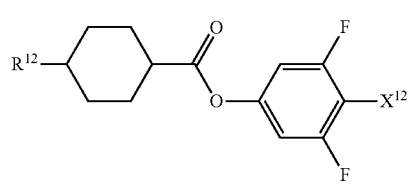 (5-12)
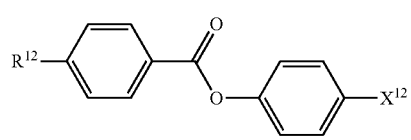 (5-13)
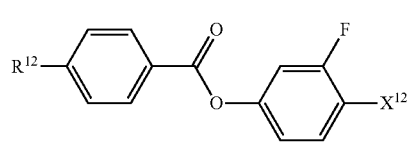 (5-14)
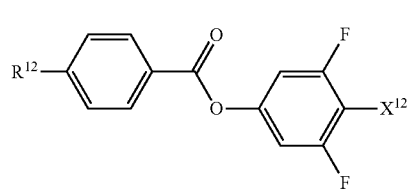 (5-15)
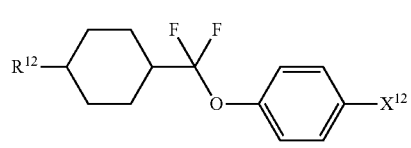 (5-16)
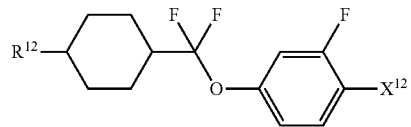 (5-17)
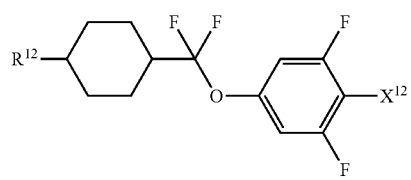 (5-18)
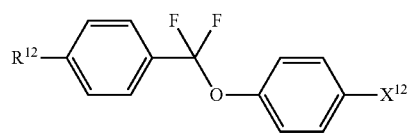 (5-19)
 (5-20)
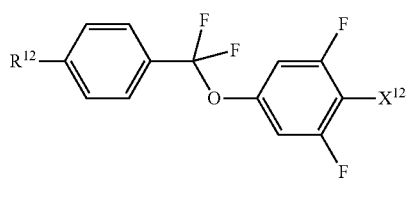 (5-21)
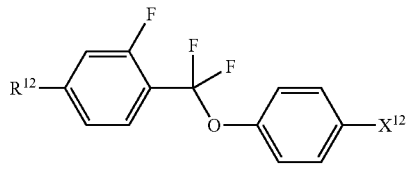 (5-22)
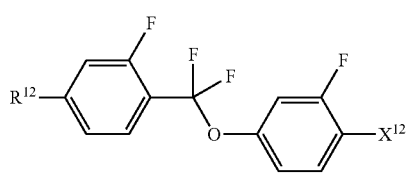 (5-23)
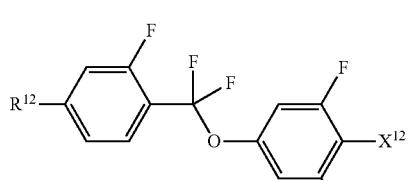 (5-24)
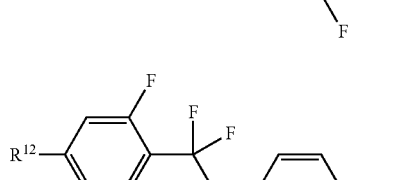 (5-25)
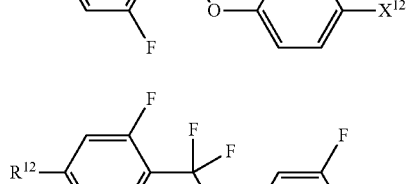 (5-26)
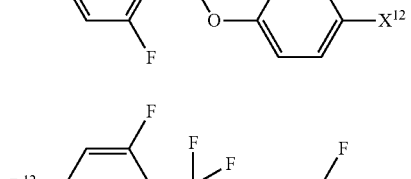 (5-27)
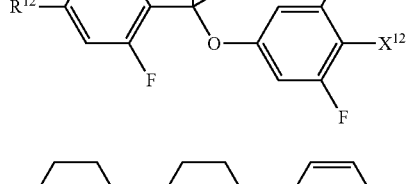 (5-28)
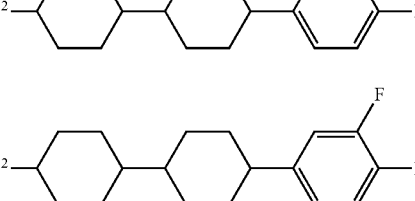 (5-29)

-continued
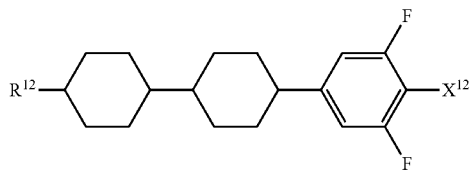 (5-30)
 (5-31)
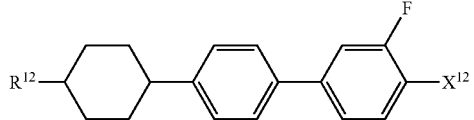 (5-32)
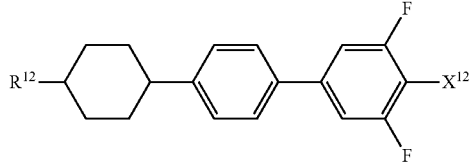 (5-33)
 (5-34)
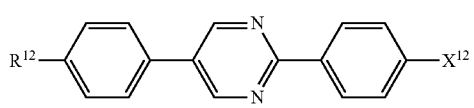 (5-35)
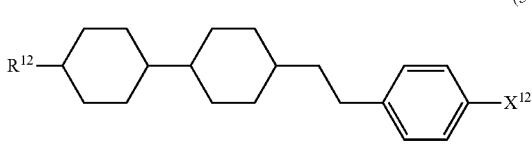 (5-36)
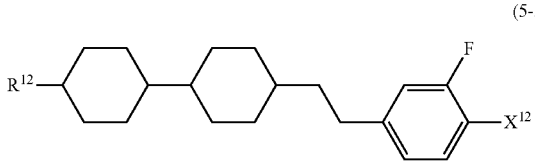 (5-37)
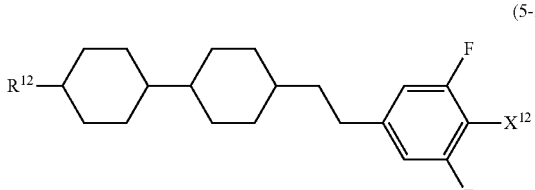 (5-38)
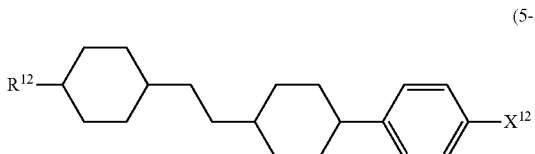 (5-39)
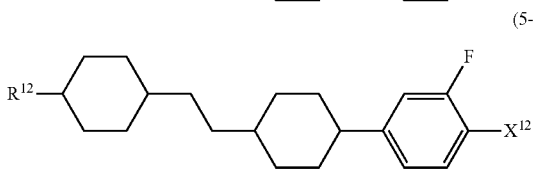 (5-40)
-continued
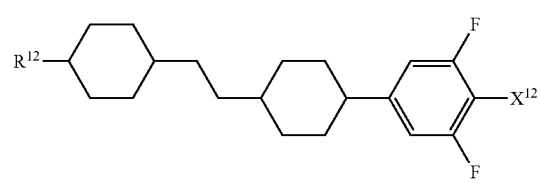 (5-41)
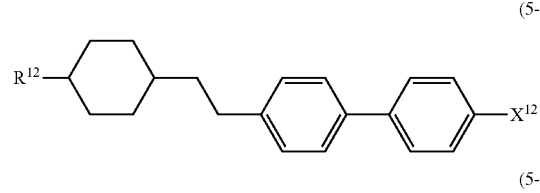 (5-42)
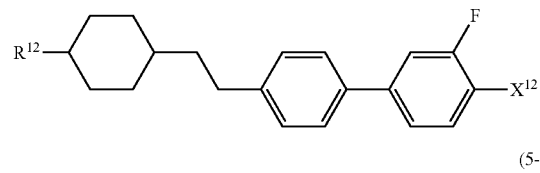 (5-43)
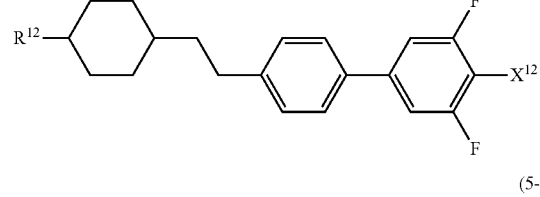 (5-44)
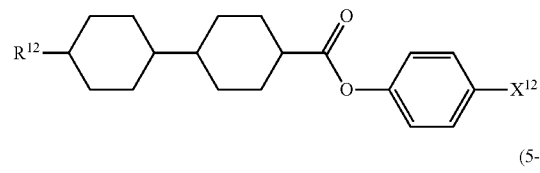 (5-45)
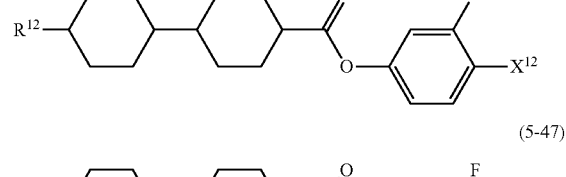 (5-46)
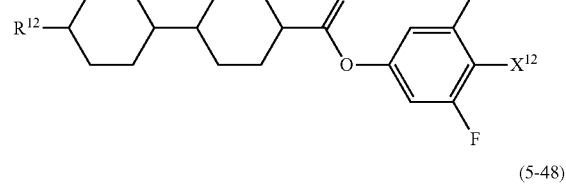 (5-47)
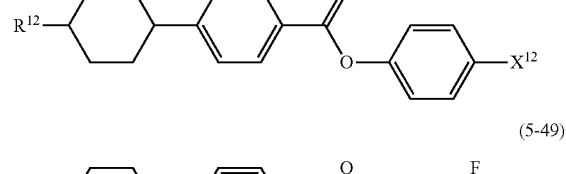 (5-48)
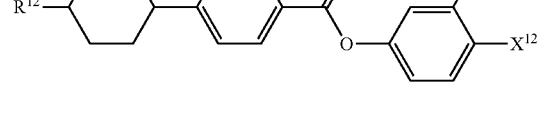 (5-49)

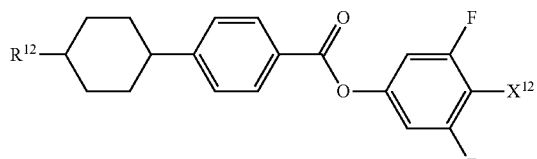
(5-50)

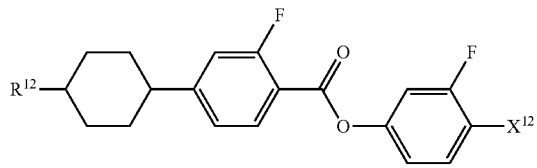
(5-51)

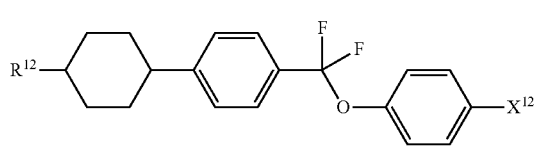
(5-52)

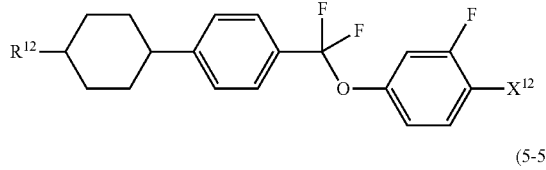
(5-53)

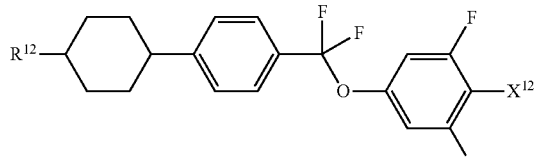
(5-54)

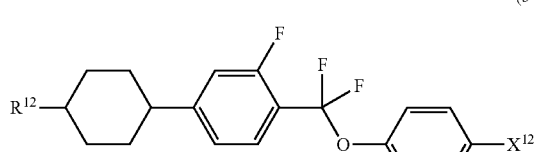
(5-55)

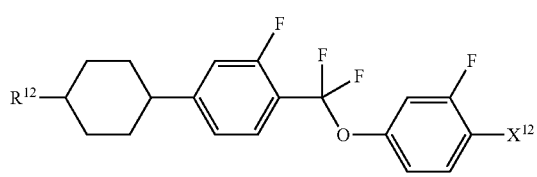
(5-56)

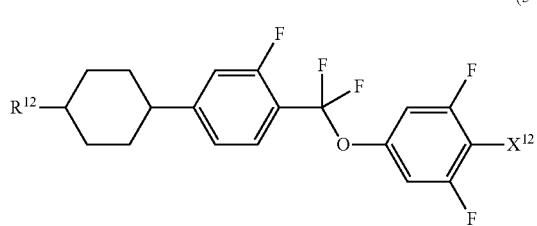
(5-57)

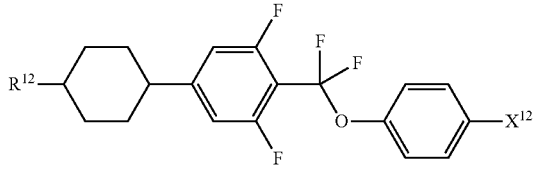
(5-58)

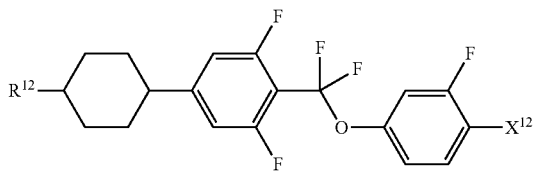
(5-59)

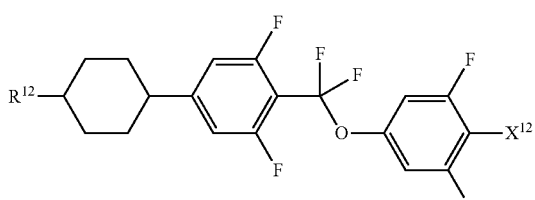
(5-60)

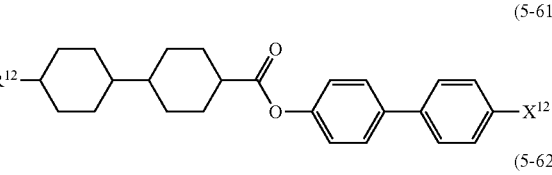
(5-61)

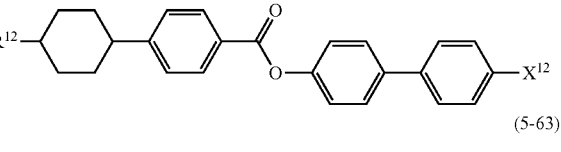
(5-62)

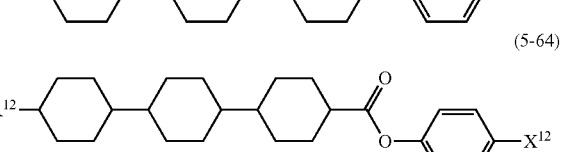
(5-63)

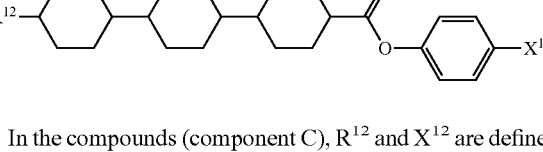
(5-64)

In the compounds (component C), $R^{12}$ and $X^{12}$ are defined in a manner identical with the definitions in formula (5) described in item 9.

Component C has a large value of positive dielectric anisotropy, and therefore is mainly used when preparing a composition for the STN mode, the TN mode or the PSA mode. The dielectric anisotropy of the composition can be increased by adding the component C thereto. Component C is effective in extending the temperature range of the liquid crystal phase, adjusting the viscosity or adjusting optical anisotropy. Component C is useful also for adjustment of a voltage-transmittance curve of the device.

When a composition for the STN mode or the TN mode is prepared, a content of component C is preferably in the range of approximately 1 to approximately 99% by weight, preferably, in the range of approximately 10 to approximately 97% by weight, and further preferably, in the range of approximately 40 to approximately 95% by weight, based on the total weight of the composition. The temperature range of the liquid crystal phase, the viscosity, the optical anisotropy, the dielectric anisotropy or the like of the composition can be adjusted by adding component E thereto.

Component D includes compounds (6) to (12). The compounds have a benzene ring in which lateral positions are replaced by two halogen atoms, such as 2,3-difluoro-1,4-phenylene. Preferred examples of component D include compounds (6-1) to (6-8), compounds (7-1) to (7-17), compound (8-1), compounds (9-1) to (9-3), compounds (10-1) to (10-12), compounds (11-1) to (11-3) and compounds (12-1) to (12-3).

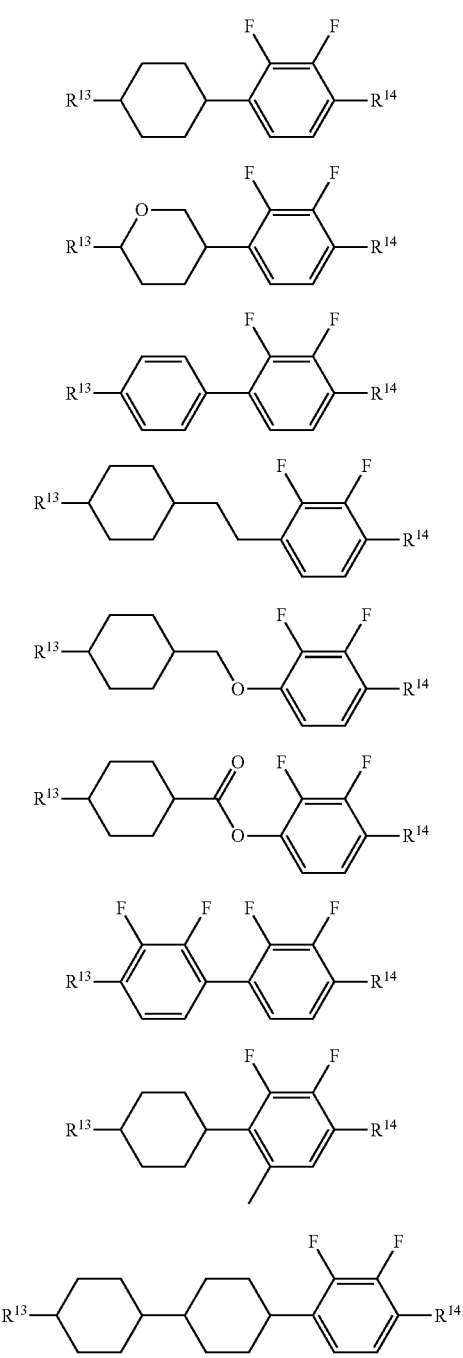

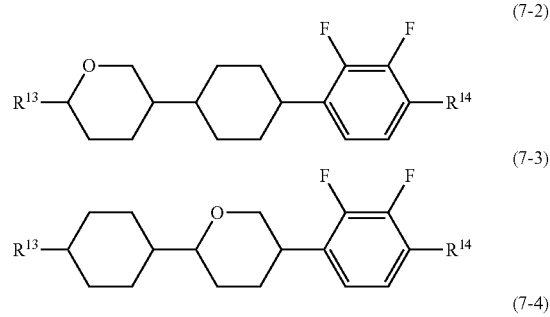
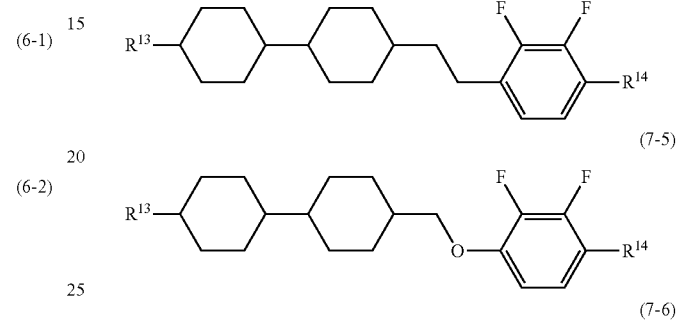
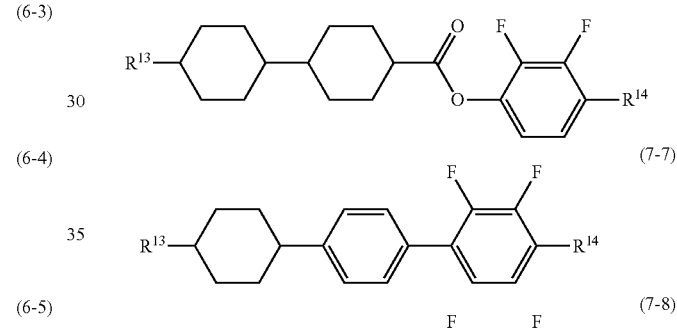
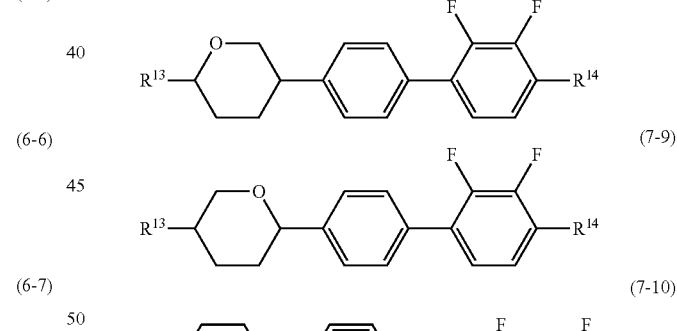
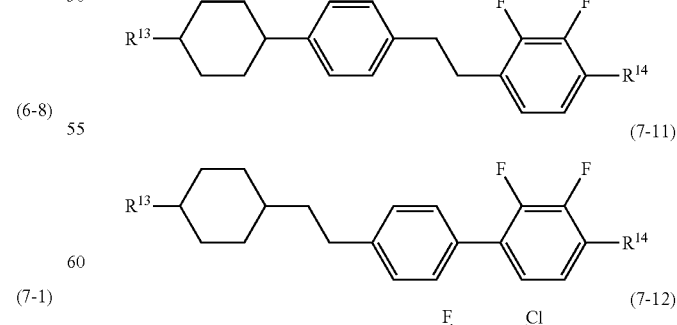

(7-13) 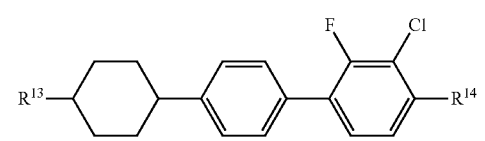
(7-14) 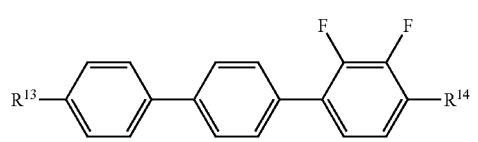
(7-15) 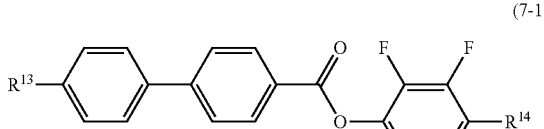
(7-16) 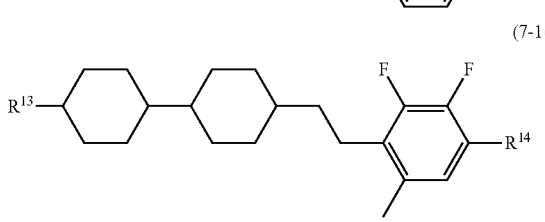
(7-17) 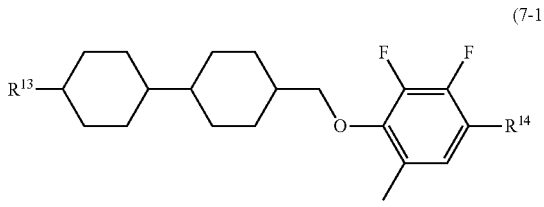
(8-1) 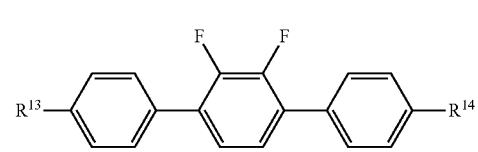
(9-1) 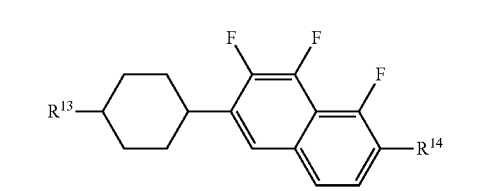
(9-2) 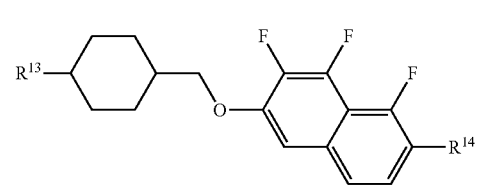
(9-3) 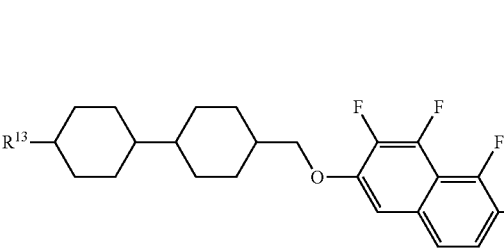
(10-1) 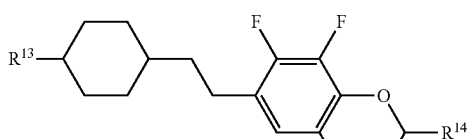
(10-2) 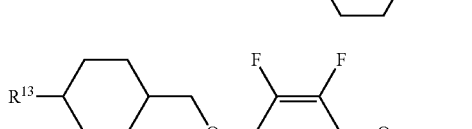
(10-3) 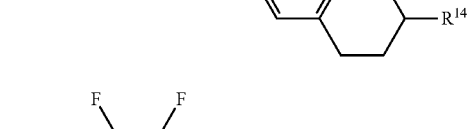
(10-4) 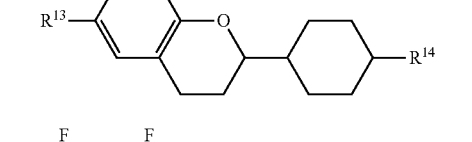
(10-5) 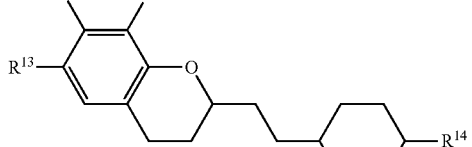
(10-6) 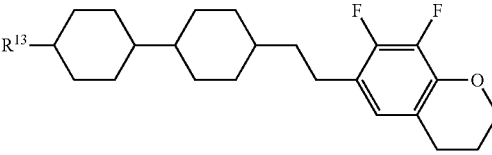
(10-7) 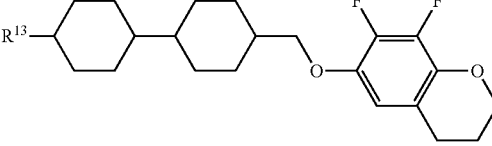
(10-8) 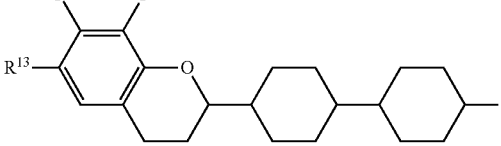

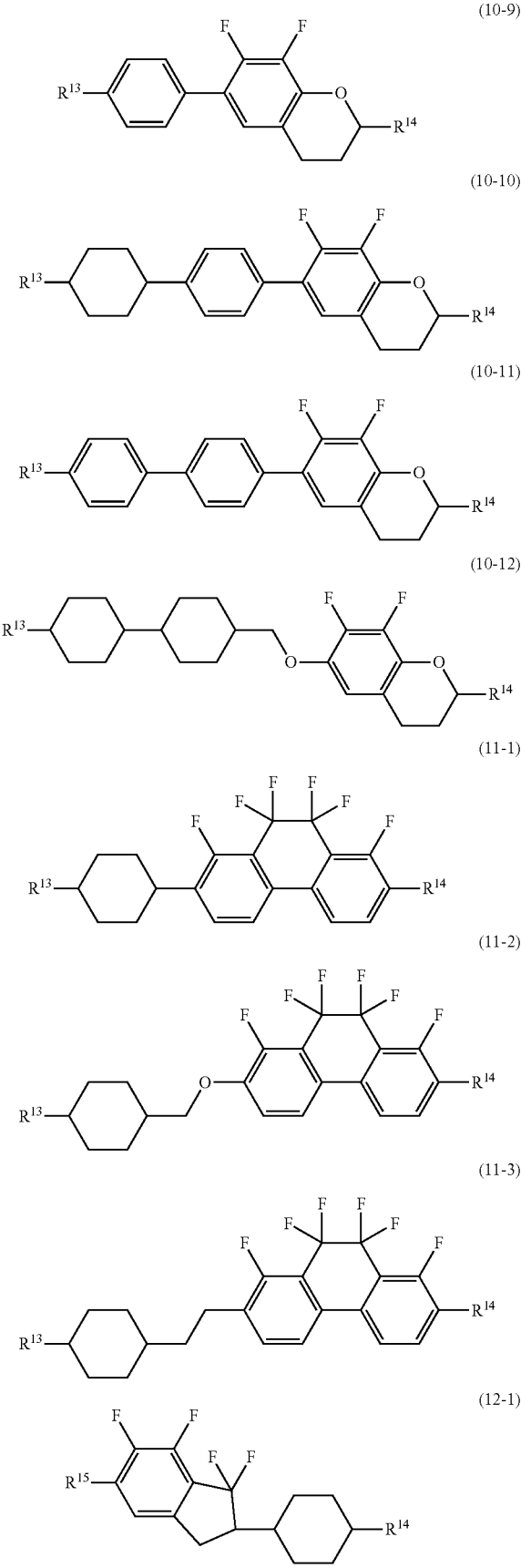

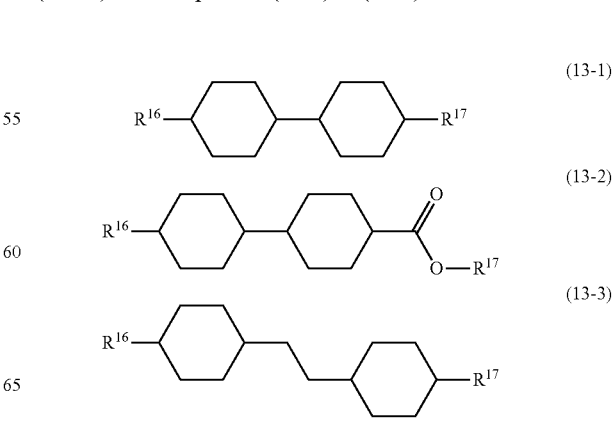

In the compounds (component D), $R^{13}$, $R^{14}$ and $R^{15}$ are defined in a manner identical with the definitions in formulas (6) to (12) described in item 10.

Component D includes a compound having a negative dielectric anisotropy. Component D is mainly used when preparing a composition for the VA mode or the PSA mode. Among types of component D, compound (6) is a bicyclic compound, and therefore is effective mainly in adjusting the viscosity, adjusting the optical anisotropy or adjusting the dielectric anisotropy. Compounds (7) and (8) are a tricyclic compound, and therefore effective in increasing the maximum temperature, the optical anisotropy or the dielectric anisotropy. Compounds (9) to (12) are effective in increasing the dielectric anisotropy.

When a composition for the VA mode or the PSA mode is prepared, the content of component D is preferably approximately 40% by weight or more, and further preferably, in the range of approximately 50 to approximately 95% by weight, based on the total weight of the composition. When component D is added to a composition having the positive dielectric anisotropy, a content of component D is preferably approximately 30% or less based on the total weight of the composition. When component D is added, an elastic constant of the composition and a voltage-transmittance curve of the device can be adjusted.

Component E includes a compound in which two terminal groups are alkyl or the like. Preferred examples of component E include compounds (13-1) to (13-11), compounds (14-1) to (14-19) and compounds (15-1) to (15-7).

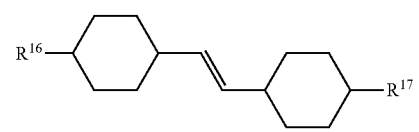 (13-4)
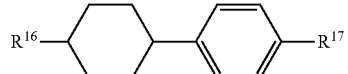 (13-5)
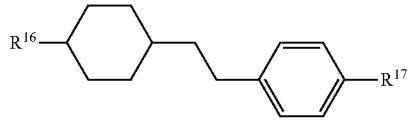 (13-6)
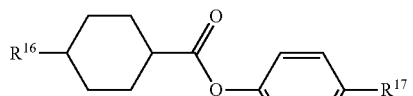 (13-7)
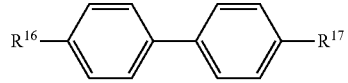 (13-8)
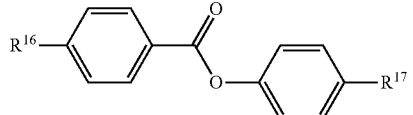 (13-9)
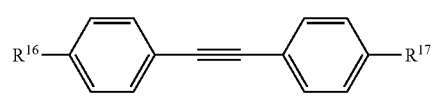 (13-10)
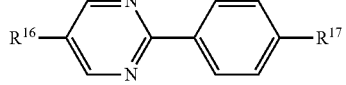 (13-11)
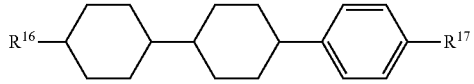 (14-1)
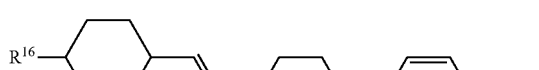 (14-2)
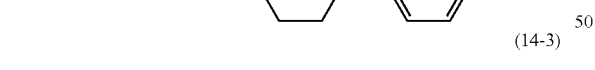 (14-3)
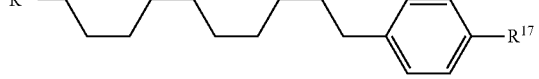 (14-4)
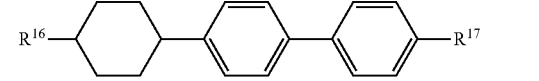 (14-5)
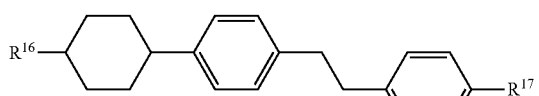 
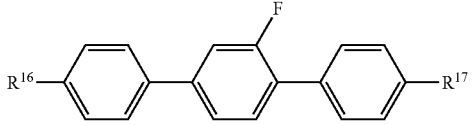 (14-6)
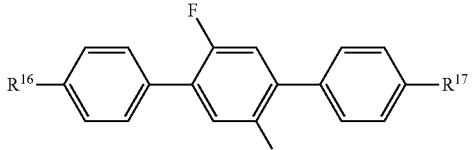 (14-7)
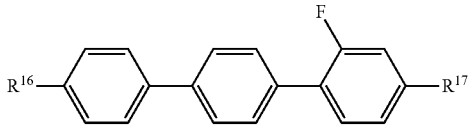 (14-8)
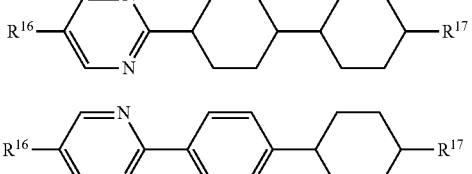 (14-9)
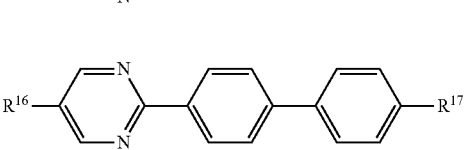 (14-10)
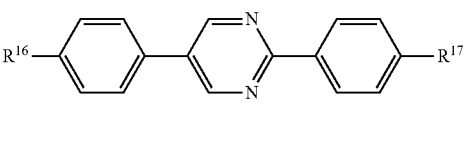 (14-11)
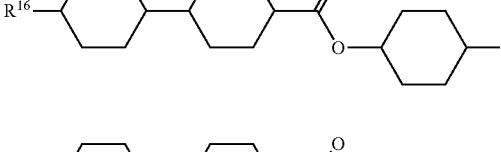 (14-12)
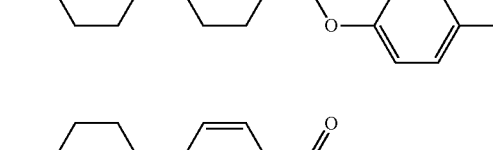 (14-13)
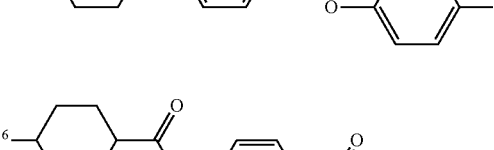 (14-14)
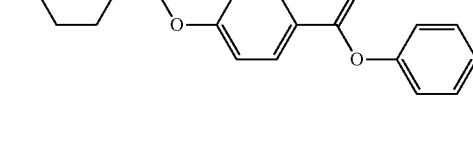 (14-15)
(14-16)

-continued (14-17)
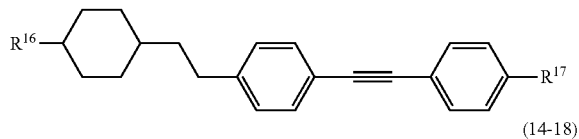

(14-18)
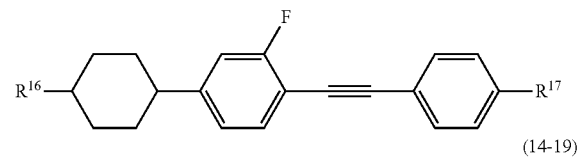

(14-19)
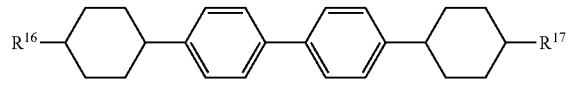

(15-1)
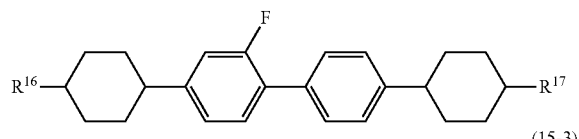

(15-2)
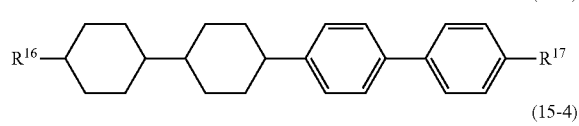

(15-3)
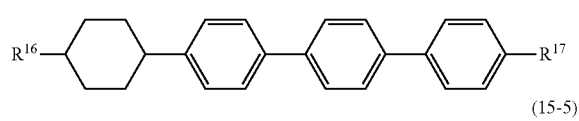

(15-4)
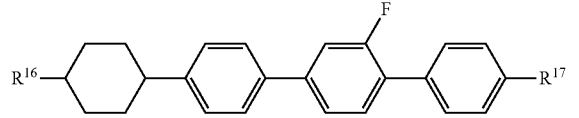

(15-5)
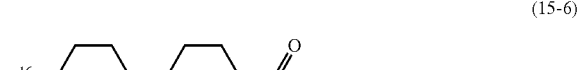

(15-6)
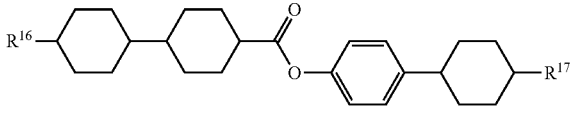

-continued (15-7)
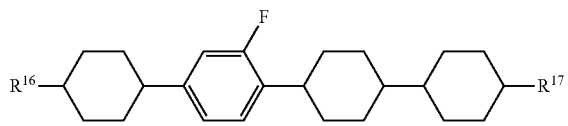

In the compounds (component E), $R^{16}$ and $R^{17}$ are defined in a manner identical with the definitions in formulas (13) to (15) described in item 11.

Component E has a small absolute value of dielectric anisotropy, and therefore is a compound close to neutrality. Compound (13) is effective mainly in adjusting the viscosity or the optical anisotropy. Compound (14) and (15) are effective in extending the temperature range of the nematic phase by increasing the maximum temperature, or in adjusting the optical anisotropy.

When a content of component E is increased, the viscosity of a composition decreases, but the dielectric anisotropy also decreases. Thus, as long as a desired value of threshold voltage of the device is met, the content is preferably as large as possible. Therefore, when a composition for the VA mode or the PSA mode is prepared, the content of component E is preferably approximately 30% by weight or more, and further preferably, approximately 40% by weight or more, based on the total weight of the composition.

Composition (1) is prepared by a method for dissolving necessary components at a high temperature, or the like. According to an application, an additive may be added to the composition. Examples of the additive include an optically active compound, a polymerizable compound, a polymerization initiator, an antioxidant, an ultraviolet light absorber, a light stabilizer, a heat stabilizer and a defoaming agent. Such additives are well known to those skilled in the art, and are described in literature.

Composition (1) may further contain at least one optically active compound. A publicly known chiral dopant can be added as the optically active compound. The chiral dopant is effective in inducing a helical structure in liquid crystal molecules to give a necessary twist angle, thereby preventing a reverse twist. Preferred examples of the chiral dopant include compounds (Op-1) to (Op-18) below. In compound (Op-18), ring J is 1,4-cyclohexylene or 1,4-phenylene, and $R^{24}$ is alkyl having 1 to 10 carbons.

(Op-1)
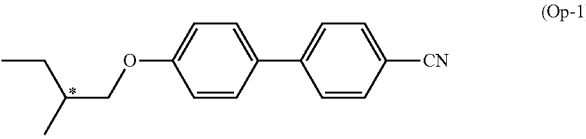

(Op-2)
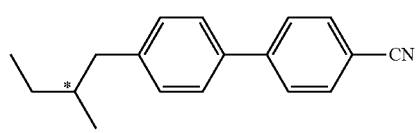

(Op-3)
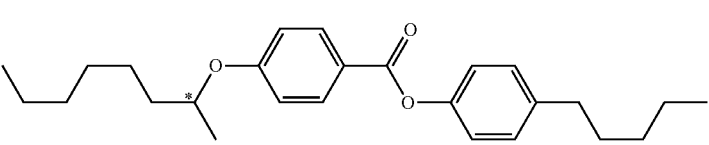

-continued
(Op-4)
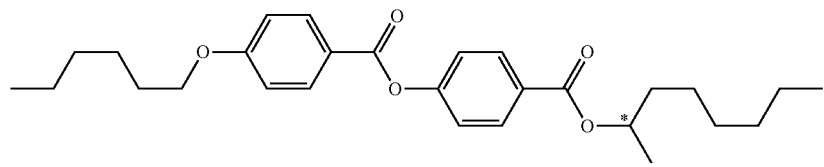
(Op-5)
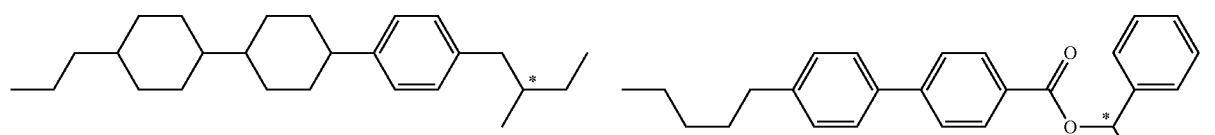
(Op-6)
(Op-7)
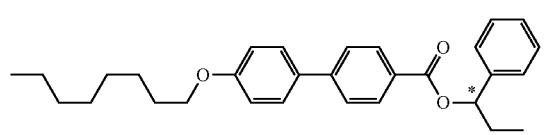
(Op-8)
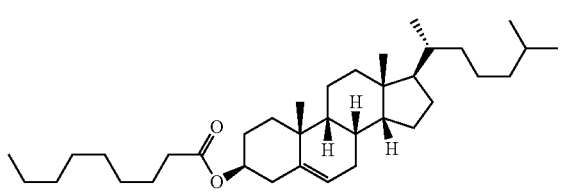
(Op-9)
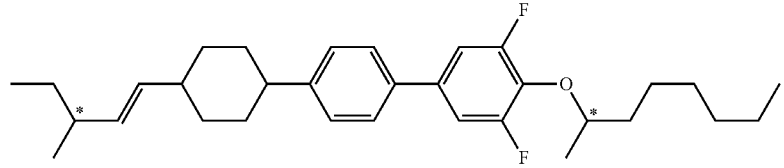
(Op-10)
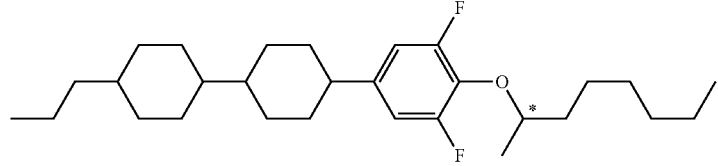
(Op-11)
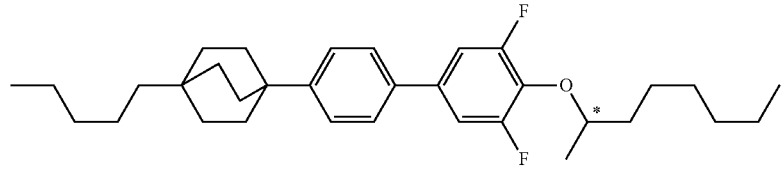
(Op-12)
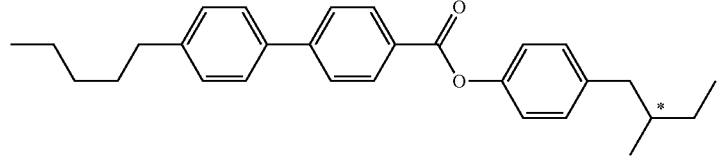
(Op-13)
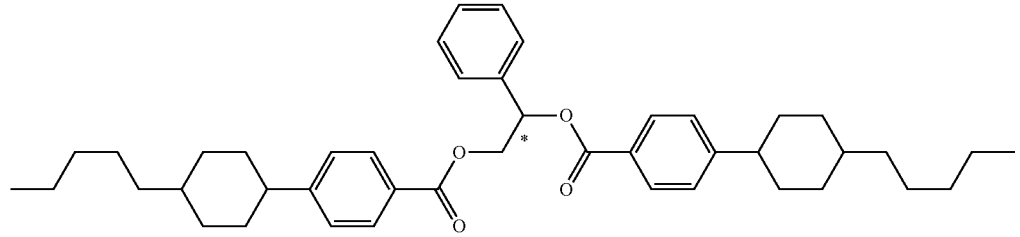

(Op-14) (Op-15)

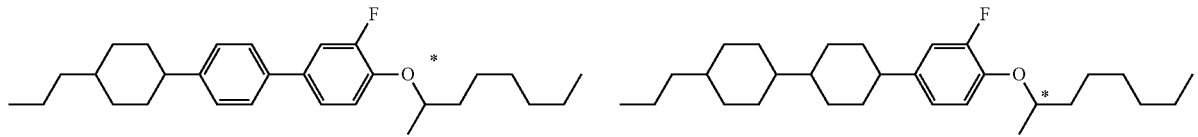

(Op-16) (Op-17)

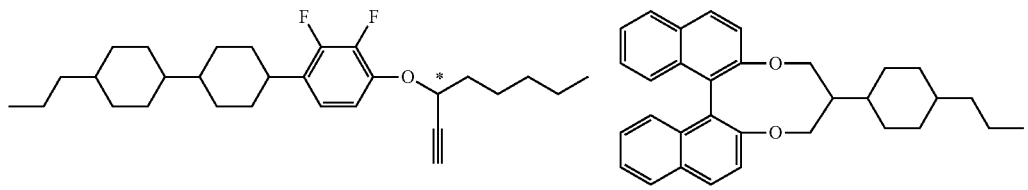

(Op-18)

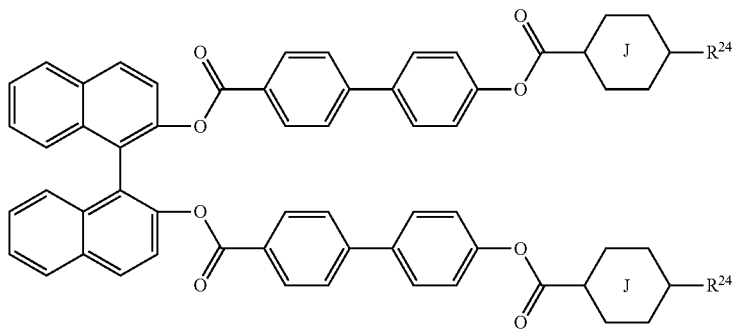

In composition (1), a helical pitch is adjusted by adding such an optically active compound. The helical pitch is preferably adjusted to the range of approximately 40 to approximately 200 micrometers in a composition for the TFT mode and the TN mode. The helical pitch is preferably adjusted to the range of approximately 6 to approximately 20 micrometers in a composition for the STN mode. In the case of a composition for the BTN mode, the helical pitch is preferably adjusted to the range of approximately 1.5 to approximately 4 micrometers. Two or more optically active compounds may be added for the purpose of adjusting temperature dependence of the helical pitch.

Composition (1) can also be used for the PSA mode by adding the polymerizable compound. Examples of the polymerizable compound include acrylate, methacrylate, a vinyl compound, a vinyloxy compound, propenyl ether, an epoxy compound (oxirane, oxetane) and vinyl ketone. Preferred examples include compounds (M-1) to (M-12) below. The polymerizable compound is polymerized by irradiation with ultraviolet light or the like. The compound may be polymerized in the presence of a suitable initiator such as a photopolymerization initiator. Suitable conditions for polymerization, suitable types of the initiator and suitable amounts thereof are known to those skilled in the art and are described in literature.

In compounds (M-1) to (M-12), $R^{20}$ is hydrogen or methyl; s and v are independently 0 or 1; t and u are independently an integer from 1 to 10, and $L^{21}$, $L^{22}$, $L^{23}$, $L^{24}$, $L^{25}$ and $L^{26}$ are independently hydrogen or fluorine.

(M-1) (M-2)

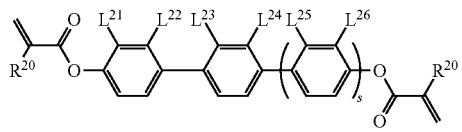 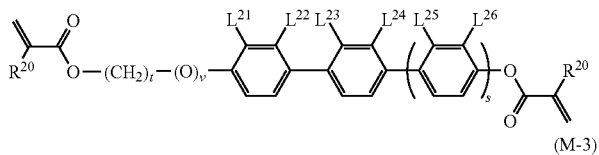

(M-3)

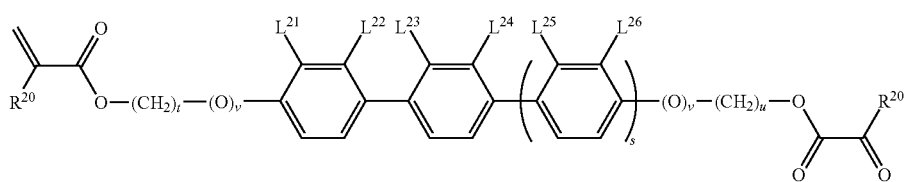

-continued
(M-4)
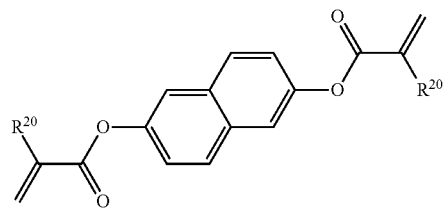
(M-5)
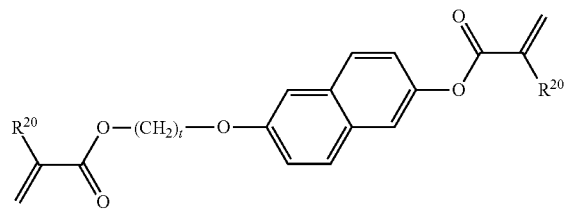
(M-6)
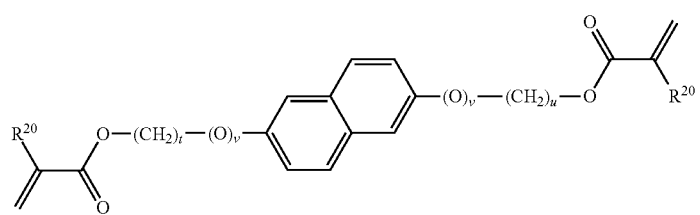
(M-7)
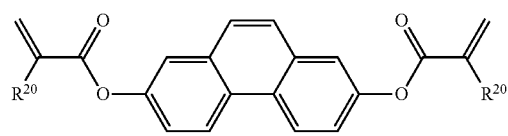
(M-8)
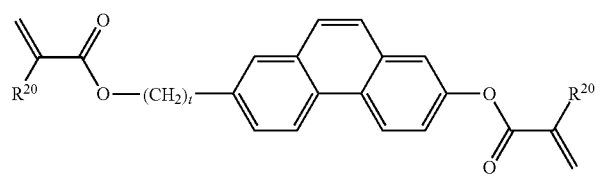
(M-9)
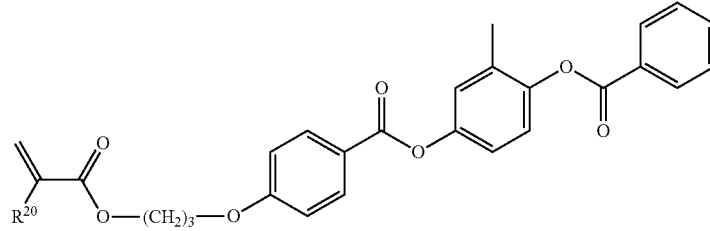
(M-10)
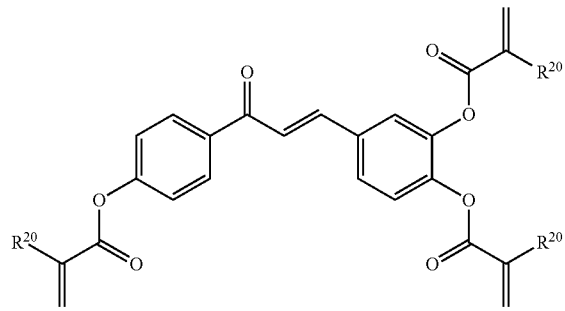
(M-11)
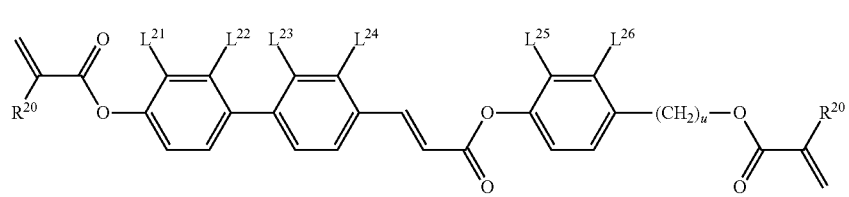

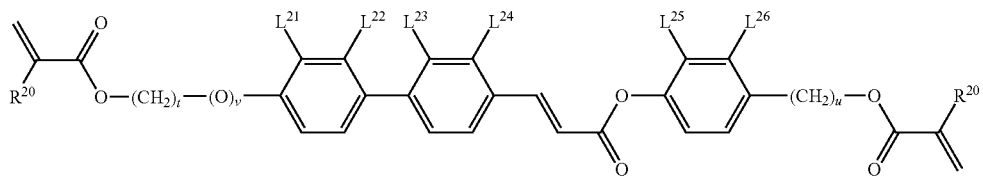

(M-12)

The antioxidant is effective for maintaining a large voltage holding ratio. Preferred examples of the antioxidant include compounds (AO-1) and (AO-2) below; Irganox 415, Irganox 565, Irganox 1010, Irganox 1035, Irganox 3114 and Irganox 1098 (trade names: BASF SE). The ultraviolet light absorber is effective for preventing a decrease in the maximum temperature. Preferred examples of the ultraviolet light absorber include a benzophenone derivative, a benzoate derivative and a triazole derivative. Specific examples include compounds (AO-3) and (AO-4) below; Tinuvin329, Tinuvin P, Tinuvin 326, Tinuvin 234, Tinuvin 213, Tinuvin 400, Tinuvin 328 and Tinuvin 99-2 (trade names: BASF SE); and 1,4-diazabicyclo [2.2.2]octane (DABCO).

A light stabilizer such as amine having steric hindrance is preferred for maintaining the large voltage holding ratio. Preferred examples of the light stabilizer include compounds (AO-5) and (AO-6) below; Tinuvin 144, Tinuvin 765 and Tinuvin 770DF (trade names: BASF SE). The heat stabilizer is also effective for maintaining the large voltage holding ratio, and preferred examples include Irgafox 168 (trade name: BASF SE). The defoaming agent is effective for preventing foam formation. Preferred examples of the defoaming agent include dimethyl silicone oil and methylphenyl silicone oil.

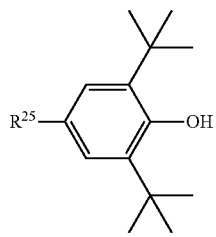

(AO-1)

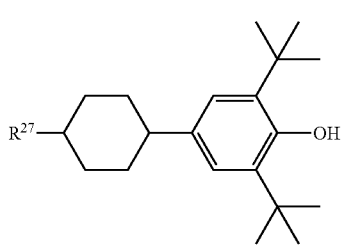

(AO-2)

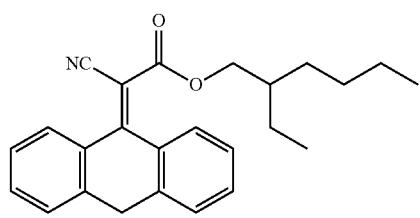

(AO-3)

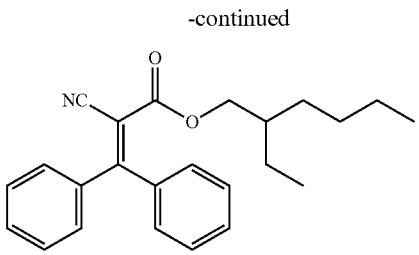

(AO-4)

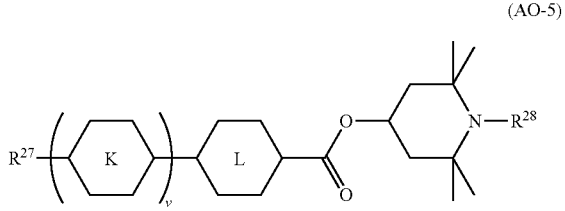

(AO-5)

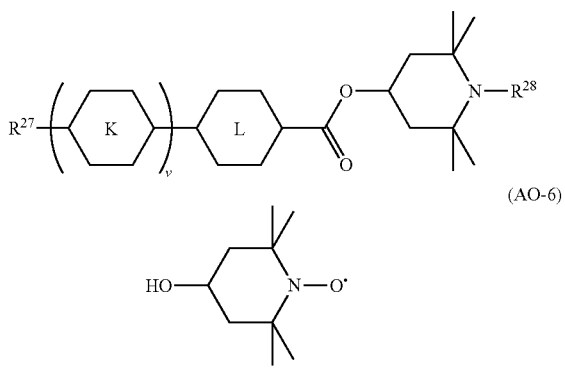

(AO-6)

In compound (AO-1), $R^{25}$ is alkyl having 1 to 20 carbons, alkoxy having 1 to 20 carbons, —COOR$^{26}$ or —CH$_2$CH$_2$COOR$^{26}$; and R$^{26}$ is alkyl having 1 to 20 carbons. In compounds (AO-2) and (AO-5), $R^{27}$ is alkyl having 1 to 20 carbons. In compound (AO-5), ring K and ring L are independently 1,4-cyclohexylene or 1,4-phenylene, v is 0, 1 or 2, and $R^{28}$ is hydrogen, methyl or O$^{•}$.

If a dichroic dye of a merocyanine type, a stylyl type, an azo type, an azomethine type, an azoxy type, a quinophthalone type, an anthraquinone type, a tetrazine type or the like is added, composition (1) can be used for a guest host (GH) mode.

In composition (1), the maximum temperature can be adjusted to approximately 70° C. or higher and the minimum temperature can be adjusted to approximately −10° C. or lower by suitably adjusting a kind and a ratio of component compounds, and therefore the temperature range of the nematic phase is wide. Accordingly, a liquid crystal display device including the composition can be used in the wide temperature range.

In composition (1), the optical anisotropy can be adjusted to the range of approximately 0.10 to approximately 0.13 or to the range of approximately 0.05 to approximately 0.18 by suitably adjusting the kind and the ratio of component compounds. In a similar manner, the dielectric anisotropy can be adjusted to the range of approximately −5.0 to approximately −2.0. Preferred dielectric anisotropy is in the range of approximately −4.5 to approximately −2.5. Composition (1) having the dielectric anisotropy in the range can be suitably used for a liquid crystal display device that operates in the IPS mode, the VA mode or the PSA mode.

3. Liquid Crystal Display Device

Composition (1) can be used for an AM device. The composition can also be used for a PM device. The composition can be used for an AM device and a PM device each having a mode such as PC, TN, STN, ECB, OCB, IPS, FFS, VA, PSA or FPA. Use for an AM device having the TN, OCB, IPS or FFS mode is particularly preferred. In an AM device having the IPS mode or FFS mode, alignment of liquid crystal molecules in a state in which no voltage is applied may be parallel or perpendicular to a panel substrate. The devices may be of a reflective type, a transmissive type or a transflective type. Use for the transmissive device is preferred. The composition can also be used for an amorphous silicon-TFT device or a polycrystal silicon-TFT device. The composition can also be used for a nematic curvilinear aligned phase (NCAP) mode device prepared by microencapsulating the composition, and for a polymer dispersed (PD) mode device in which a three-dimensional network-polymer is formed in the composition.

Composition (1) has the negative dielectric anisotropy, and therefore can be suitably used for a liquid crystal display device that has an operating mode such as the VA mode, the IPS mode or the PSA mode, and is driven by an AM mode. The composition can be particularly suitably used for a liquid crystal display device that has the VA mode and driven by the AM mode.

In a liquid crystal display device that operates in the TN mode, the VA mode or the like, a direction of an electric field is perpendicular to a direction of a liquid crystal layer. On the other hand, in a liquid crystal display device that operates in the IPS mode or the like, the direction of the electric field direction is parallel to the direction of the liquid crystal layer. A structure of a liquid crystal display device that operates in the VA mode is reported by K. Ohmuro, S. Kataoka, T. Sasaki and Y. Koike, SID '97 Digest of Technical Papers, 28, 845 (1997). A structure of a liquid crystal display device that operates in the IPS mode is reported in WO 91/10936 A (family: U.S. Pat. No. 5,576,867 B).

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted to, limit the scope of the invention.

EXAMPLES

The invention will be described in greater detail by way of Examples. The invention is not restricted by the Examples.

1-1. Example of Compound (1)

Compound (1) was prepared by procedures as described below. A prepared compound was identified by a method such as NMR analysis. Physical properties of the compound were measured by methods as described below.

NMR Analysis

As a measuring apparatus, DRX-500 (made by Bruker BioSpin Corporation) was used. In $^1$H-NMR measurement, a sample was dissolved in a deuterated solvent such as $CDCl_3$, and measurement was carried out under conditions of room temperature, 500 MHz and 16 times of accumulation. Tetramethylsilane was used as an internal standard. In $^{19}$F-NMR measurement, measurement was carried out under conditions of 24 times of accumulation using $CFCl_3$ as an internal standard. In the explanation of nuclear magnetic resonance spectra, s, d, t, q, quin, sex, m stand for a singlet, a doublet, a triplet, a quartet, a quintet, a sextet and a multiplet, respectively, and br means being broad.

Measurement Sample

In measuring a phase structure and a transition temperature, a liquid crystal compound itself was used as a sample. In measuring physical properties such as a maximum temperature of a nematic phase, viscosity, optical anisotropy and dielectric anisotropy, a composition prepared by mixing the compound with a base liquid crystal was used as a sample.

In the case where a sample prepared by mixing the compound with the base liquid crystal was used, measurement was carried out according to the method described below. A sample was prepared by mixing 15% by weight of the compound and 85% of the base liquid crystal. An extrapolated value was calculated from a measured value of the sample according to an extrapolation method based on an equation below, and the value was described. [Extrapolated value]= (100×[measured value of a sample]−[% of base liquid crystal]×[measured value of the base liquid crystal])/[% of the compound].

When a crystal (or a smectic phase) precipitated at 25° C. even at the ratio of the compound to the base liquid crystal, a ratio of the compound to the base liquid crystal was changed in the order of (10% by weight: 90% by weight), (5% by weight: 95% by weight) and (1% by weight: 99% by weight). Physical properties of a sample were measured at a ratio in which the crystal (or the smectic phase) did not precipitate at 25° C. In addition, unless otherwise noted, the ratio of the compound to the base liquid crystal is 15% by weight: 85% by weight.

As the base liquid crystal, base liquid crystal (i) below was used. Ratios of components of base liquid crystal (i) are expressed in terms of weight percent (% by weight).

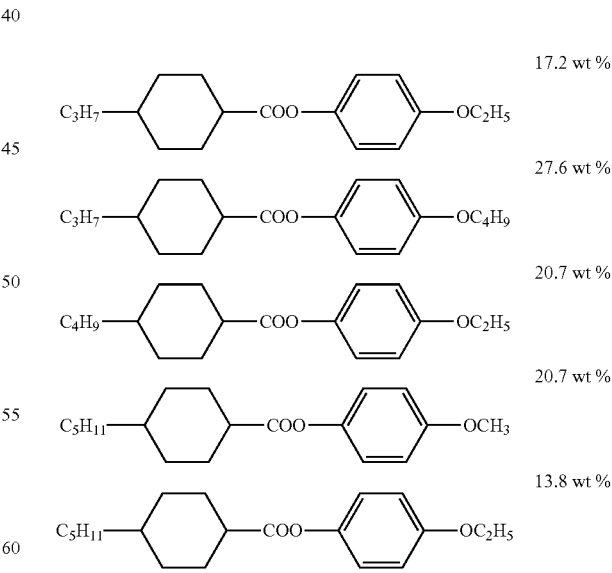

Measurement Method

Physical properties of a compound were measured according to the methods described below. Most of the measurement methods are applied as described in the Standard of the Japan Electronics and Information Technology Industries Association (hereinafter, abbreviated as JEITA) (JEITA EIAJ ED-2521A) discussed and established by JEITA, or modified thereon. No TFT was attached to a TN device used for measurement.

(1) Phase Structure

A sample was placed on a hot plate of a melting point apparatus (FP52 Hot Stage, made by Mettler-Toledo International Inc.) equipped with a polarizing microscope, and a state of a phase and a change thereof were observed with the polarizing microscope while the sample was heated at a rate of 3° C. per minute, and a kind of the phase was specified.

(2) Transition Temperature (° C.)

A sample was heated and then cooled at a rate of 3° C. per minute using a differential scanning calorimeter, DSC-7 System or Diamond DSC System, made by PerkinElmer, Inc. A starting point of an endothermic peak or an exothermic peak caused by a phase change of the sample was determined by extrapolation, and thus a transition temperature was determined. Temperature at which a compound undergoes transition from a solid to a liquid crystal phase such as the smectic phase and the nematic phase may be occasionally abbreviated as "minimum temperature of the liquid crystal phase." Temperature at which a compound undergoes transition from the liquid crystal phase to a liquid may be occasionally abbreviated as "clearing point."

The crystal was expressed as C. When kinds of the crystals were distinguishable, each of the crystals was expressed as $C_1$ or $C_2$. A smectic phase or a nematic phase was expressed as S or N. When smectic A phase, smectic B phase, smectic C phase or smectic F phase was distinguishable among the smectic phases, the phases were expressed as $S_A$, $S_B$, $S_C$ or $S_F$, respectively. The liquid (isotropic) was expressed as I. A transition temperature was expressed as "C 50.0 N 100.0 I," for example. The expression indicates that a transition temperature from the crystal to the nematic phase is 50.0° C., and a transition temperature from the nematic phase to the liquid is 100.0° C.

(3) Compatibility at a Low Temperature:

Samples in which the base liquid crystal and a compound were mixed for the compound to be 20% by weight, 15% by weight, 10% by weight, 5% by weight, 3% by weight and 1% by weight were prepared, and put in glass vials. After the glass vials were kept in freezers at −10° C. or −20° C. for a predetermined period of time, whether or not the crystal (or the smectic phase) precipitated was observed.

(4) Maximum Temperature of a Nematic Phase ($T_{NI}$ or NI; ° C.)

A sample was placed on a hot plate of a melting point apparatus equipped with a polarizing microscope and was heated at a rate of 1° C. per minute. Temperature when part of the sample began to change from a nematic phase to an isotropic liquid was measured. A higher limit of a temperature range of the nematic phase may be occasionally abbreviated as "maximum temperature." When the sample was a mixture of a compound and the base liquid crystal, the maximum temperature was expressed in terms of a symbol $T_{NI}$. When the sample was a mixture of a compound and component B and so forth, the maximum temperature was expressed in terms of a symbol NI.

(5) Minimum Temperature of a Nematic Phase ($T_C$; ° C.)

Samples each having a nematic phase were kept in freezers at temperatures of 0° C., −10° C., −20° C., −30° C. and −40° C. for 10 days, and then liquid crystal phases were observed. For example, when the sample maintained the nematic phase at −20° C. and changed to the crystal or the smectic phase at −30° C., $T_C$ was expressed as $T_C \le -20°$ C. A lower limit of the temperature range of the nematic phase may be occasionally abbreviated as "minimum temperature."

(6) Viscosity (bulk viscosity; η; measured at 20° C.; mPa·s)

Viscosity was measured using a cone-plate (E-type) rotational viscometer.

(7) Viscosity (Rotational Viscosity; γ1; Measured at 25° C.; mPa·s)

Measurement was carried out according to the method described in M. Imai et al., Molecular Crystals and Liquid Crystals, Vol. 259, p. 37 (1995). A sample was put in a VA device in which a distance (cell gap) between two glass substrates was 20 micrometers. Voltage was stepwise applied to the device in the range of 30 V to 50 V at an increment of 1 V. After a period of 0.2 second with no voltage application, voltage was repeatedly applied under the conditions of only one rectangular wave (rectangular pulse; 0.2 second) and no application (2 seconds). A peak current and a peak time of a transient current generated by the applied voltage were measured. A value of rotational viscosity was obtained from the measured values and calculation equation (8) on page 40 of the paper presented by M. Imai et al. As dielectric anisotropy necessary for the calculation, a value measured in a section of dielectric anisotropy described below was used.

(8) Optical Anisotropy (Refractive Index Anisotropy; Δn; Measured at 25° C.)

Measurement was carried out by an Abbe refractometer with a polarizing plate mounted on an ocular by using light at a wavelength of 589 nanometers. A surface of a main prism was rubbed in one direction, and then a sample was added dropwise onto the main prism. A refractive index (n∥) was measured when the direction of polarized light was parallel to the direction of rubbing. A refractive index (n⊥) was measured when the direction of polarized light was perpendicular to the direction of rubbing. A value of refractive index anisotropy was calculated from an equation: Δn=n∥−n⊥.

(9) Dielectric anisotropy (Δ∈; measured at 25° C.)

A value of dielectric anisotropy was calculated from an equation: Δ∈=∈∥−∈⊥. Dielectric constants (∈∥ and ∈⊥) were measured as described below.

1) Measurement of dielectric constant (∈∥): An ethanol (20 mL) solution of octadecyl triethoxysilane (0.16 mL) was applied to a well-cleaned glass substrate. After rotating the glass substrate with a spinner, the glass substrate was heated at 150° C. for 1 hour. A sample was put in a VA device in which a distance (cell gap) between two glass substrates was 4 micrometers, and the device was sealed with an ultraviolet-curable adhesive. Sine waves (0.5 V, 1 kHz) were applied to the device, and after 2 seconds, a dielectric constant (∈∥) in the major axis direction of liquid crystal molecules was measured.

2) Measurement of dielectric constant (∈⊥): A polyimide solution was applied to a well-cleaned glass substrate. After calcining the glass substrate, rubbing treatment was applied to the alignment film obtained. A sample was put in a TN device in which a distance (cell gap) between two glass substrates was 9 micrometers and a twist angle was 80 degrees. Sine waves (0.5 V, 1 kHz) were applied to the device, and after 2 seconds, a dielectric constant (∈⊥) in the minor axis direction of the liquid crystal molecules was measured.

(10) Elastic constant ($K_{11}$ and $K_{33}$; measured at 25° C.; pN)

Elastic Constant Measurement System Model EC-1 made by TOYO Corporation was used for measurement. A sample was put in a vertical alignment device in which a distance (cell gap) between two glass substrates was 20 micrometers. An electric charge of 20 V to 0 V was applied to the device, and electrostatic capacity and applied voltage were measured. Values of electrostatic capacity (C) and applied voltage (V)

were fitted to equation (2.98) and equation (2.101) on page 75 of the "Liquid Crystal Device Handbook (Ekisho Debaisu Handobukku, in Japanese)" (The Nikkan Kogyo Shimbun, Ltd.), and a value of elastic constant was obtained from equation (2.100).

(11) Threshold Voltage (Vth; Measured at 25° C.; V)

An LCD-5100 luminance meter made by Otsuka Electronics Co., Ltd. was used for measurement. A light source was a halogen lamp. A sample was put in a normally black mode VA device in which a distance (cell gap) between two glass substrates was 4 micrometers and a rubbing direction was antiparallel, and the device was sealed with an ultraviolet-curable adhesive. A voltage (60 Hz, rectangular waves) to be applied to the device was stepwise increased from 0 V to 20 V at an increment of 0.02 V. On the occasion, the device was irradiated with light from a direction perpendicular to the device, and an amount of light transmitted through the device was measured. A voltage-transmittance curve was prepared, in which the maximum amount of light corresponds to 100% transmittance and the minimum amount of light corresponds to 0% transmittance. A threshold voltage is a voltage at 10% transmittance.

(12) Voltage Holding Ratio (VHR-1; Measured at 25° C.; %)

A TN device used for measurement had a polyimide alignment film and a distance (cell gap) between two glass plates was 5 micrometers. A sample was put in the device, and then the device was sealed with an ultraviolet-curable adhesive. A pulse voltage (60 microseconds at 5 V) was applied to the TN device and the device was charged. A decaying voltage was measured for 16.7 milliseconds with a high-speed voltmeter, and area A between a voltage curve and a horizontal axis in a unit cycle was determined. Area B is an area without decay. A voltage holding ratio is a percentage of area A to area B.

(13) Voltage Holding Ratio (VI-IR-2; Measured at 80° C.; %)

A TN device used for measurement had a polyimide alignment film and a distance (cell gap) between two glass plates was 5 micrometers. A sample was put in the device, and then the device was sealed with an ultraviolet-curable adhesive. A pulse voltage (60 microseconds at 5 V) was applied to the TN device and the device was charged. A decaying voltage was measured for 16.7 milliseconds with a high-speed voltmeter, and area A between a voltage curve and a horizontal axis in a unit cycle was determined. Area B is an area without decay. A voltage holding ratio is a percentage of area A to area B.

Raw Material

Solmix A-11 (registered trade name) is a mixture of ethanol (85.5% by weight), methanol (13.4% by weight) and isopropanol (1.1% by weight), and was purchased from Japan Alcohol Trading Company Ltd.

Example 1

Synthesis of Compound (No. 141)

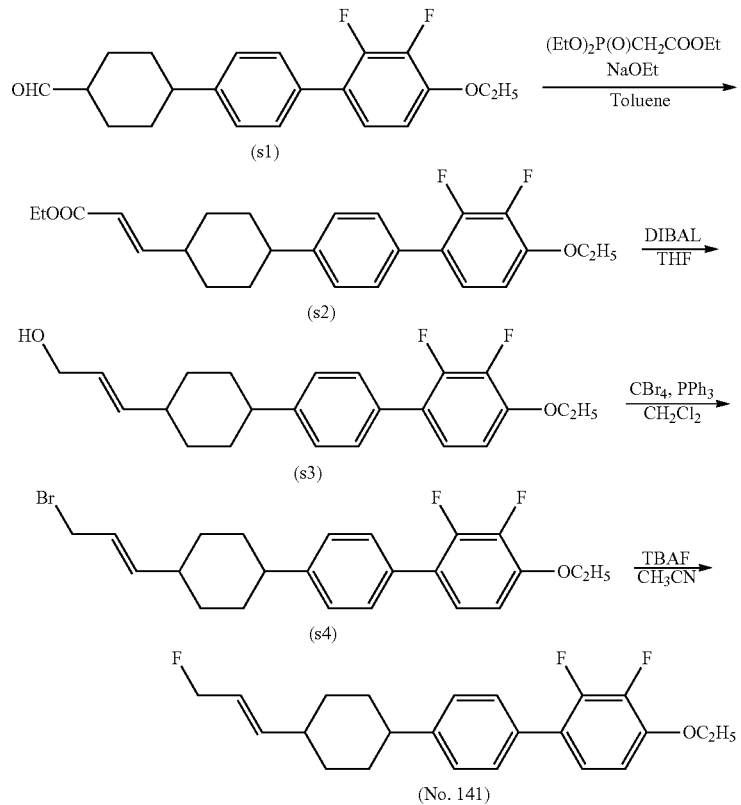

First Step:

Under a nitrogen atmosphere, aldehyde form (s1) (15.0 g), ethyl diethylphosphonoacetate (11.7 g) and toluene (150 mL) were put in a reaction vessel, and the resulting mixture was cooled to 0° C. Then, a 20% sodium ethoxide ethanol solution (17.8 g) was added thereto in the temperature range, and the resulting mixture was stirred for 2 hours. The reaction mixture was returned to 25° C. and further stirred for 2 hours, the reaction mixture was poured into water, and subjected to extraction with toluene. A combined organic layer was washed with water and dried over anhydrous magnesium sulfate. The resulting mixture was concentrated under reduced pressure, and the resulting residue was purified by silica gel chromatography (toluene) to give compound (s2) (15.7 g; 86.9%).

Second Step:

Under a nitrogen atmosphere, compound (s2) (15.7 g) and 200 mL of THF were put in a reaction vessel, and the resulting mixture was cooled to −20° C. Then, 1 moVL diisobutylaluminum hydride THF solution (83.3 mL) was added dropwise in a temperature range of −20° C. to −10° C., and the resulting mixture was further stirred in the temperature range for 2 hours. After reaction completion was confirmed by GC analysis, the reaction mixture was poured into water and subjected to extraction with ethyl acetate. A combined organic layer was washed with water and dried over anhydrous magnesium sulfate. The resulting mixture was concentrated under reduced pressure to give compound (s3) (14.0 g; 99.2%).

Third Step:

Under a nitrogen atmosphere, compound (s3) (7.0 g), carbon tetrabromide (9.3 g) and 200 mL of dichloromethane were put in a reaction vessel, and the resulting mixture was cooled to 0° C. Then, triphenyl phosphine (7.4 g) dissolved in dichloromethane (150 mL) was added dropwise thereto in a temperature range of 0 to 5° C., and the resulting mixture was further stirred in the temperature range for 2 hours. After reaction completion was confirmed by GC analysis, the reaction mixture was poured into water and subjected to extraction with toluene. A combined organic layer was washed with water and dried over anhydrous magnesium sulfate. The resulting mixture was concentrated under reduced pressure, and the resulting residue was purified by silica gel chromatography (volume ratio, toluene:heptane=1:1) to give compound (s4) (7.8 g; 95.3%).

Fourth Step:

Under a nitrogen atmosphere, compound (s4) (7.8 g), tetrabutylammonium fluoride trihydrate (23.4 g) and acetonitrile (150 mL) were put in a reaction vessel and the resulting mixture was stirred at 80° C. for 2 hours. The resulting reaction mixture was poured into water and subjected to extraction with toluene. The resulting mixture was concentrated under reduced pressure, and the resulting residue was purified by silica gel chromatography (toluene). The resulting residue was further purified by recrystallization from Solmix A-11 and dried to give compound (No. 141) (3.4 g; 50.0%).

$^1$H-NMR (δ ppm; CDCl$_3$): 7.45 (d, 2H), 7.28 (d, 2H), 7.07 (t, 1H), 6.78 (t, 1H), 5.83 (m, 1H), 5.70 (m, 1H), 4.82 (dd, 2H), 4.15 (q, 2H), 2.52 (t, 1H), 2.10 (m, 1H), 1.94 (dd, 4H), 1.55 (m, 4H), 1.50 (t, 3H), 1.30 (q, 2H).

Physical properties of compound (No. 141) were as described below. Transition temperature: C 124.0 N 205.0 I. $T_{NI}$=170.6° C.; Δn=0.202; Δ∈=−6.01; η=58.1 mPa·s.

Example 2

Synthesis of Compound (No. 142)

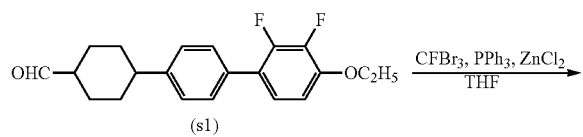

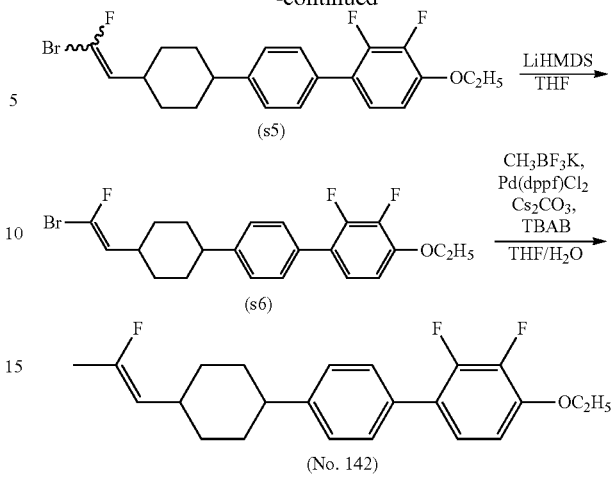

First Step:

Under a nitrogen atmosphere, compound (s1) (10.0 g), CFBr$_3$ (9.3 g), triphenylphosphine (9.1 g), and 200 mL of THF were put in a reaction vessel, and the resulting mixture was cooled to 0° C. Then, a 1 M zinc chloride (II) THF solution (34.8 mL) was added dropwise thereto in a temperature range of 0 to 5° C., and the resulting mixture was further stirred in the temperature range for 2 hours. After reaction completion was confirmed by GC analysis, the reaction mixture was poured into water and subjected to extraction with toluene. A combined organic layer was washed with water and dried over anhydrous magnesium sulfate. The resulting mixture was concentrated under reduced pressure, and the resulting residue was purified by silica gel chromatography (volume ratio, toluene:heptane=1:1) to give compound (s5) (9.2 g; 72.1%).

Second Step:

Under a nitrogen atmosphere, compound (s5) (9.2 g) and 100 mL of THF were put in a reaction vessel, and the resulting mixture was cooled to 0° C. Then, a lithium hexamethyldisilazane THF solution (10.1 mL) was added dropwise thereto at room temperature, and the resulting mixture was further stirred in the temperature range for 2 hours. After reaction completion was confirmed by GC analysis, the reaction mixture was poured into water and subjected to extraction with toluene. A combined organic layer was washed with water and dried over anhydrous magnesium sulfate. The resulting mixture was concentrated under reduced pressure, and the resulting residue was purified by silica gel chromatography (volume ratio, toluene:heptane=1:1) to give compound (s6) (4.6 g; 47.7%).

Third Step:

Under a nitrogen atmosphere, compound (s6) (4.6 g), CH$_3$BF$_3$K (s2) (1.4 g), cesium carbonate (10.2 g), Pd(dppf)Cl$_2$ (0.69 g), TBAB (0.68 g), THF (50 mL) and water (50 mL) were put in a reaction vessel, and the resulting mixture was refluxed under heating for 2 hours. The resulting reaction mixture was poured into water and subjected to extraction with toluene. A combined organic layer was washed with water and dried over anhydrous magnesium sulfate. The resulting mixture was concentrated under reduced pressure, and the resulting residue was purified by silica gel chromatography (toluene). The resulting residue was further purified by recrystallization from Solmix A-11 and dried to give compound (No. 142) (0.3 g; 7.6%).

$^1$H-NMR (δ ppm; CDCl$_3$): 7.43 (d, 2H), 7.27 (d, 2H), 7.08 (t, 1H), 6.78 (t, 1H), 4.39 (dd, 1H), 4.15 (q, 2H), 2.50 (m, 1H), 2.00-1.80 (m, 6H), 1.55 (m, 4H), 1.48 (t, 3H), 1.24 (q, 2H).

Physical properties of compound (No. 142) were as described below. Transition temperature: C 97.7 N 168.1 I. T$_{NI}$=131.9° C.; Δn=0.190; Δ∈=−5.56.

Example 3

Synthesis of Compound (No. 143)

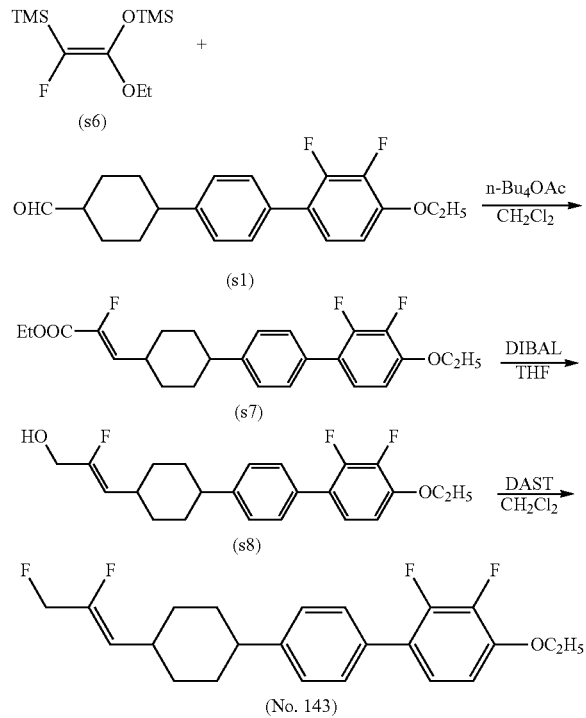

First Step:

Under a nitrogen atmosphere, compound (s1) (6.0 g), compound (s6) (4.8 g), tetrabutylammonium acetate (0.26 g) and 100 mL of dichloromethane were put in a reaction vessel, and the resulting mixture was cooled to 0° C. Then, compound (s6) (4.8 g) was added dropwise thereto in a temperature range of 0° C. to 5° C., and the resulting mixture was further stirred in the temperature range for 2 hours. After reaction completion was confirmed by GC analysis, the reaction mixture was poured into water and subjected to extraction with toluene. A combined organic layer was washed with water and dried over anhydrous magnesium sulfate. The resulting mixture was concentrated under reduced pressure, and the resulting residue was purified by silica gel chromatography (volume ratio, toluene:heptane=1:1) to give compound (s7) (5.0 g; 66.4%).

Second Step:

Under a nitrogen atmosphere, compound (s7) (5.0 g) and 50 mL of THF were put in a reaction vessel, and the resulting mixture was cooled to −20° C. Then, 1 mol/L diisobutylaluminium hydride THF solution (27.8 mL) was added dropwise in a temperature range of −20° C. to −10° C., and the resulting mixture was further stirred in the temperature range for 2 hours. After reaction completion was confirmed by GC analysis, the reaction mixture was poured into water and subjected to extraction with ethyl acetate. A combined organic layer was washed with water and dried over anhydrous magnesium sulfate. The resulting mixture was concentrated under reduced pressure to give compound (s8) (4.4 g, 97.5%).

Third Step:

Under a nitrogen atmosphere, compound (s8) (4.4 g) and 50 mL of dichloromethane were put in a reaction vessel, and the resulting mixture was cooled to −30° C. Then, diethylaminosulfur trifluoride (DAST) (1.8 mL) was added dropwise thereto in a temperature range of −30° C. to −20° C., and the resulting mixture was further stirred in the temperature range for 8 hours. After reaction completion was confirmed by GC analysis, the reaction mixture was poured into water and subjected to extraction with toluene. A combined organic layer was washed with water and dried over anhydrous magnesium sulfate. The resulting mixture was concentrated under reduced pressure, the resulting residue was purified by silica gel chromatography (volume ratio, toluene:heptane=1:1), and further purified by recrystallization from Solmix A-11 to give compound (No. 143) (0.72 g; 16.0%).

$^1$H-NMR (δ ppm; CDCl$_3$): 7.43 (d, 2H), 7.27 (d, 2H), 7.09 (t, 1H), 4.92 (m, 1H), 4.77 (dd, 2H), 4.15 (q, 2H), 2.54 (m, 1H), 1.93 (dd, 4H), 1.57 (m, 4H), 1.48 (t, 3H), 1.30 (q, 2H).

Physical properties of compound (No. 143) were as described below. Transition temperature: C 104.4 N 171.8 I. T$_{NI}$ =141.9° C.; Δn=0.190; Δ∈=−7.53.

Example 4

According to techniques shown in Examples 1 to 3, various compounds were prepared using corresponding starting materials, and confirmed to be objective compounds.

Compound (No. 7)

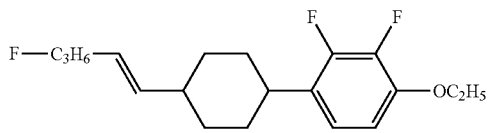

$^1$H-NMR (δ ppm; CDCl$_3$): 6.84 (t, 1H), 6.67 (t, 1H), 5.42 (m, 2H), 4.46 (td, 2H), 4.09 (q, 2H), 2.74 (t, 1H), 2.12 (q, 2H), 1.97 (m, 1H), 1.85 (t, 4H), 1.75 (m, 2H), 1.53-1.40 (m, 5H), 1.25 (m, 2H).

Physical properties of compound (No. 7) were as described below. Transition temperature: C 55.7 I. T$_{NI}$=12.6° C.; Δn=0.094; Δ∈=−7.08.

Compound (No. 20)

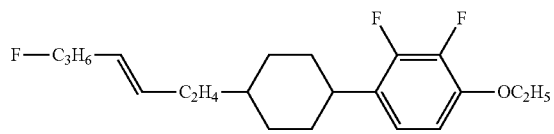

$^1$H-NMR (δ ppm; CDCl$_3$): 6.83 (t, 1H), 6.66 (t, 1H), 5.43 (m, 2H), 4.45 (td, 2H), 4.09 (q, 2H), 2.74 (t, 1H), 2.14 (q, 2H), 2.03 (q, 2H), 1.85 (m, 4H), 1.77 (m, 2H), 1.43 (m, 5H), 1.29 (t, 3H), 1.08 (m, 2H).

Physical properties of compound (No. 20) were as described below. Transition temperature: C 38.6 I. T$_{NI}$ =2.6° C.; Δn=0.080; Δ∈=−5.65.

Compound (No. 57)

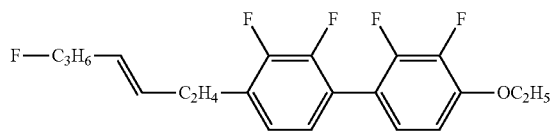

$^1$H-NMR (δ ppm; CDCl$_3$): 7.02 (m, 1H), 6.98 (t, 1H), 6.80 (t, 1H), 5.46 (m, 2H), 4.40 (td, 2H), 4.17 (q, 2H), 2.77 (t, 2H), 2.35 (q, 2H), 2.11 (q, 2H), 1.73 (m, 2H), 1.49 (t, 3H).

Physical properties of compound (No. 57) were as described below. Transition temperature: C 31.1 I. T$_{NI}$=−25.0° C.; Δn=0.114; Δ∈=−7.92.

Compound (No. 89)

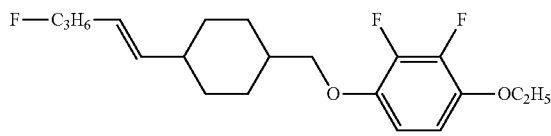

$^1$H-NMR (δ ppm; CDCl$_3$): 6.69 (t, 1H), 5.40 (m, 2H), 4.45 (td, 2H), 4.05 (q, 2H), 3.77 (d, 2H), 2.11 (m, 2H), 1.92 (d, 3H), 1.85-1.70 (m, 5H), 1.42 (t, 3H), 1.12 (m, 4H).

Physical properties of compound (No. 89) were as described below.

Transition temperature: C 36.7 I. T$_{NI}$=17.0° C.; Δn=0.094; Δ∈=−8.38.

Example 5

Compounds (No. 1) to (No. 320) shown below can be prepared in a manner similar to the synthesis methods as described in Examples 1 to 4. Attached data were determined according to the methods described above. When a transition temperature was measured, a compound itself was used as a sample. When a maximum temperature (T$_{NI}$), optical anisotropy (Δn) and dielectric anisotropy (Δ∈) were measured, a mixture of the compound (15% by weight) and the base liquid crystal (i) (85% by weight) was used as a sample. From the measured values, extrapolated values were calculated according to the extrapolation method described above, and the calculated values were described. In addition, in compound (No. 141), a sample for measurement was prepared from 10% by weight of compound (No. 136) and 90% by weight of base liquid crystal (i) because a crystal precipitated at an ordinary ratio (15% by weight:85% by weight).

| No. | |
|---|---|
| 1 | ![structure] F-CH=CH-CH2-Cy-Ph(2,3-F2)-OC2H5 |
| 2 | ![structure] CH3-C(F)=CH-Cy-Ph(2,3-F2)-OC2H5 |
| 3 | ![structure] F-CH2-C(F)=CH-Cy-Ph(2,3-F2)-OC2H5 |
| 4 | ![structure] F-C2H4-CH=CH-Cy-Ph(2,3-F2)-CH3 |
| 5 | ![structure] C2H5-C(F)=CH-Cy-Ph(2,3-F2)-OC2H5 |
| 6 | ![structure] F-C2H4-C(F)=CH-Cy-Ph(2,3-F2)-C2H5 |

-continued
| No. | |
|---|---|
| 7 | 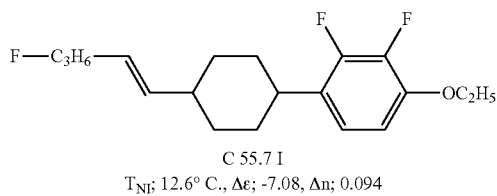<br>C 55.7 I<br>T_NI; 12.6° C., Δε; -7.08, Δn; 0.094 |
| 8 | 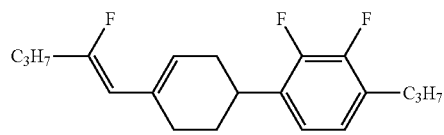 |
| 9 | 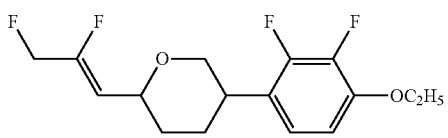 [SMILES: CCOc1ccc(C2CCC(/C=C(\F)CF)OC2)c(F)c1F] |
| 10 | 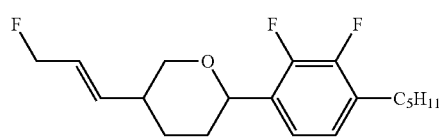 |
| 11 | 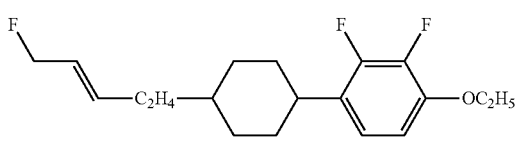 |
| 12 | 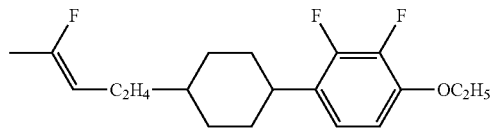 |
| 13 | 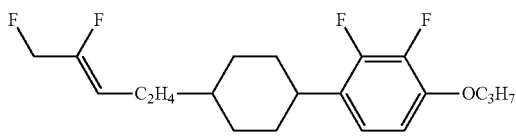 |
| 14 | 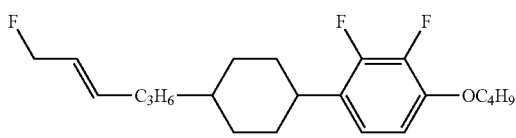 |
| 15 | 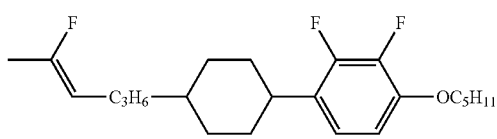 |
| 16 | 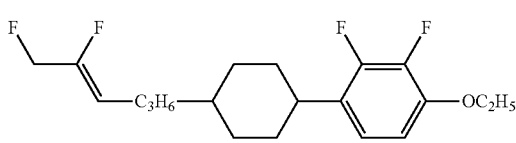 |

-continued
| No. | |
|---|---|
| 17 | 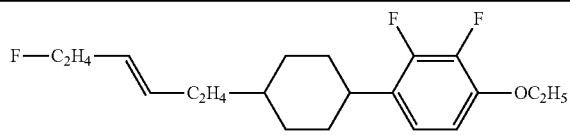 |
| 18 | 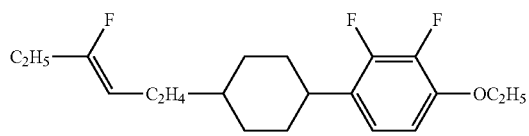 |
| 19 | 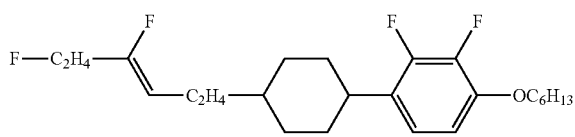 |
| 20 | 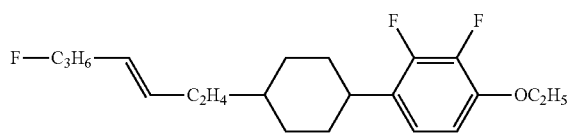 C 38.6 I |
| 21 | 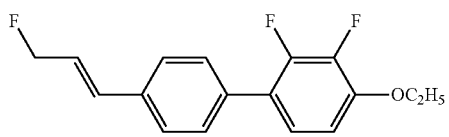 [SMILES: CCOc1ccc(-c2ccc(/C=C/CF)cc2)c(F)c1F] |
| 22 | 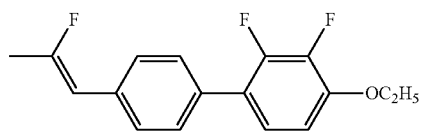 [SMILES: CCOc1ccc(-c2ccc(/C=C(/C)F)cc2)c(F)c1F] |
| 23 | 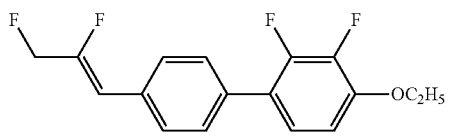 [SMILES: CCOc1ccc(-c2ccc(/C=C(\F)CF)cc2)c(F)c1F] |
| 24 | 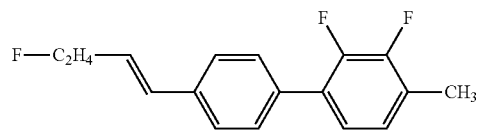 |
| 25 | 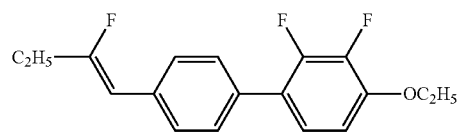 [SMILES: CCOc1ccc(-c2ccc(/C=C(\F)CC)cc2)c(F)c1F] |
| 26 | 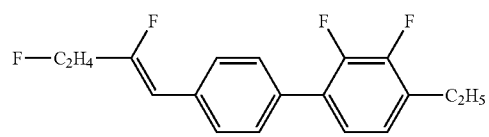 |
| 27 | 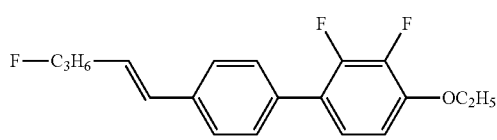 |

-continued
| No. | |
|---|---|
| 28 | 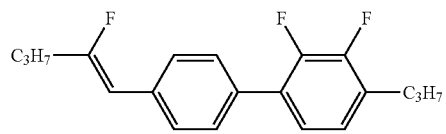 |
| 29 | 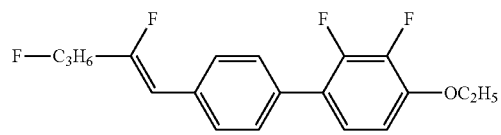 |
| 30 | 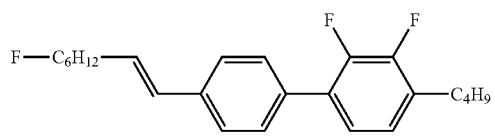 |
| 31 | 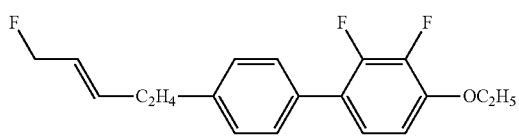 |
| 32 | 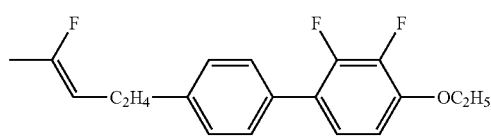 |
| 33 | 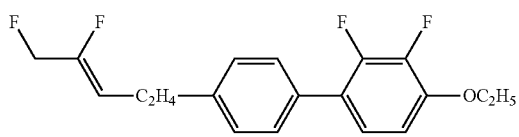 |
| 34 | 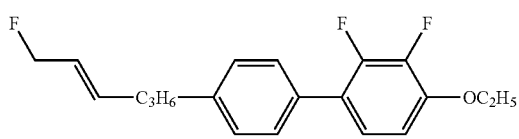 |
| 35 | 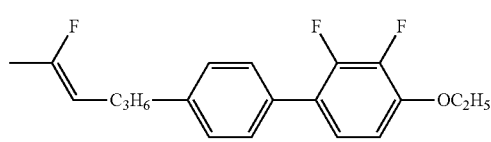 |
| 36 | 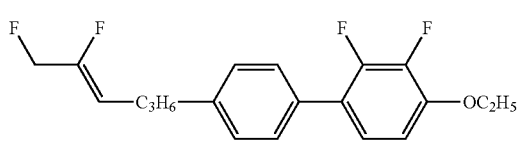 |
| 37 | 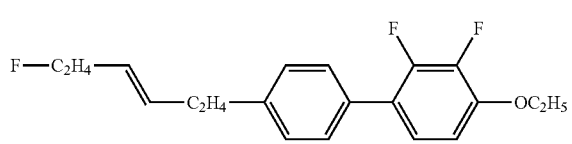 |
| 38 | 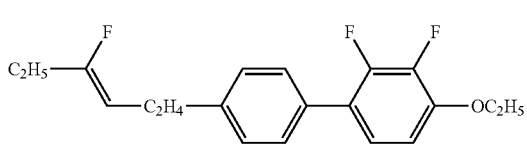 |

-continued
| No. | |
|---|---|
| 39 | 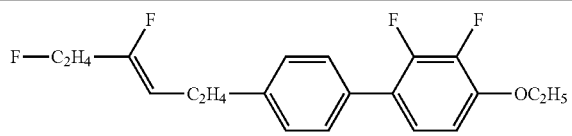 |
| 40 | 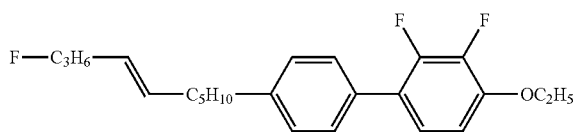 |
| 41 | 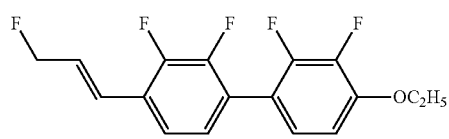 |
| 42 | 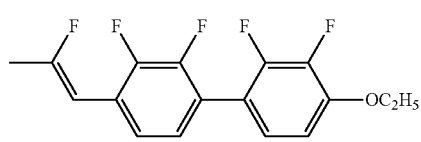 |
| 43 | 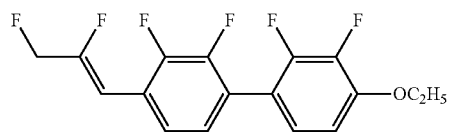 |
| 44 | 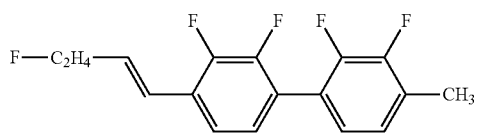 |
| 45 | 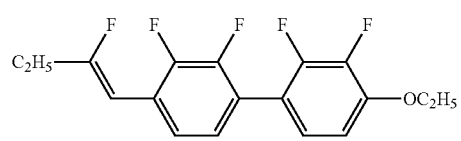 |
| 46 | 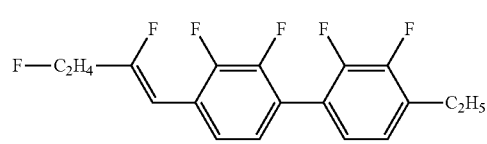 |
| 47 | 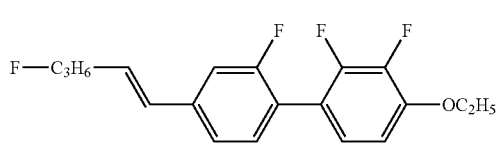 |
| 48 | 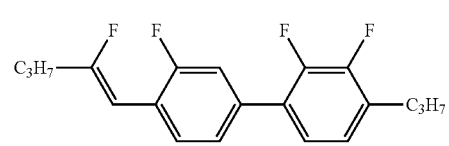 |
| 49 | 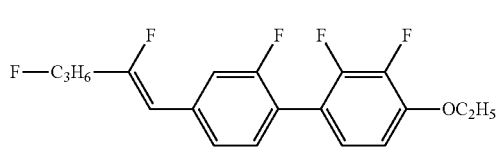 |

-continued
| No. | |
|---|---|
| 50 | 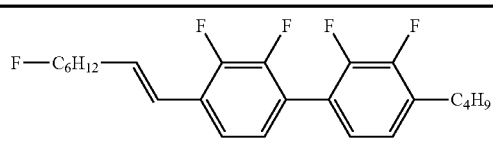 |
| 51 | 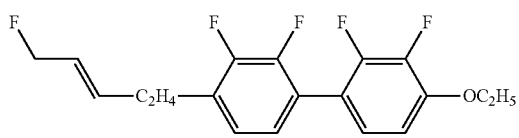 |
| 52 | 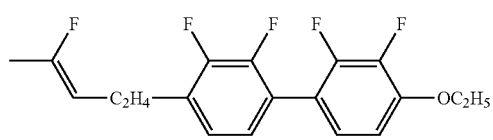 |
| 53 | 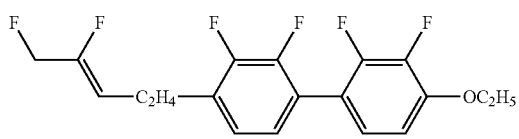 |
| 54 | 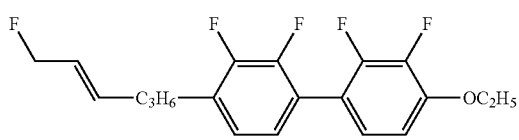 |
| 55 | 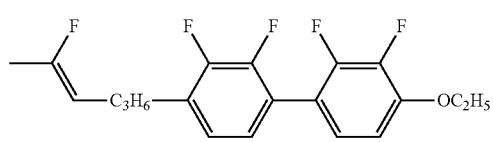 |
| 56 | 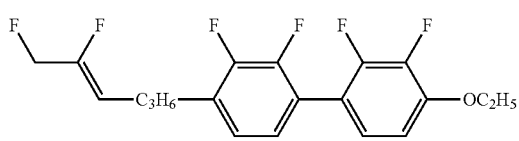 |
| 57 | 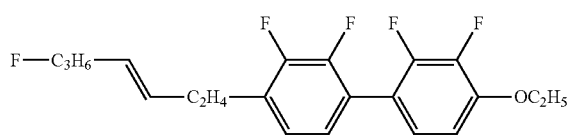<br>C 31.1 I<br>$T_{NI}$;-25.0° C., $\Delta\varepsilon$; -7.92, $\Delta n$; 0.114 |
| 58 | 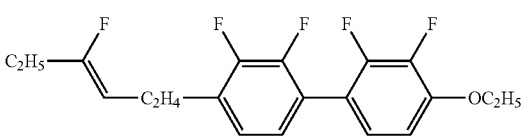 |
| 59 | 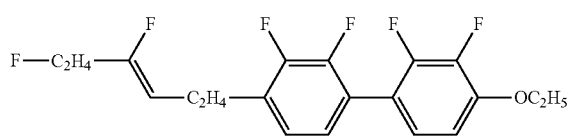 |
| 60 | 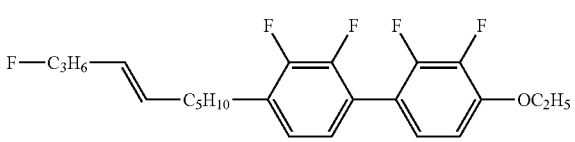 |

| No. | |
|---|---|
| 61 | 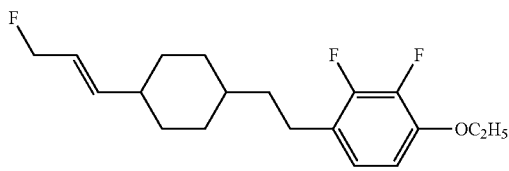 [SMILES: CCOc1ccc(CCC2CCC(/C=C/CF)CC2)c(F)c1F] |
| 62 | 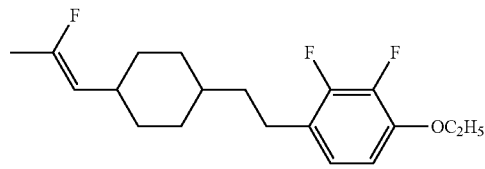 |
| 63 | 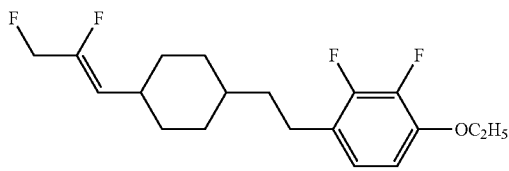 |
| 64 | 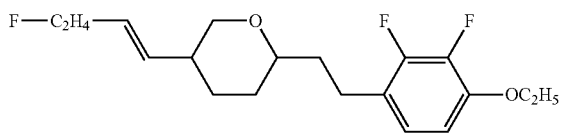 |
| 65 | 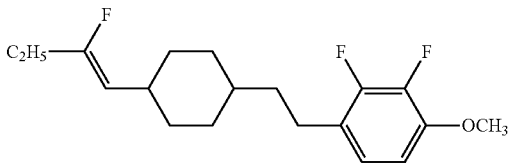 [SMILES: CC/C(F)=C/C1CCC(CCc2ccc(OC)c(F)c2F)CC1] |
| 66 | 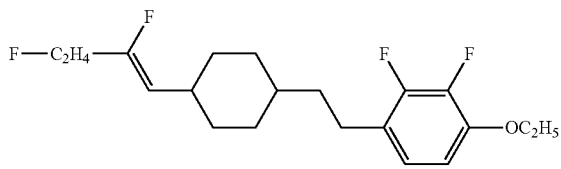 |
| 67 | 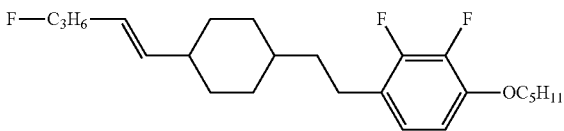 |
| 68 | 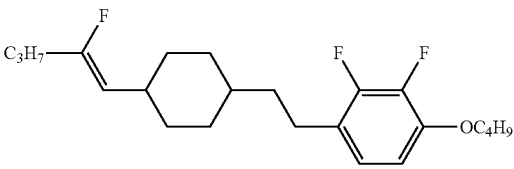 |
| 69 | 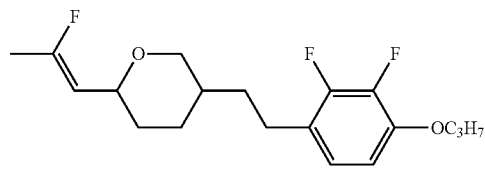 |

| No. | |
|---|---|
| 70 | 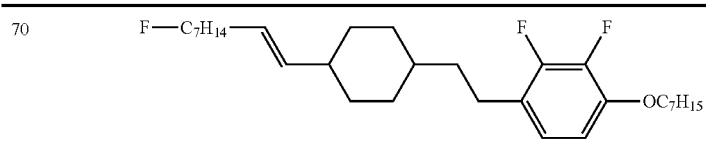 |
| 71 | 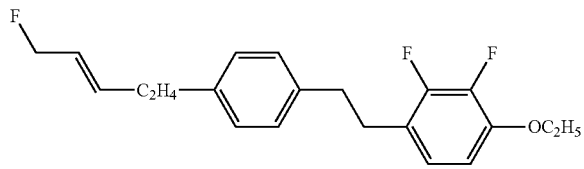 |
| 72 | 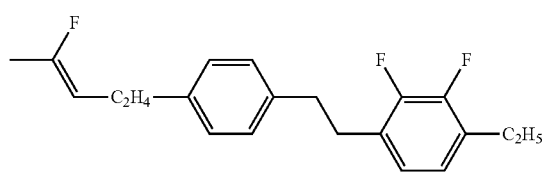 |
| 73 | 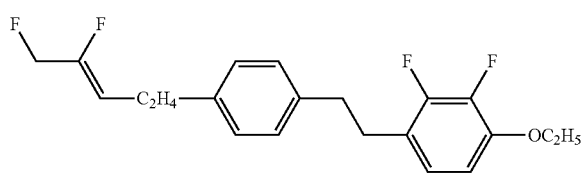 |
| 74 | 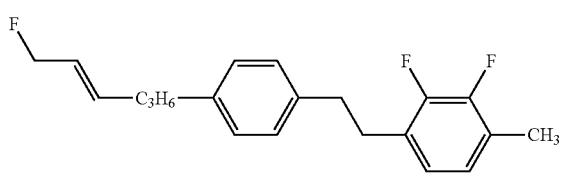 |
| 75 | 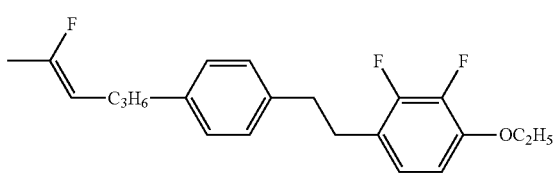 |
| 76 | 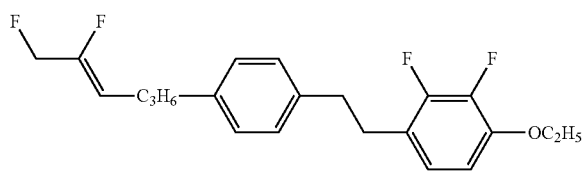 |
| 77 | 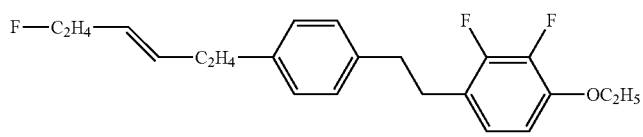 |
| 78 | 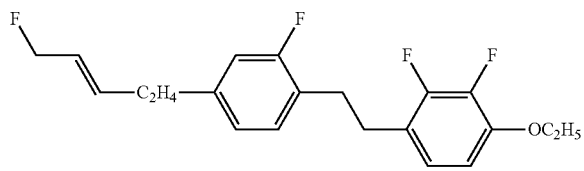 |

| No. | |
|---|---|
| 79 | 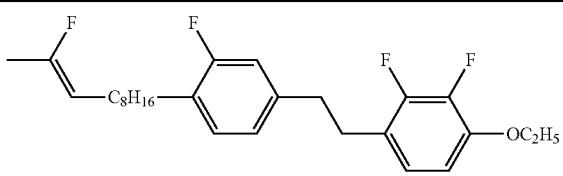 |
| 80 | 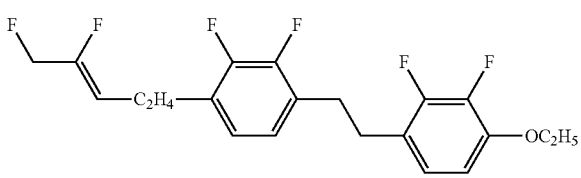 |
| 81 | 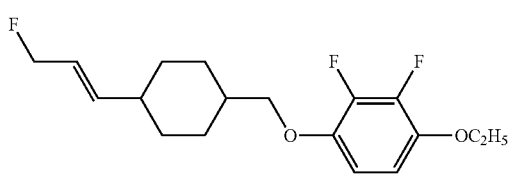 |
| 82 | 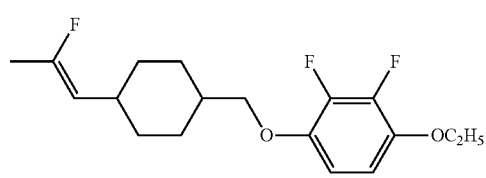 |
| 83 | 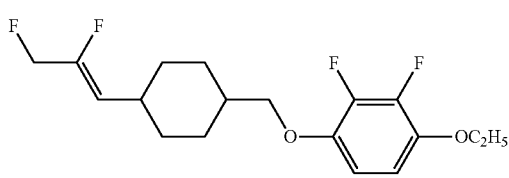 |
| 84 | 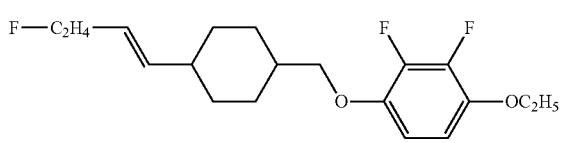 |
| 85 | 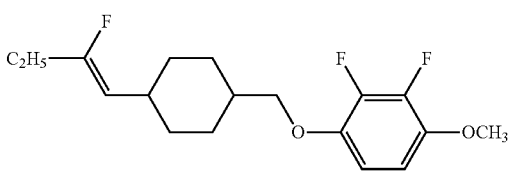 [SMILES: CC/C(F)=C/C1CCC(COc2ccc(OC)c(F)c2F)CC1] |
| 86 | 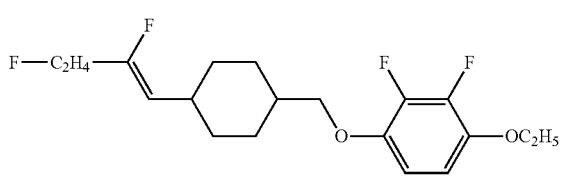 |
| 87 | 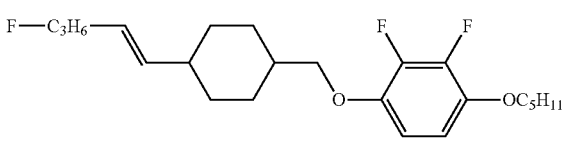 |

| No. | |
|---|---|
| 88 | 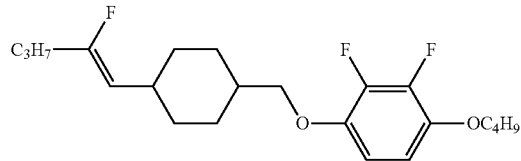 |
| 89 | 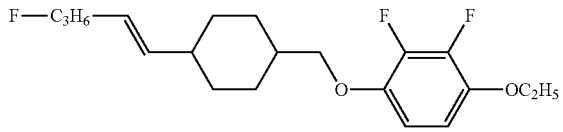
C 36.7 I
$T_{NI}$; 17.0° C., Δε; -8.38, Δn; 0.094 |
| 90 | 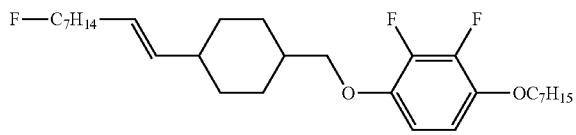 |
| 91 | 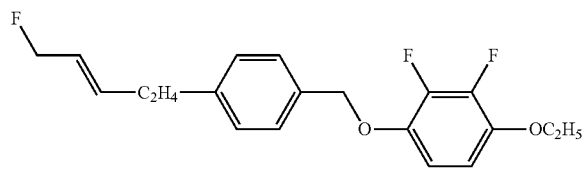 |
| 92 | 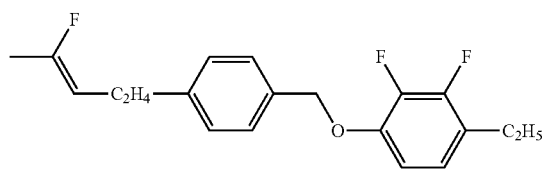 |
| 93 | 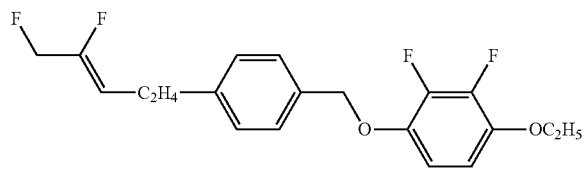 |
| 94 | 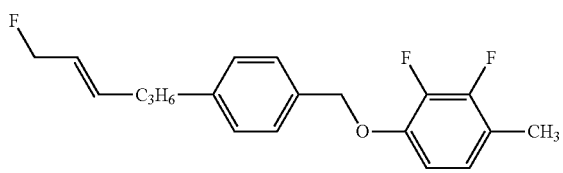 |
| 95 | 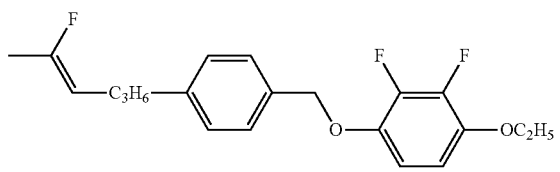 |
| 96 | 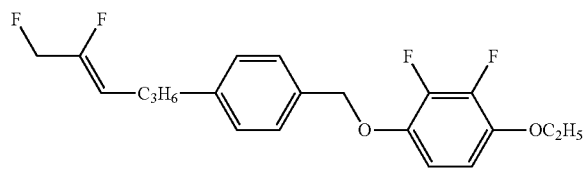 |

-continued
| No. | |
|---|---|
| 97 | 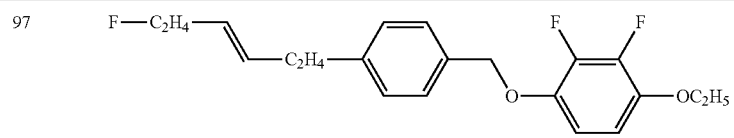 |
| 98 | 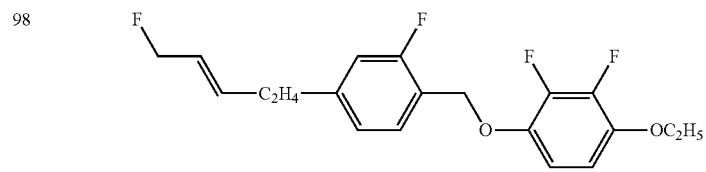 |
| 99 | 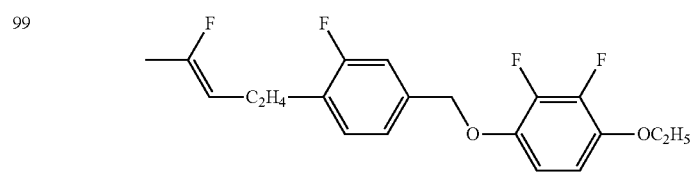 |
| 100 | 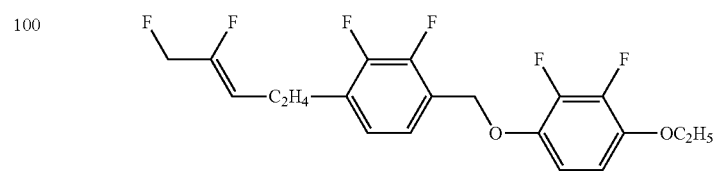 |
| 101 | 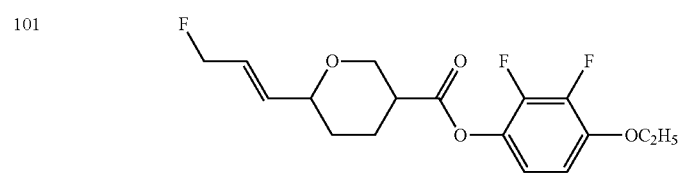 |
| 102 | 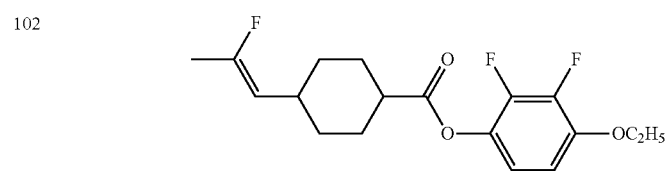 |
| 103 | 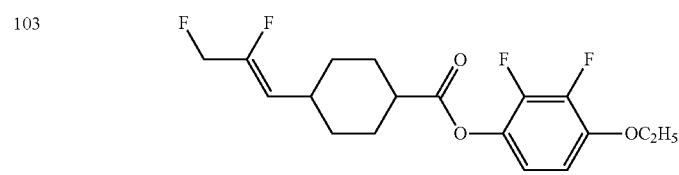 |
| 104 | 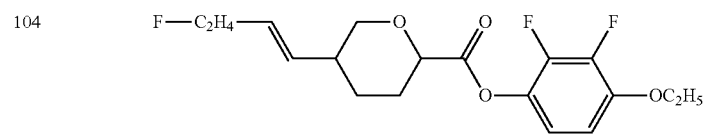 |
| 105 | 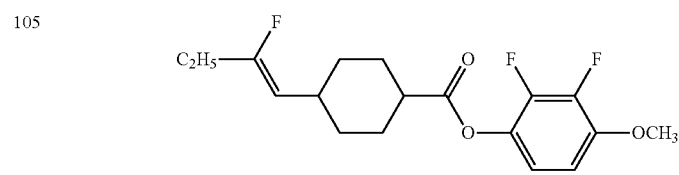 |

-continued
| No. | |
|---|---|
| 106 | 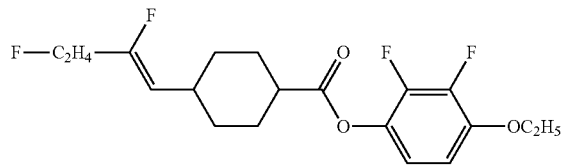 |
| 107 | 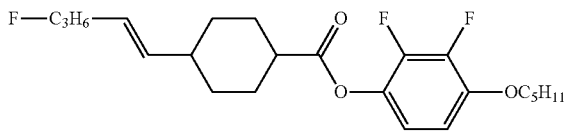 |
| 108 | 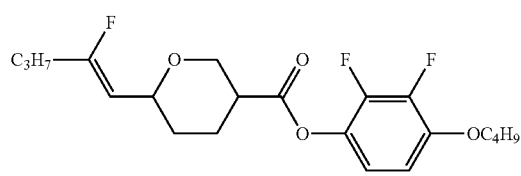 |
| 109 | 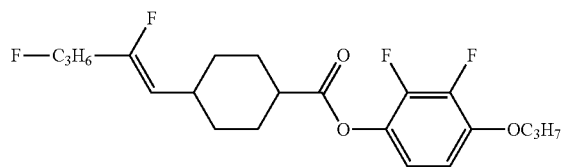 |
| 110 | 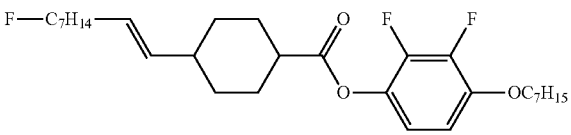 |
| 111 | 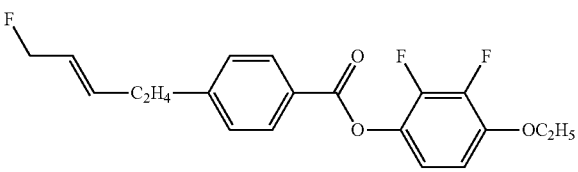 |
| 112 | 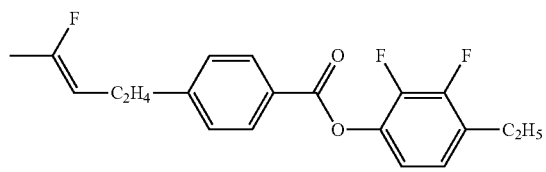 |
| 113 | 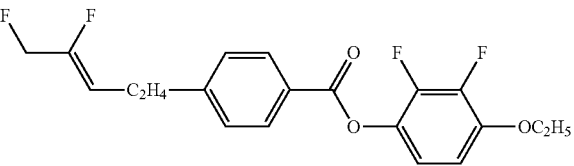 |
| 114 | 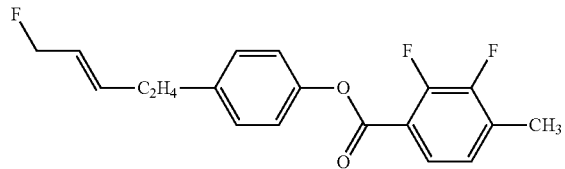 |

| No. | |
|---|---|
| 115 | 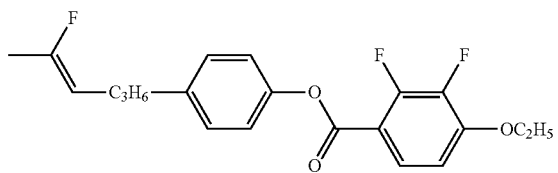 |
| 116 | 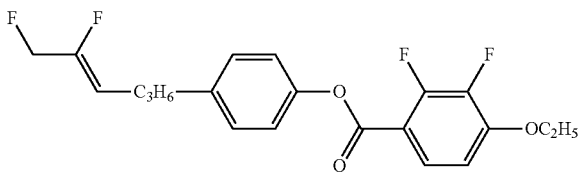 |
| 117 | 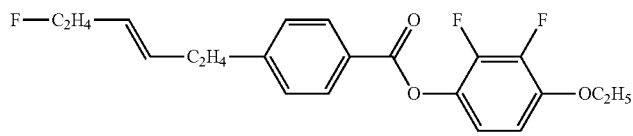 |
| 118 | 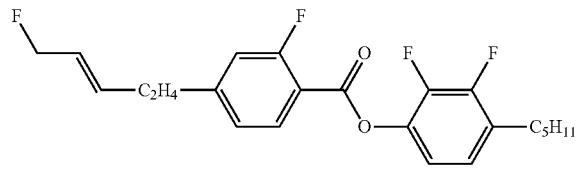 |
| 119 | 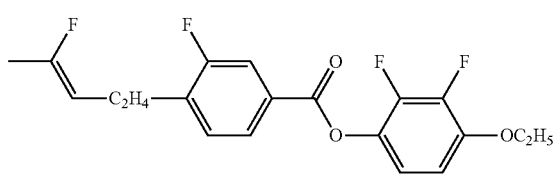 |
| 120 | 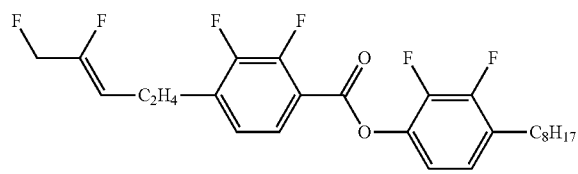 |
| 121 | 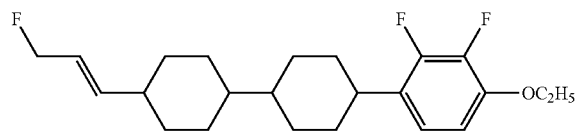 [SMILES: CCOc1ccc(C2CCC(C3CCC(/C=C/CF)CC3)CC2)c(F)c1F] |
| 122 | 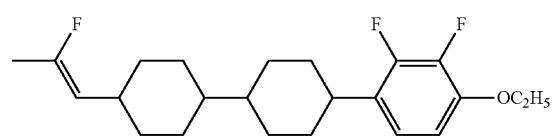 [SMILES: CCOc1ccc(C2CCC(C3CCC(/C=C(/C)F)CC3)CC2)c(F)c1F] |
| 123 | 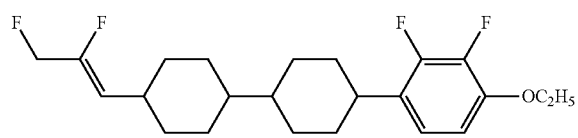 [SMILES: CCOc1ccc(C2CCC(C3CCC(/C=C(\F)CF)CC3)CC2)c(F)c1F] |
| 124 | 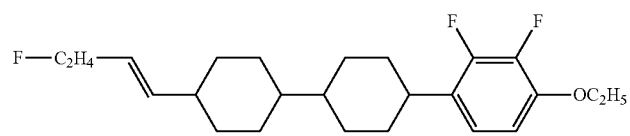 |

-continued
| No. | |
|---|---|
| 125 | 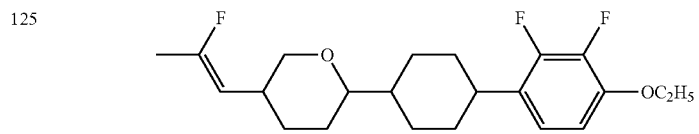 |
| 126 | 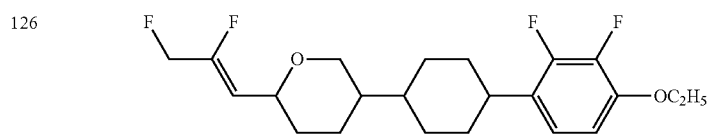 |
| 127 | 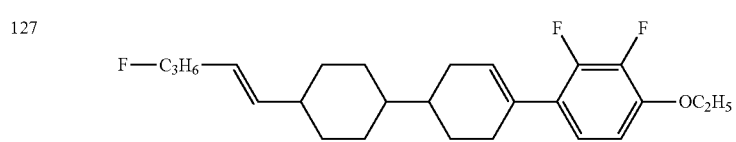 |
| 128 | 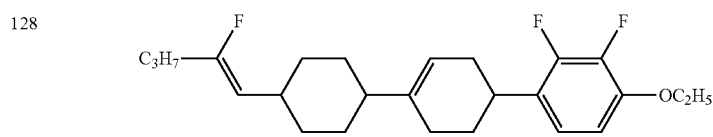 |
| 129 | 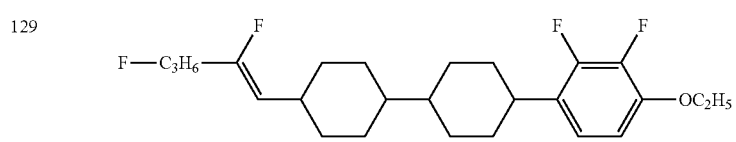 |
| 130 | 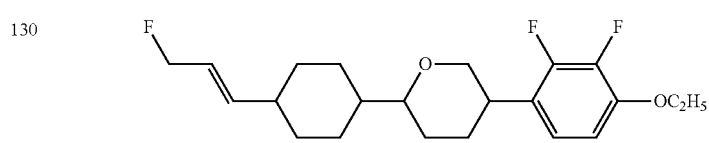 |
| 131 | 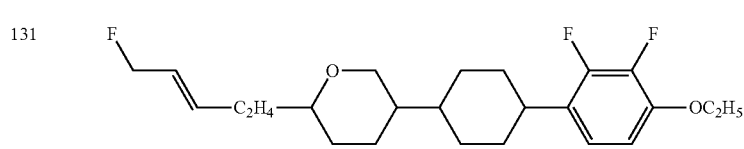 |
| 132 | 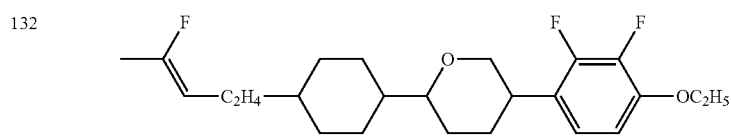 |
| 133 | 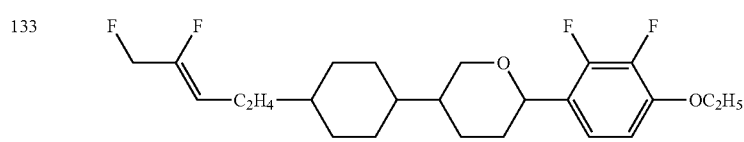 |
| 134 | 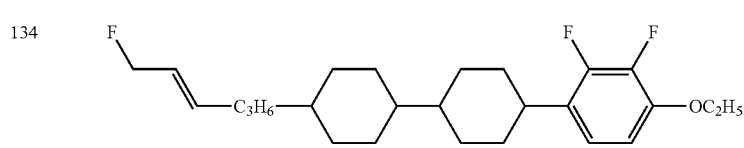 |
| 135 | 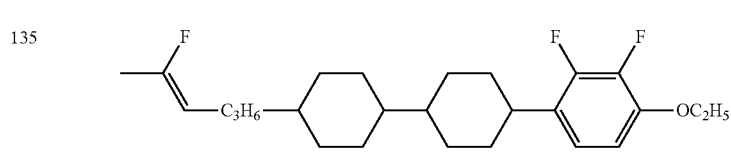 |

-continued
| No. | |
|---|---|
| 136 | 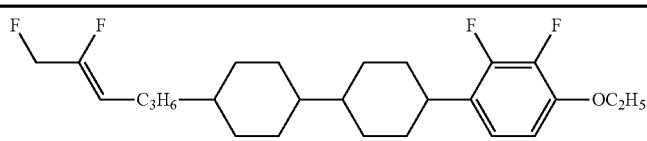 |
| 137 | 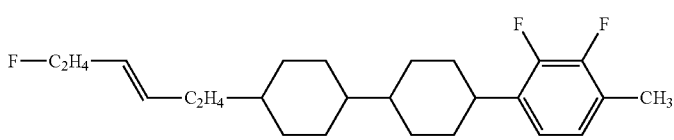 |
| 138 | 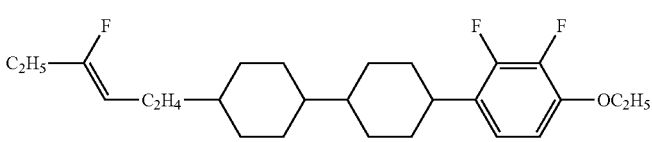 |
| 139 | 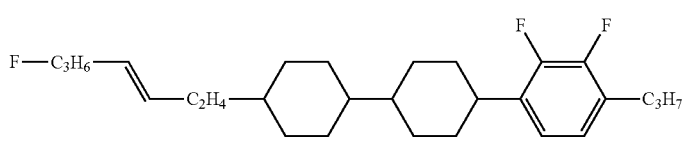 |
| 140 | 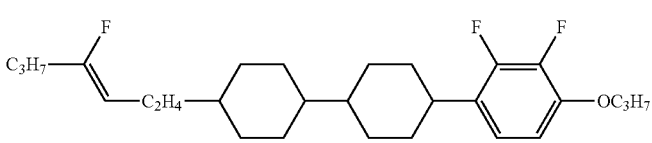 |
| 141 | 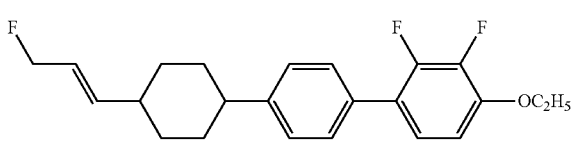  C 124.0 N 205.0 I  $T_{NI}$; 170.6° C., $\Delta\epsilon$; -6.01, $\Delta n$; 0.202 |
| 142 | 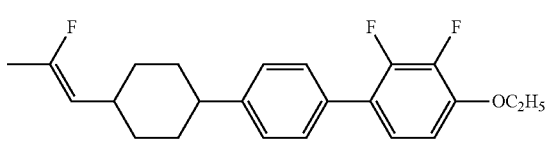  C 97.7 N 168.1 I  $T_{NI}$; 131.9° C., $\Delta\epsilon$; -5.56, $\Delta n$; 0.190 |
| 143 | 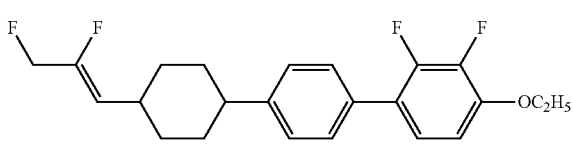  C 104.4 N 171.8 I  $T_{NI}$; 141.9° C., $\Delta\epsilon$; -7.53, $\Delta n$; 0.190 |
| 144 | 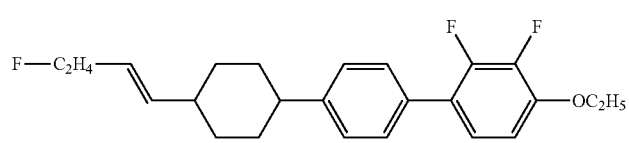 |
| 145 | 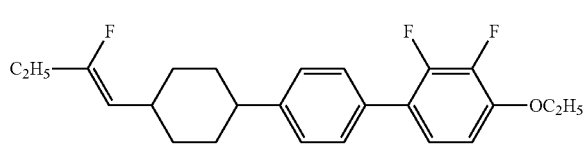 |

| No. | |
|---|---|
| 146 | 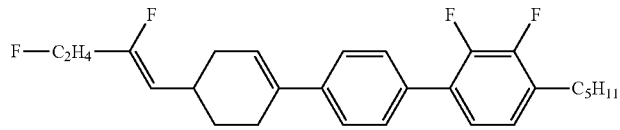 |
| 147 | 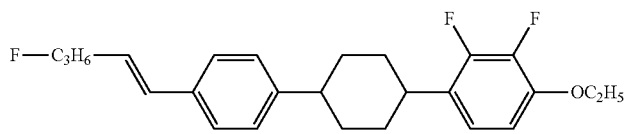 |
| 148 | 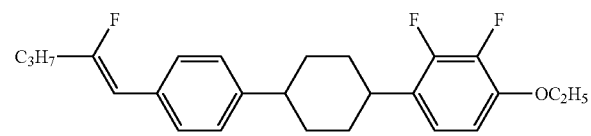 |
| 149 | 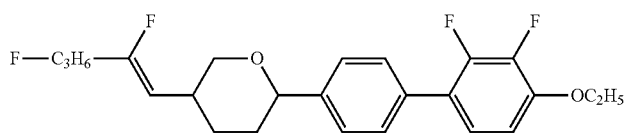 |
| 150 | 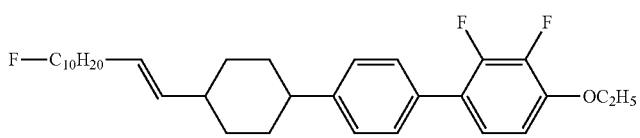 |
| 151 | 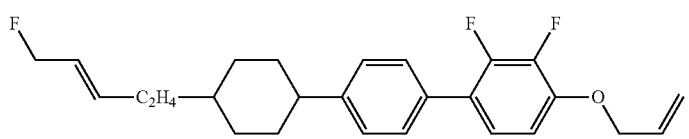 |
| 152 | 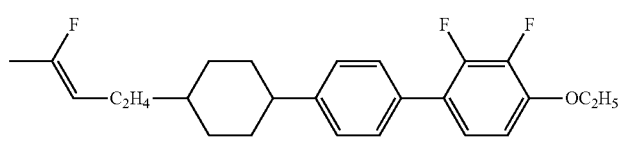 |
| 153 | 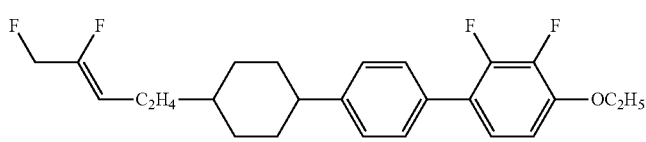 |
| 154 | 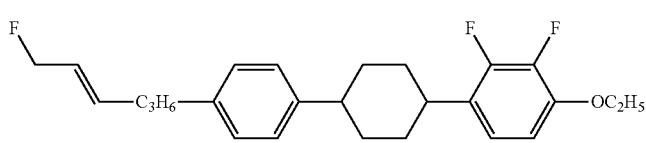 |
| 155 | 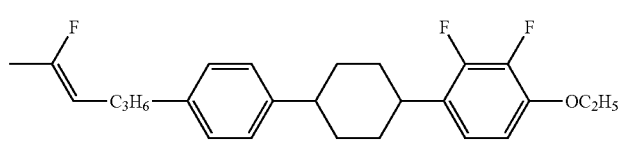 |
| 156 | 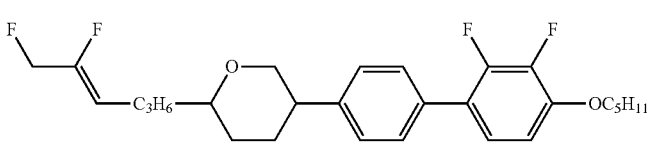 |

| No. | |
|---|---|
| 157 | 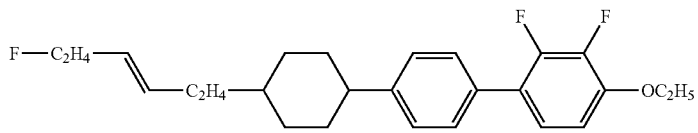 |
| 158 | 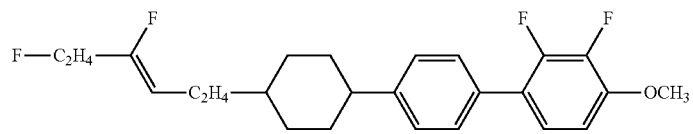 |
| 159 | 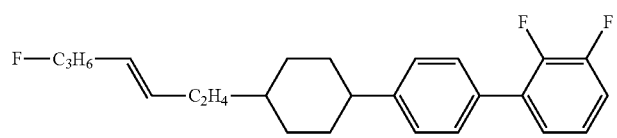 |
| 160 | 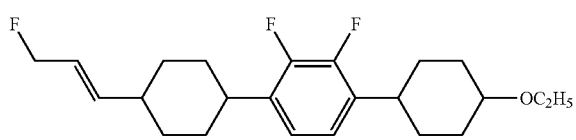 [SMILES: CCOC1CCC(c2ccc(C3CCC(/C=C/CF)CC3)c(F)c2F)CC1] |
| 161 | 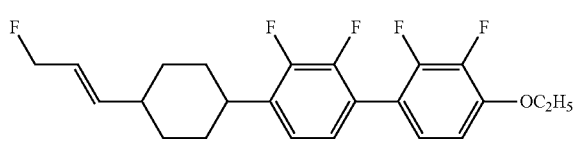 |
| 162 | 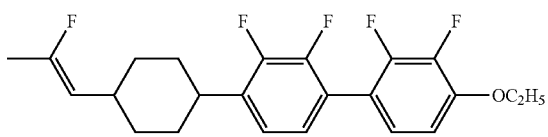 |
| 163 | 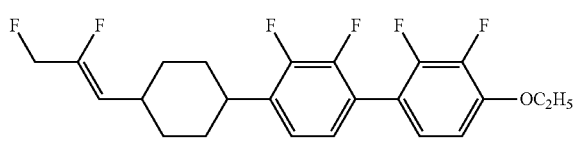 |
| 164 | 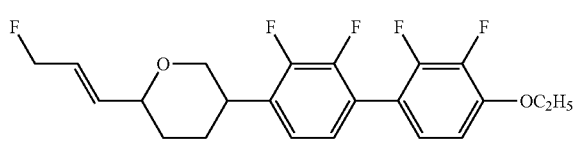 [SMILES: CCOc1ccc(-c2ccc(C3CCC(/C=C/CF)CC3)c(F)c2F)c(F)c1F] |
| 165 | 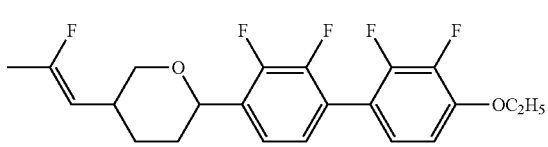 [SMILES: CCOc1ccc(-c2ccc(C3CCC(/C=C(/C)F)CC3)c(F)c2F)c(F)c1F] |
| 166 | 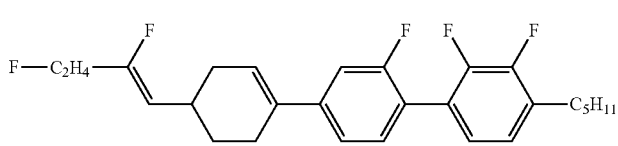 |
| 167 | 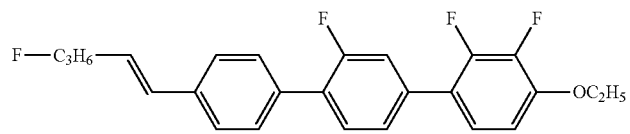 |

-continued
| No. | |
|---|---|
| 168 | 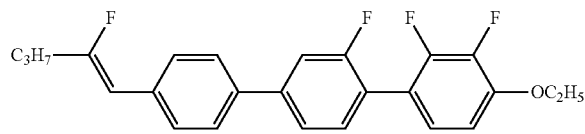 |
| 169 | 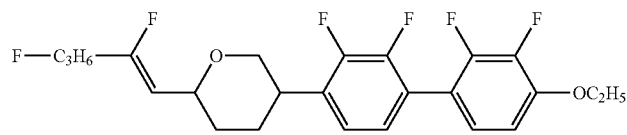 |
| 170 | 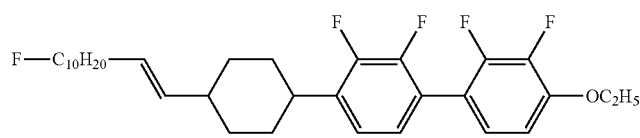 |
| 171 | 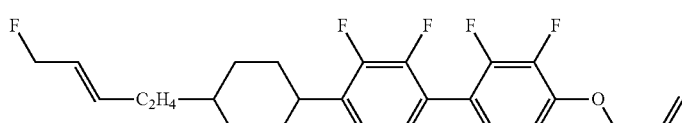 |
| 172 | 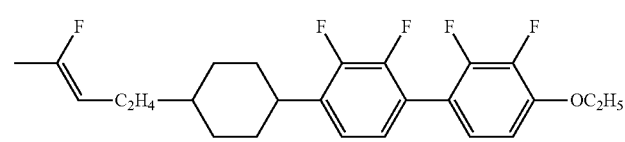 |
| 173 | 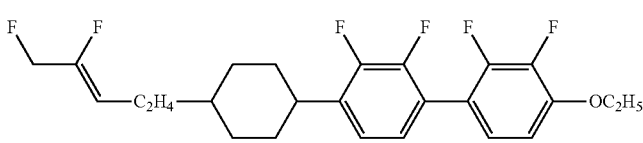 |
| 174 | 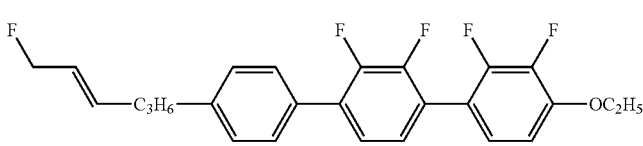 |
| 175 | 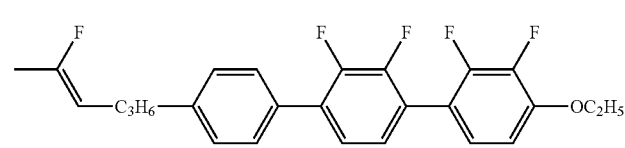 |
| 176 | 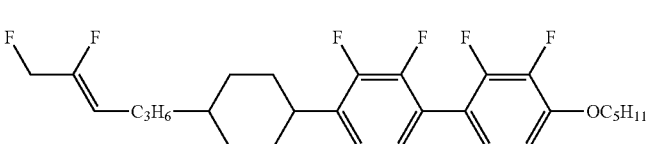 |
| 177 | 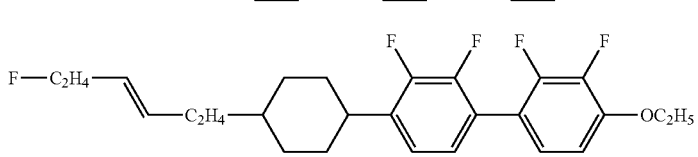 |
| 178 | 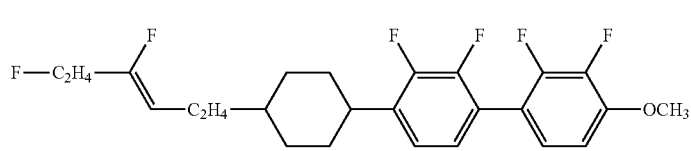 |

| No. | |
|---|---|
| 179 | 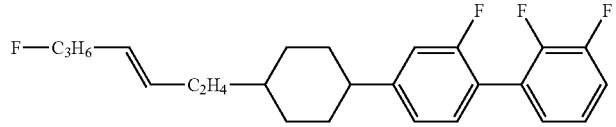 |
| 180 | 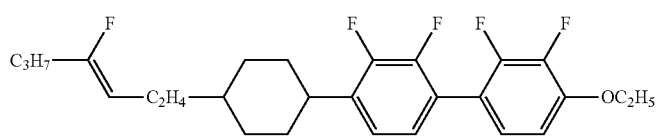 |
| 181 | 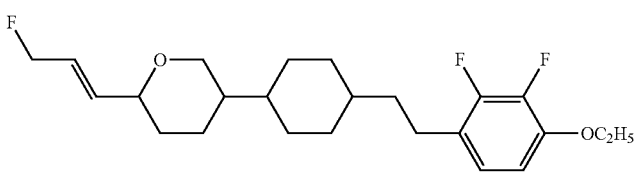 |
| 182 | 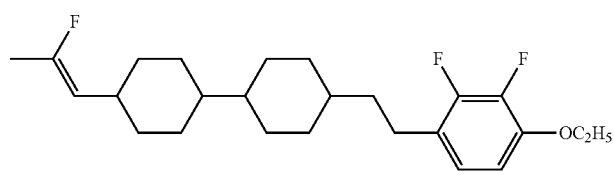 [SMILES: CCOc1ccc(CCC2CCC(C3CCC(/C=C(/C)F)CC3)CC2)c(F)c1F] |
| 183 | 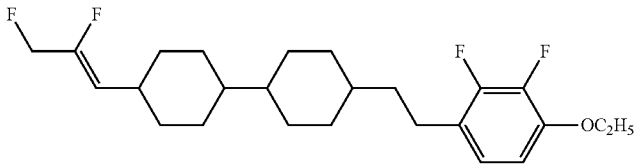 |
| 184 | 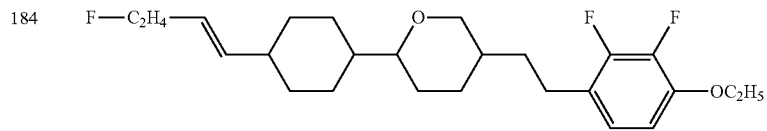 |
| 185 | 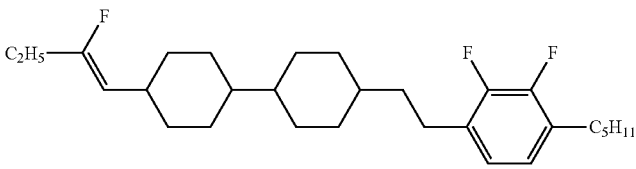 |
| 186 | 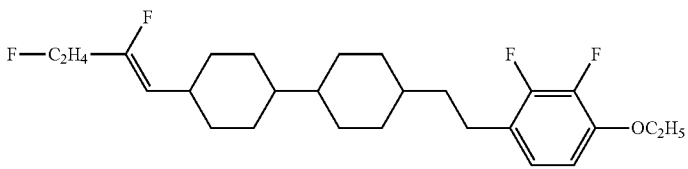 |
| 187 | 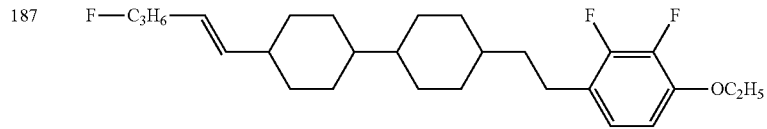 |

| No. | |
|---|---|
| 188 | 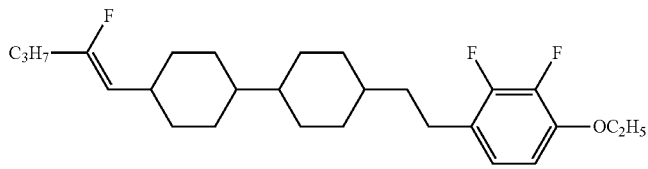 |
| 189 | 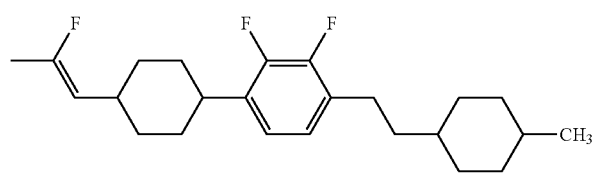 |
| 190 | 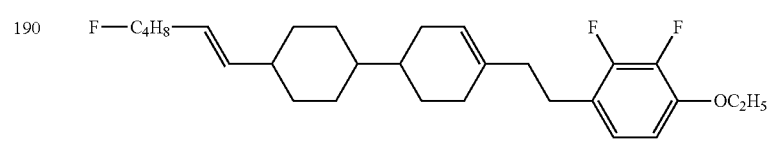 |
| 191 | 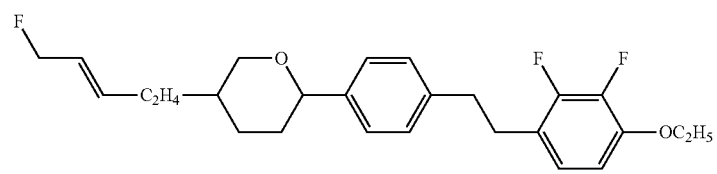 |
| 192 | 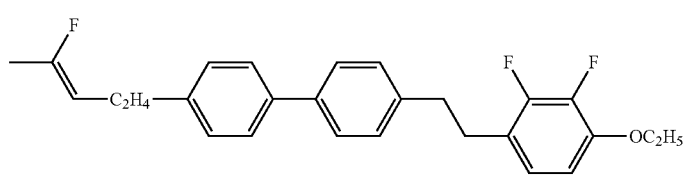 |
| 193 | 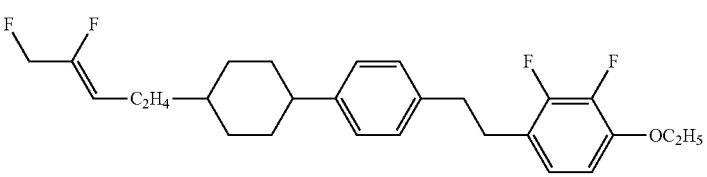 |
| 194 | 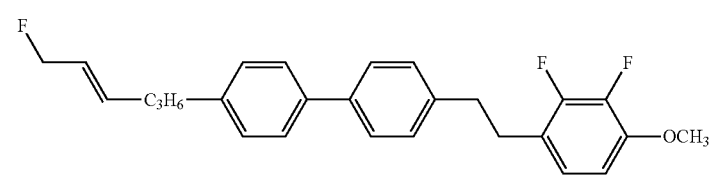 |
| 195 | 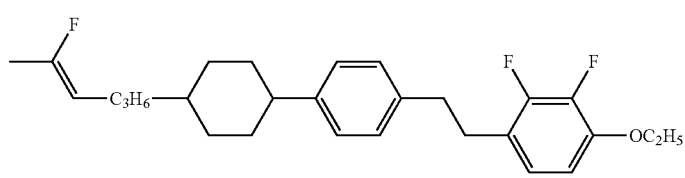 |
| 196 | 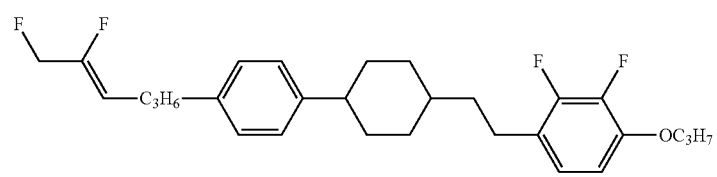 |

-continued
| No. | |
|---|---|
| 197 | 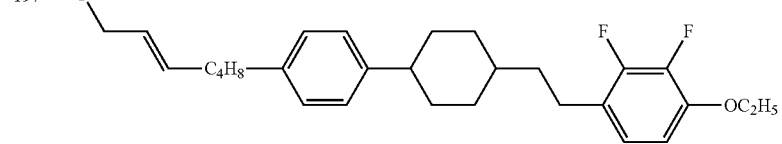 |
| 198 | 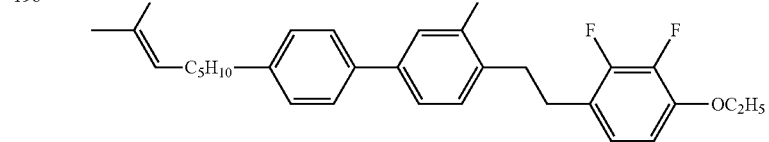 |
| 199 | 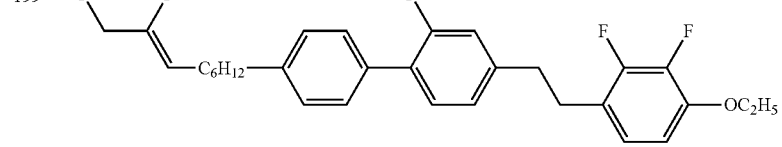 |
| 200 | 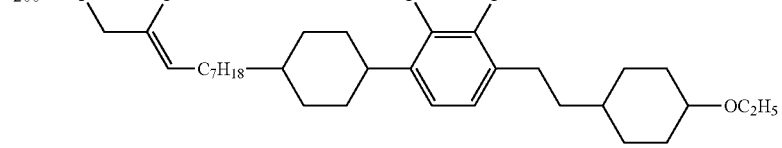 |
| 201 | 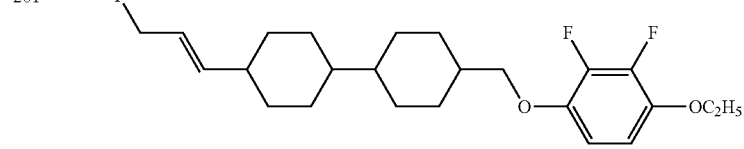 |
| 202 | 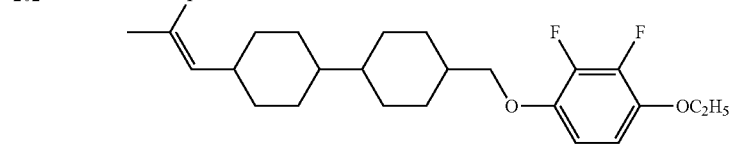 |
| 203 | 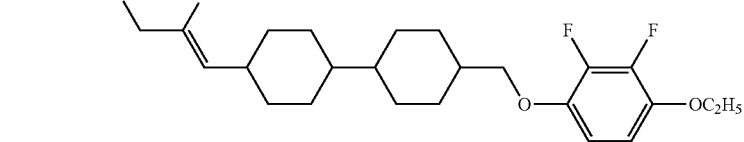 |
| 204 | 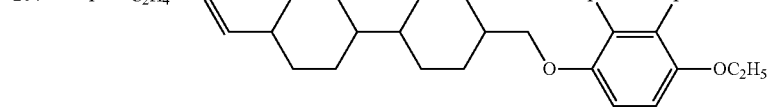 |
| 205 | 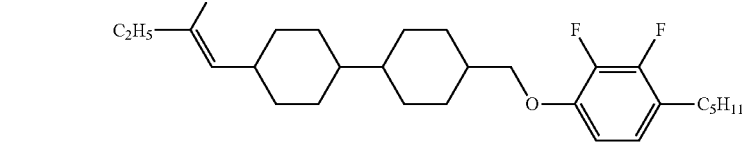 |

| No. | |
|---|---|
| 206 | 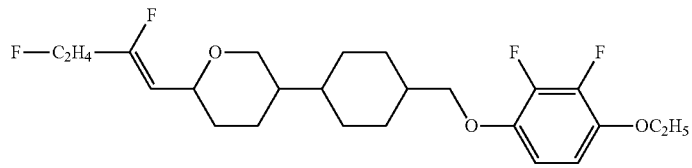 |
| 207 | 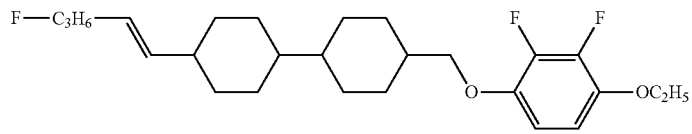 |
| 208 | 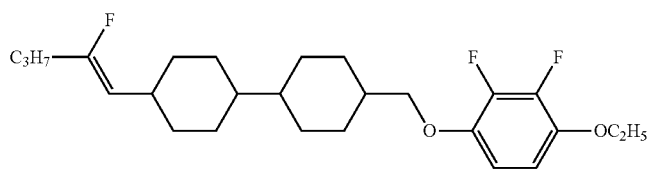 |
| 209 | 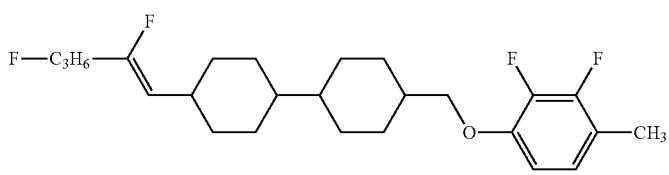 |
| 210 | 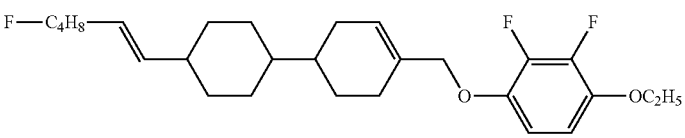 |
| 211 | 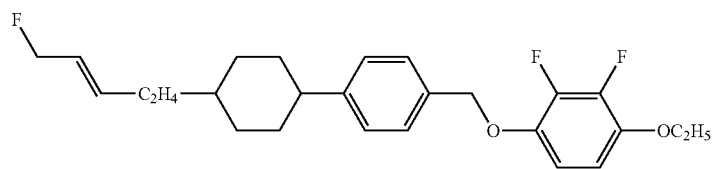 |
| 212 | 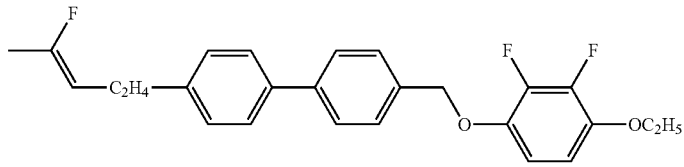 |
| 213 | 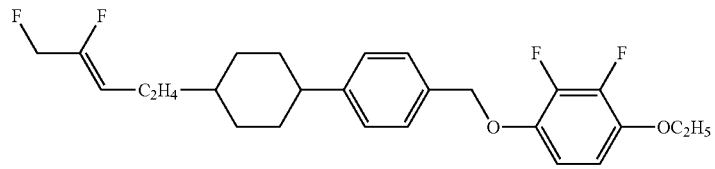 |
| 214 | 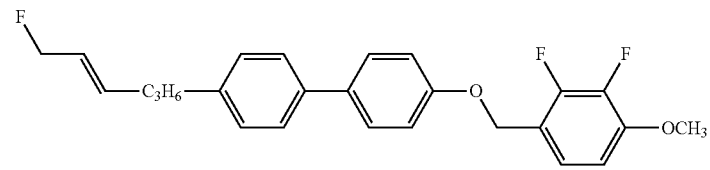 |

| No. | |
|---|---|
| 215 | 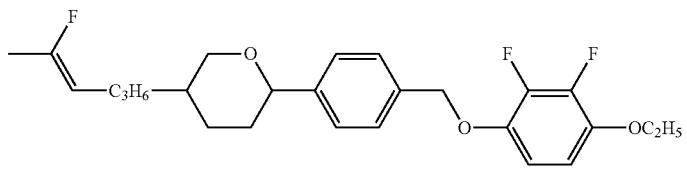 |
| 216 | 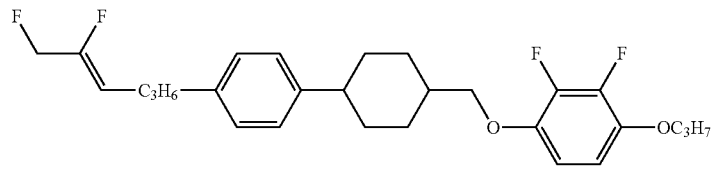 |
| 217 | 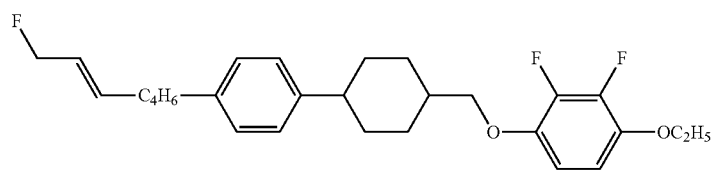 |
| 218 | 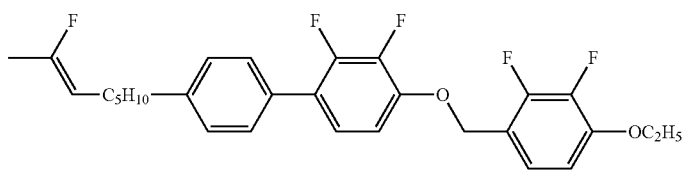 |
| 219 | 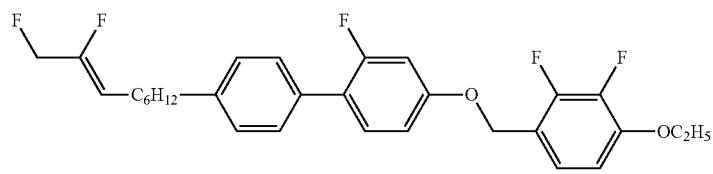 |
| 220 | 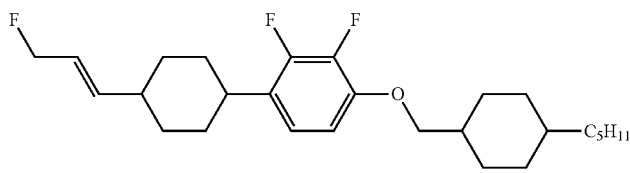 |
| 221 | 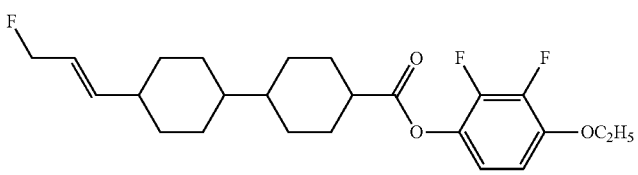 [SMILES: CCOc1ccc(OC(=O)C2CCC(C3CCC(/C=C/CF)CC3)CC2)c(F)c1F] |
| 222 | 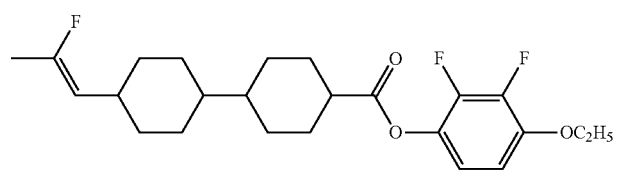 [SMILES: CCOc1ccc(OC(=O)C2CCC(C3CCC(/C=C(/C)F)CC3)CC2)c(F)c1F] |
| 223 | 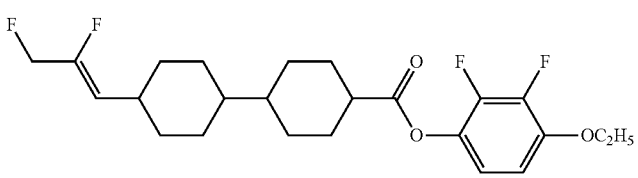 [SMILES: CCOc1ccc(OC(=O)C2CCC(C3CCC(/C=C(\F)CF)CC3)CC2)c(F)c1F] |

-continued
| No. | |
|---|---|
| 224 | 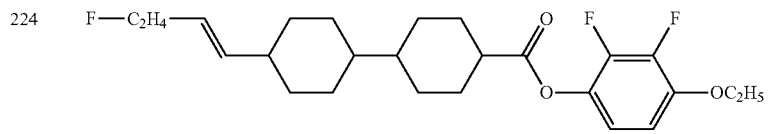 |
| 225 | 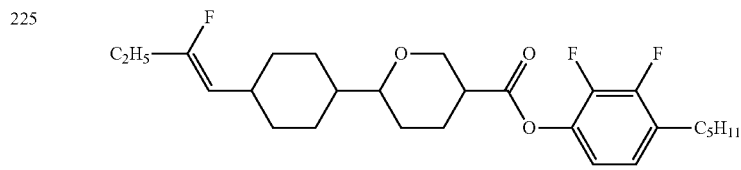 |
| 226 | 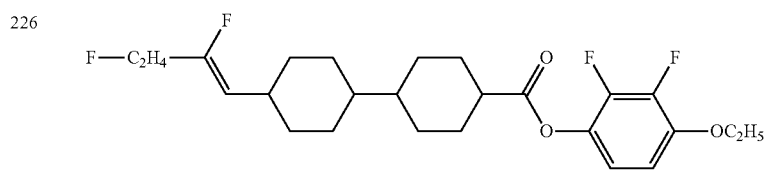 |
| 227 | 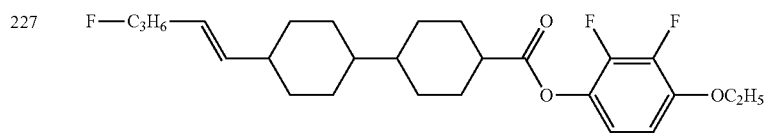 |
| 228 | 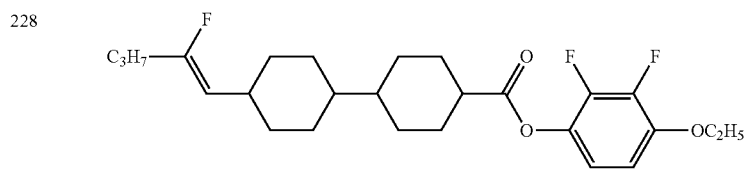 |
| 229 | 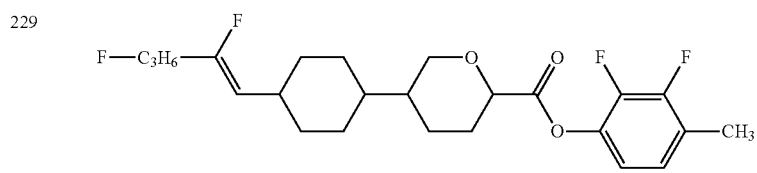 |
| 230 | 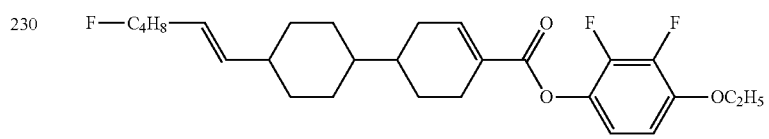 |
| 231 | 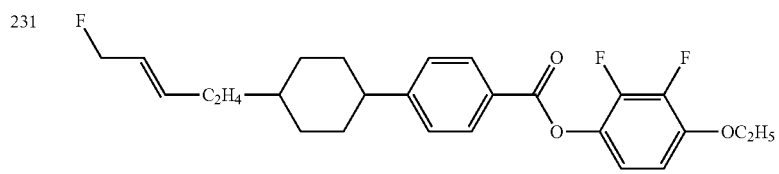 |
| 232 | 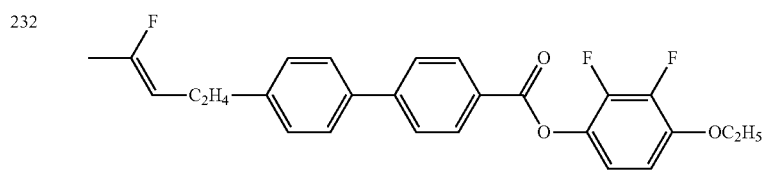 |

| No. | |
|---|---|
| 233 | 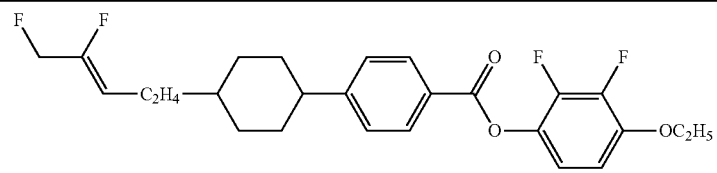 |
| 234 | 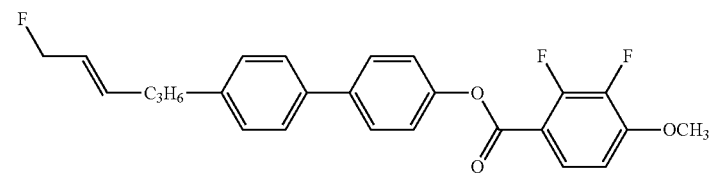 |
| 235 | 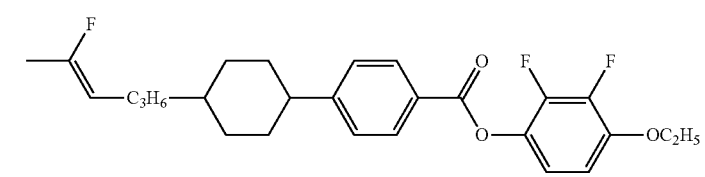 |
| 236 | 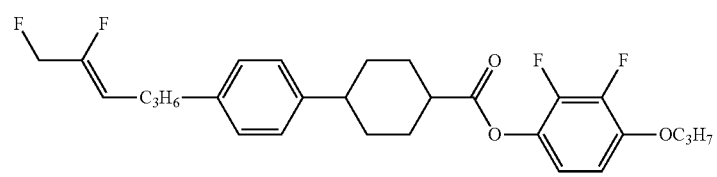 |
| 237 | 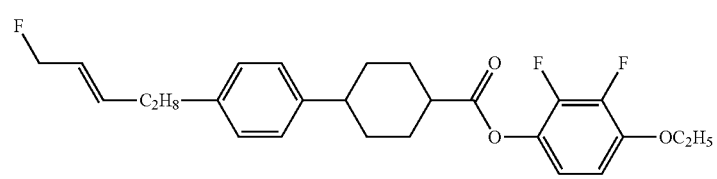 |
| 238 | 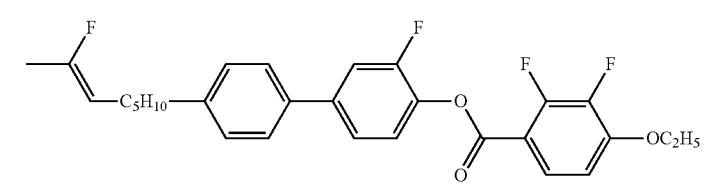 |
| 239 | 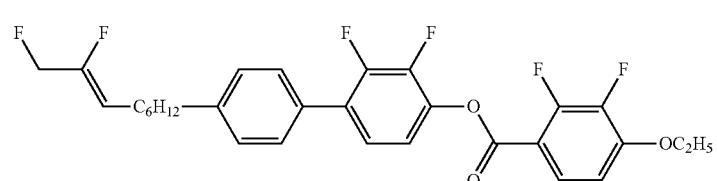 |
| 240 | 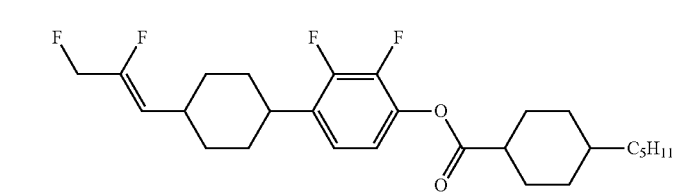 |
| 241 | 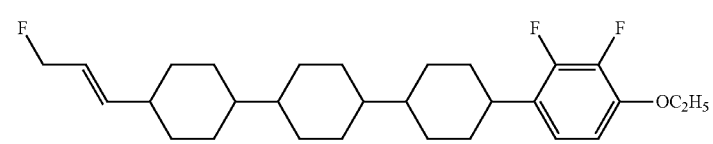 [SMILES: CCOc1ccc(C2CCC(C3CCC(C4CCC(/C=C/CF)CC4)CC3)CC2)c(F)c1F] |

-continued
| No. | |
|---|---|
| 242 | 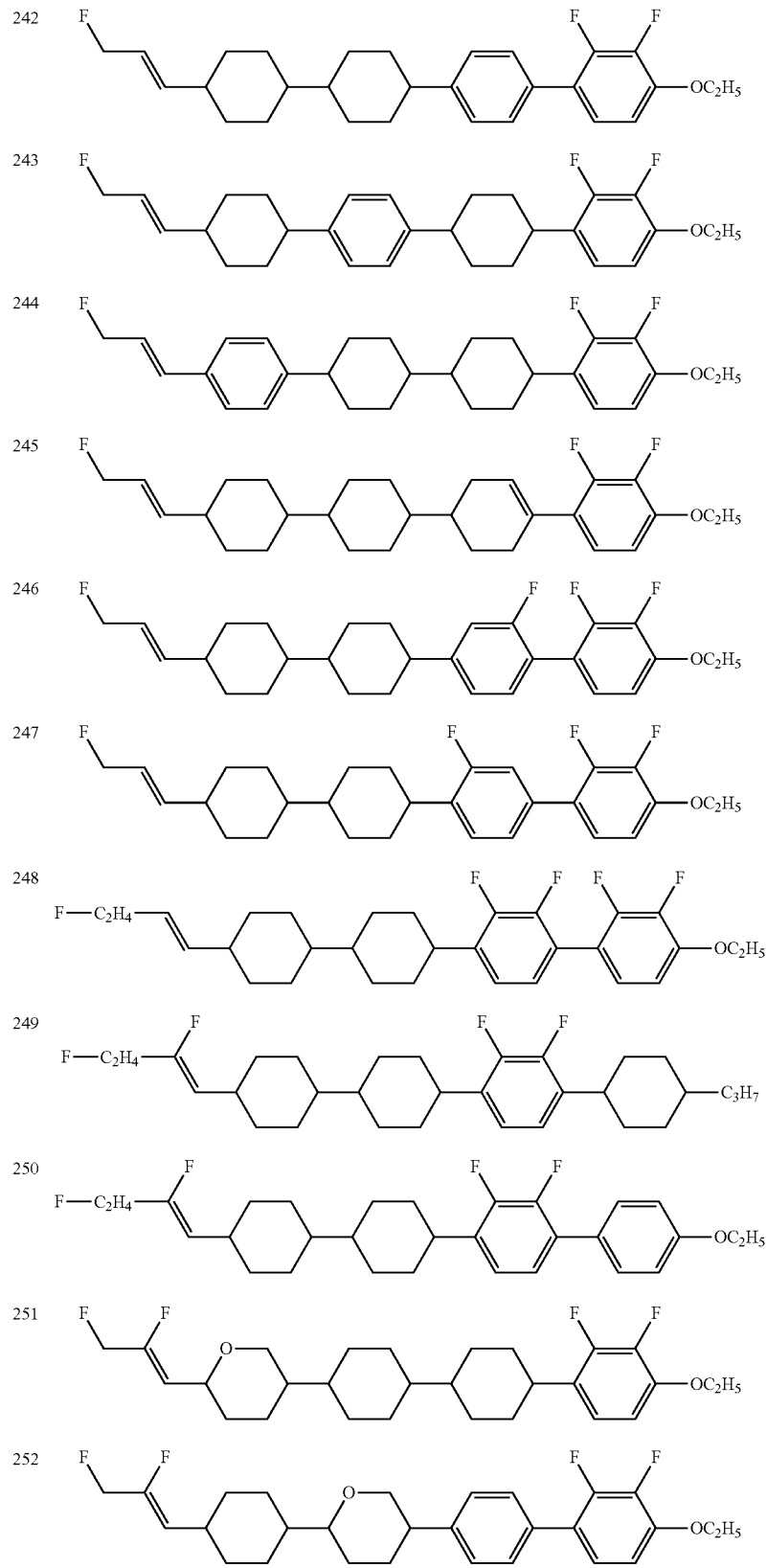 |
| 243 | |
| 244 | |
| 245 | |
| 246 | |
| 247 | |
| 248 | |
| 249 | |
| 250 | |
| 251 | |
| 252 | |

| No. | |
|---|---|
| 253 | 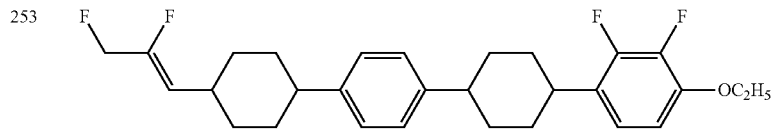 |
| 254 | 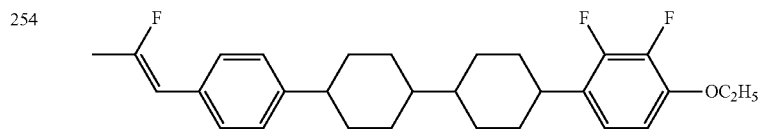 |
| 255 | 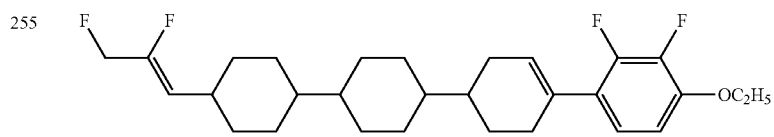 |
| 256 | 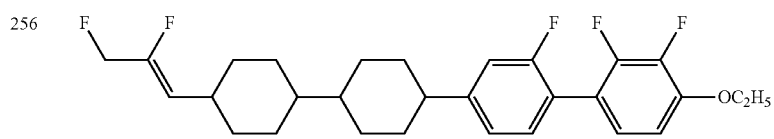 |
| 257 | 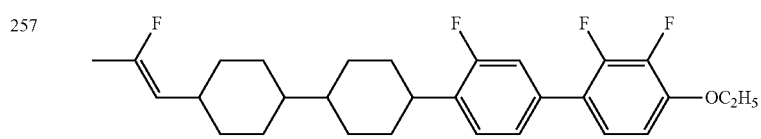 |
| 258 | 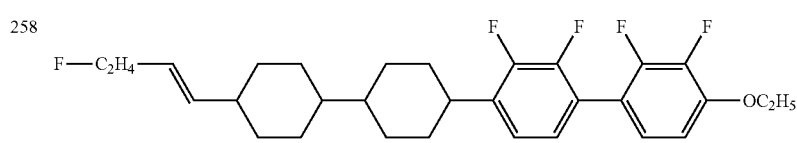 |
| 259 | 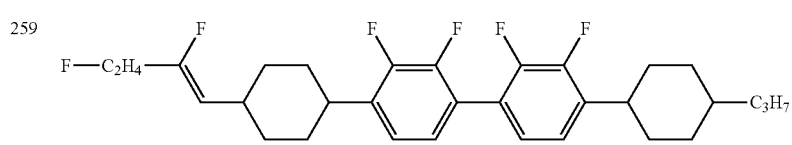 |
| 260 | 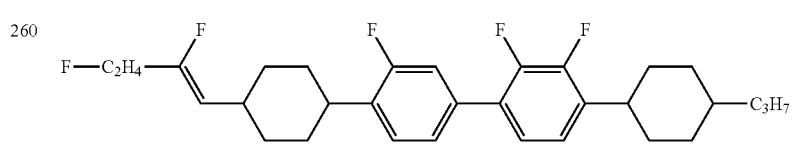 |
| 261 | 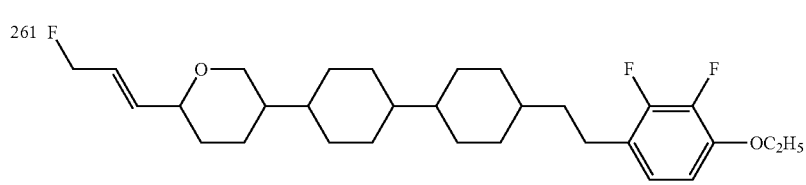 |
| 262 | 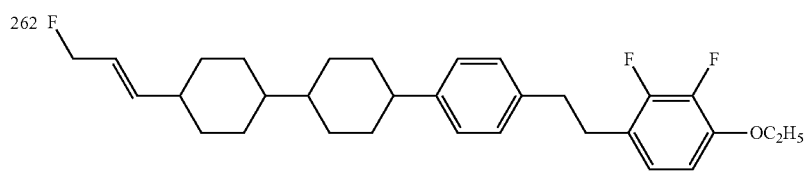 |

| No. | |
|---|---|
| 263 | 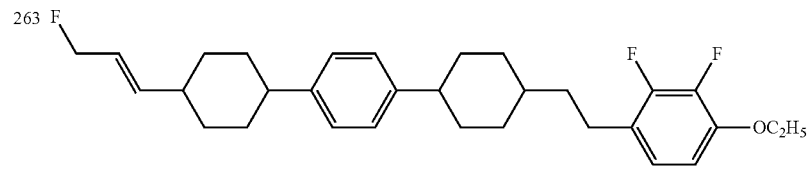 |
| 264 | 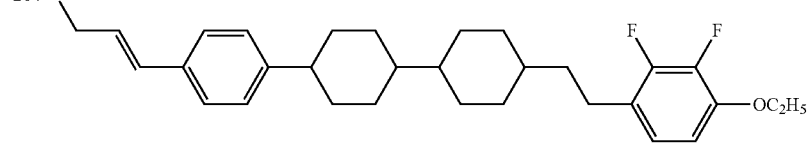 |
| 265 | 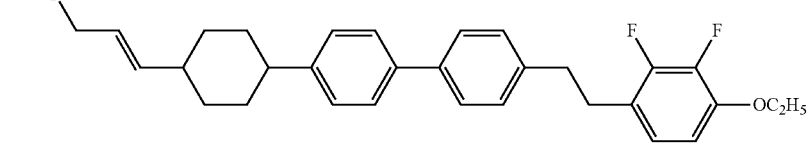 |
| 266 | 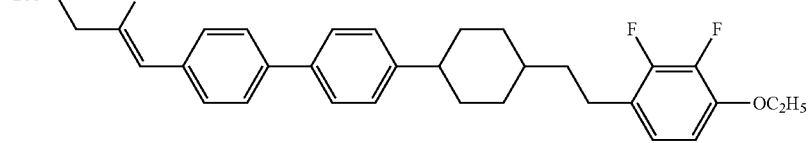 |
| 267 | 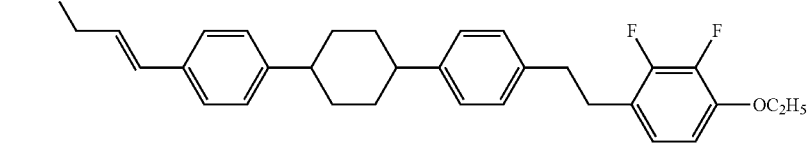 |
| 268 | 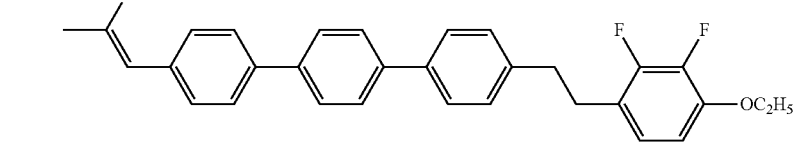 |
| 269 | 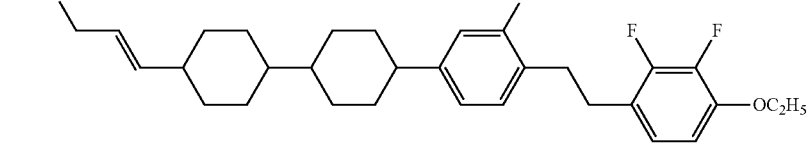 |
| 270 | 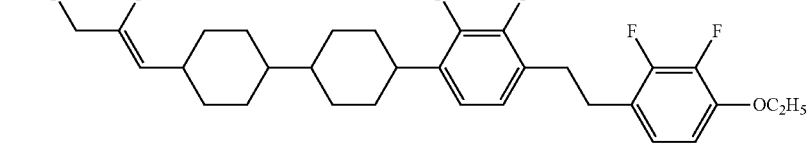 |
| 271 | 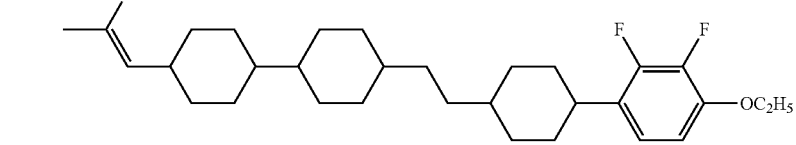 |

| No. |
|---|
| 272 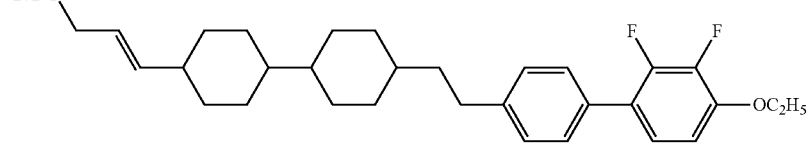 |
| 273 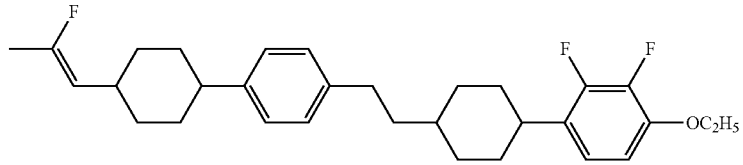 [SMILES: CCOc1ccc(C2CCC(COc3ccc(C4CCC(/C=C(/C)F)CC4)cc3)CC2)c(F)c1F] |
| 274 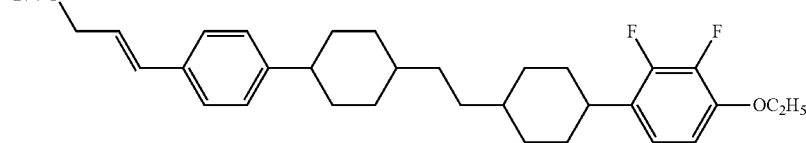 |
| 275 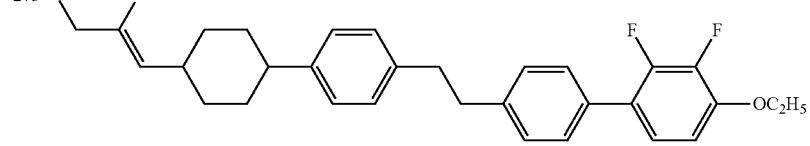 |
| 276 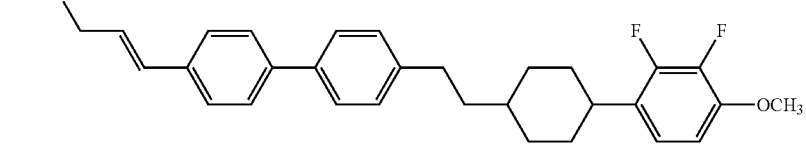 |
| 277 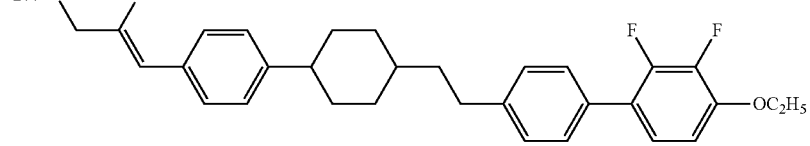 |
| 278 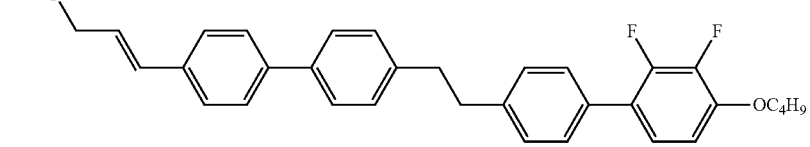 |
| 279 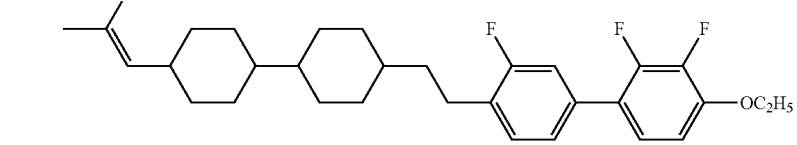 |
| 280 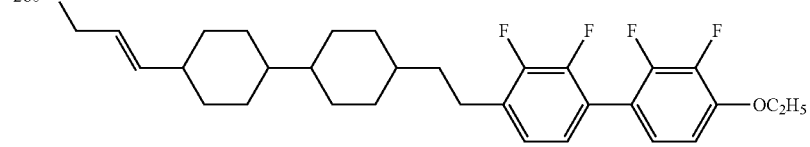 |

| No. |
|---|
| 281 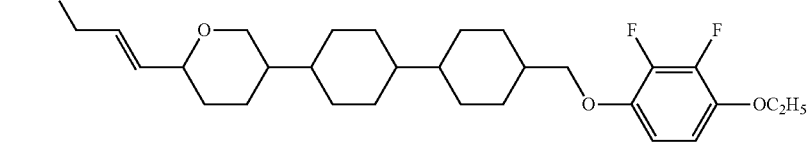 |
| 282 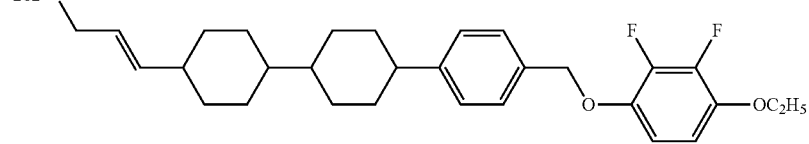 |
| 283 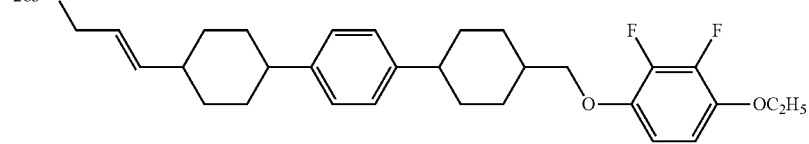 |
| 284 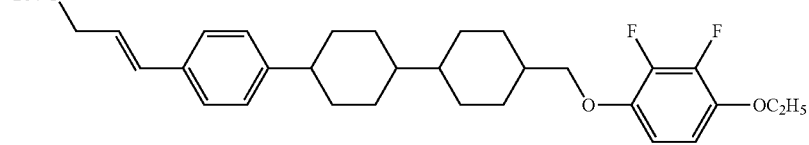 |
| 285 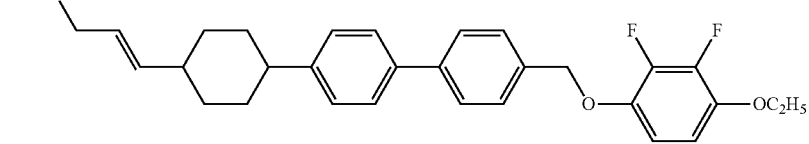 |
| 286 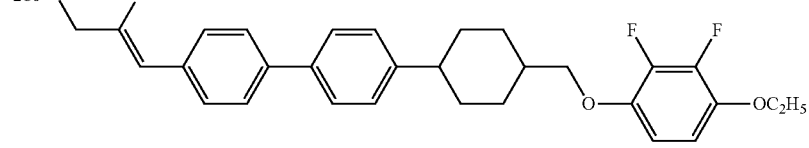 |
| 287 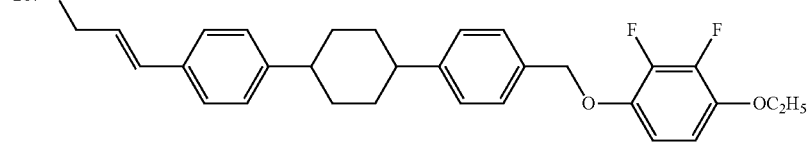 |
| 288 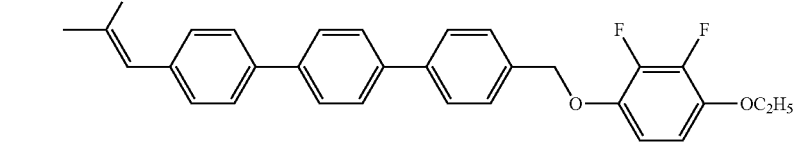 |
| 289 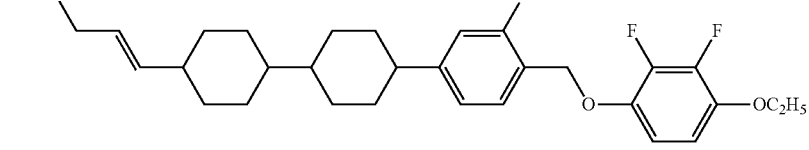 |

| No. |
|---|
| 290 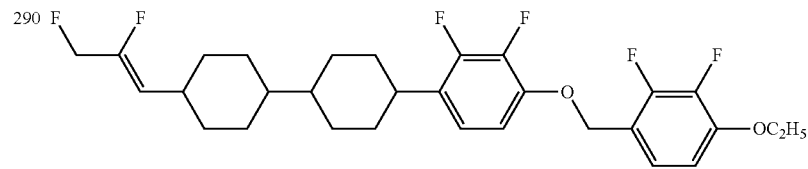 |
| 291 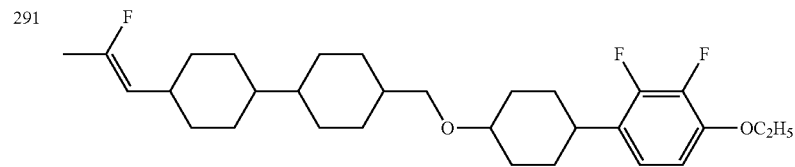 |
| 292 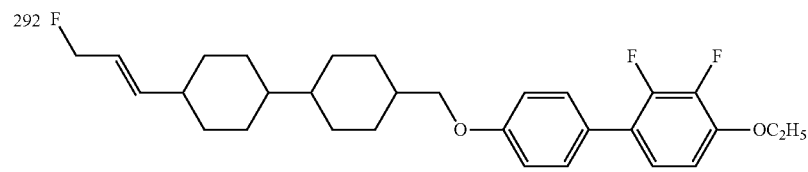 |
| 293 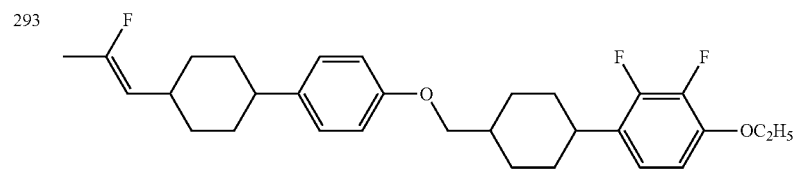 |
| 294 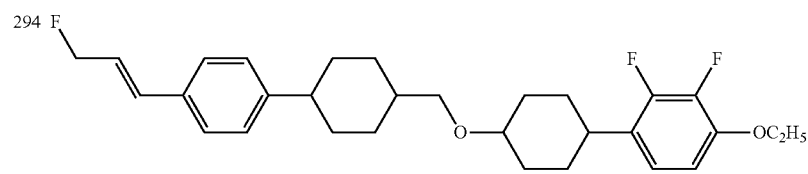 |
| 295 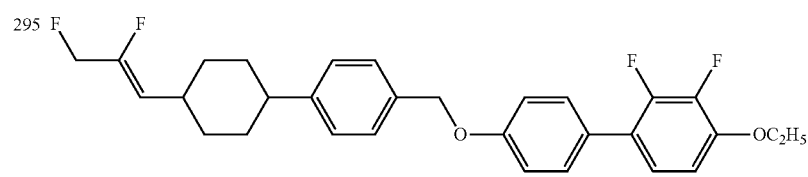 |
| 296 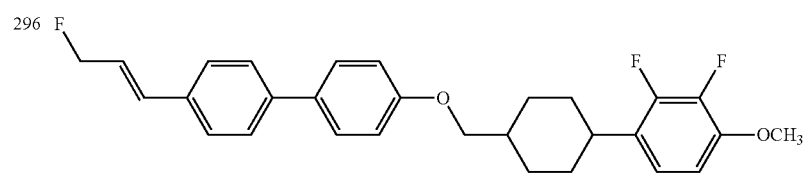 |
| 297 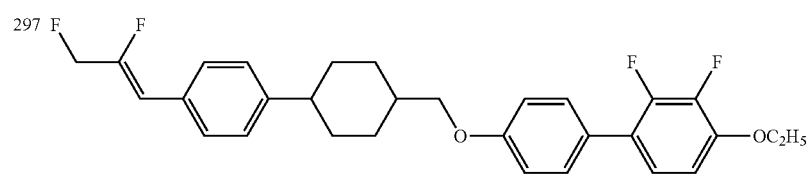 |
| 298 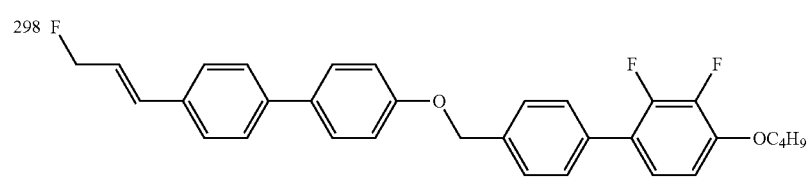 |

| No. |
|---|
| 299 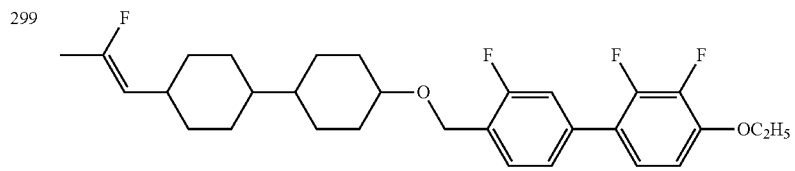 |
| 300 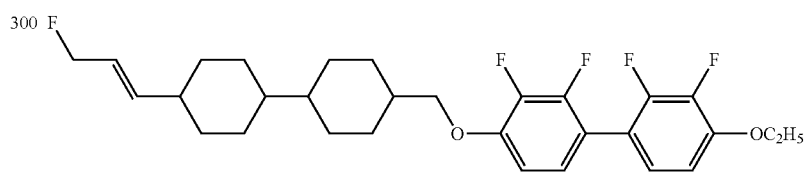 |
| 301 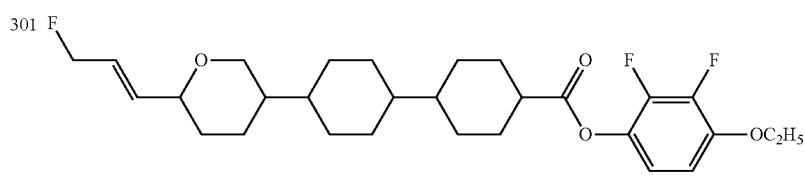 |
| 302 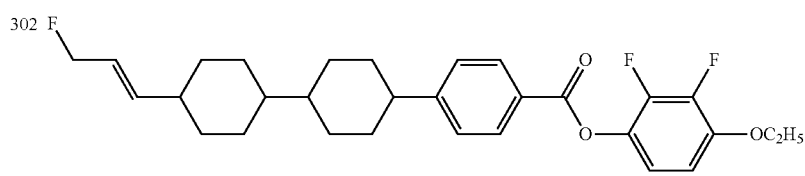 |
| 303 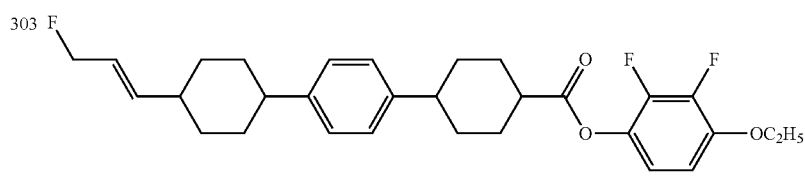 |
| 304 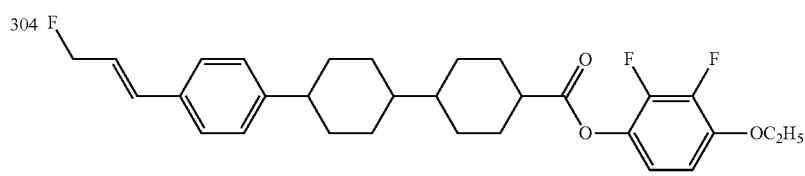 |
| 305 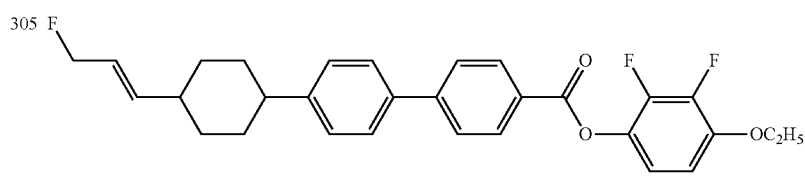 |
| 306 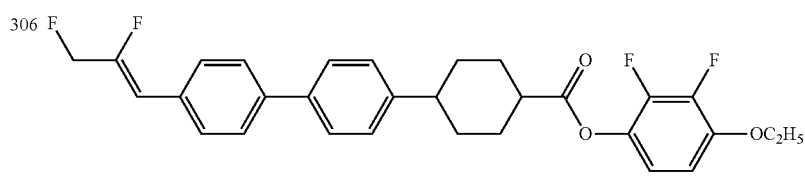 |
| 307 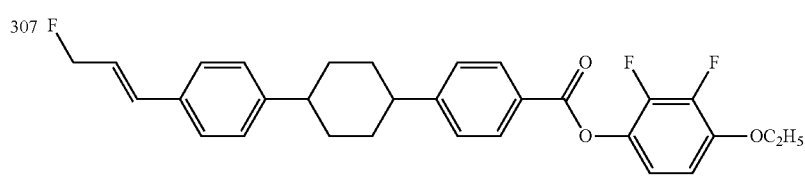 |

-continued
| No. | |
|---|---|
| 308 | 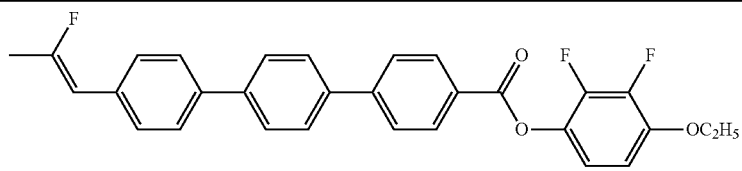 |
| 309 | 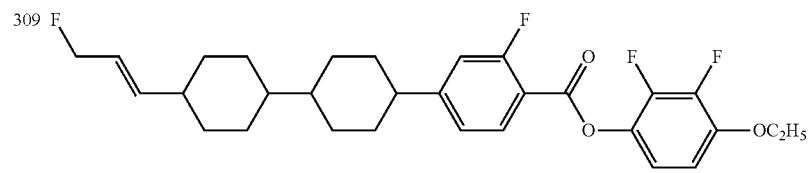 |
| 310 | 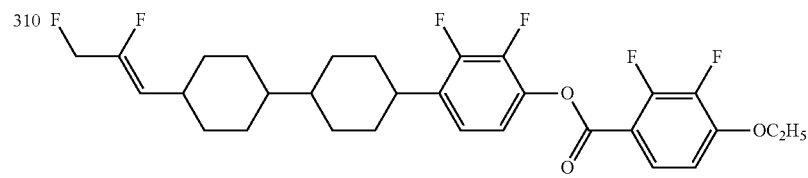 |
| 311 | 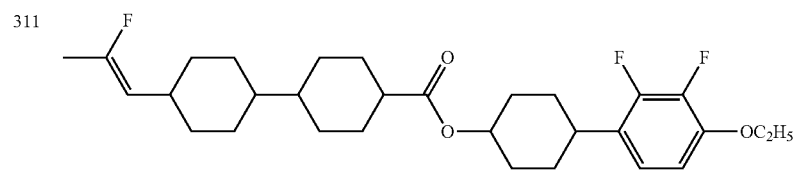 |
| 312 | 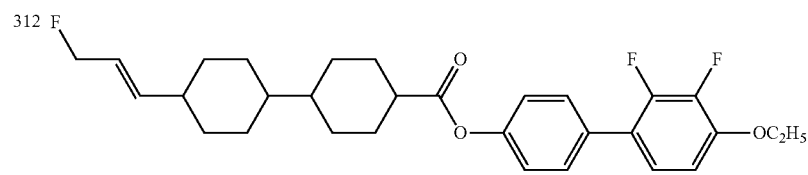 |
| 313 | 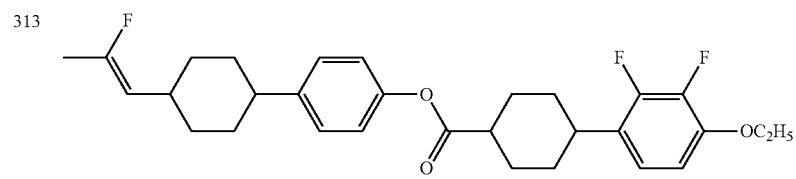 |
| 314 | 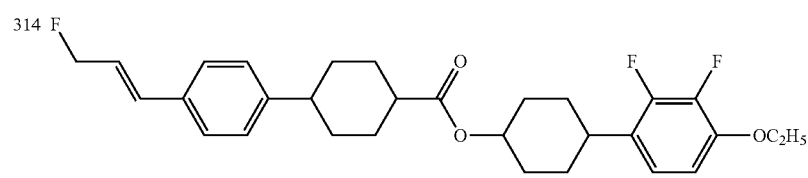 |
| 315 | 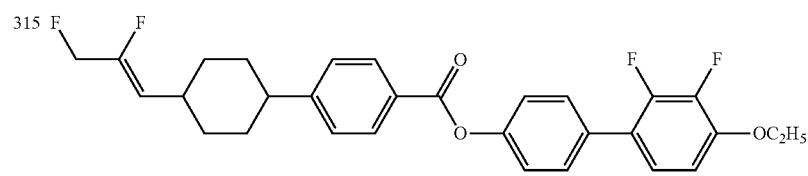 |
| 316 | 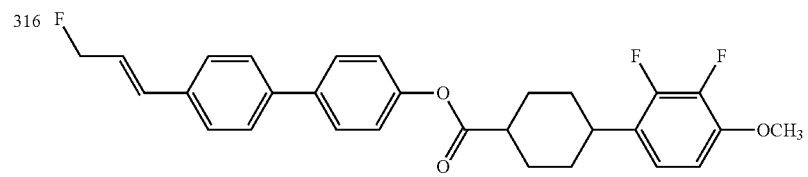 |

| No. | |
|---|---|
| 317 | 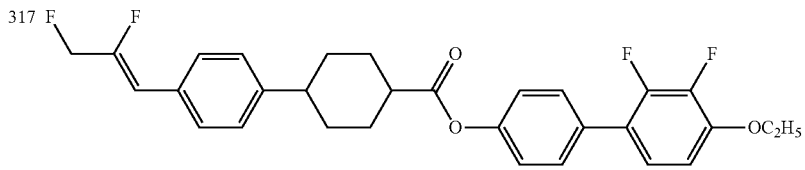 |
| 318 | 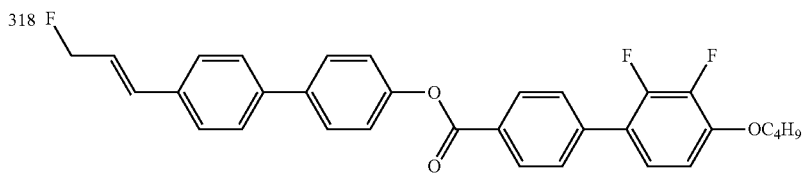 |
| 319 | 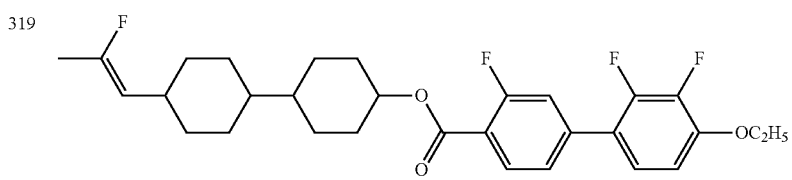 |
| 320 | 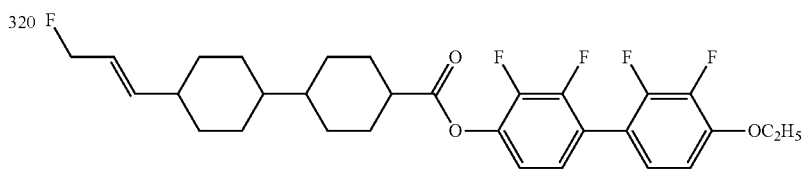 |

1-2. Example of Composition (1)

Liquid crystal composition (1) of the invention will be described in detail by way of Examples. Compounds described in Examples were expressed using symbols according to definitions in the Table below. In the Table, a configuration of 1,4-cyclohexylene is trans. A parenthesized number next to a symbolized compound in Examples corresponds to the number of the compound. A symbol (-) means any other liquid crystal compound. A ratio (percentage) of a liquid crystal compound is expressed in terms of weight percentage (% by weight) based on the total weight of the liquid crystal composition. Values of physical properties of the composition were summarized in a last part. The physical properties were measured according to the methods described above, and were directly described without extrapolating the measured values.

TABLE

Methods for Description of Compounds using Symbols
R—(A$_1$)—Z$_1$—...—Z$_n$—(A$_n$)—R'

| 1) Left-terminal Group R— | Symbol |
|---|---|
| C$_n$H$_{2n+1}$— | n- |
| C$_n$H$_{2n+1}$O— | nO— |
| C$_m$H$_{2m+1}$OC$_n$H$_{2n}$— | mOn— |
| CH$_2$=CH— | V— |
| C$_n$H$_{2n+1}$—CH=CH— | nV— |
| CH$_2$=CH—C$_n$H$_{2n}$— | Vn— |
| C$_m$H$_{2m+1}$—CH=CH—C$_n$H$_{2n}$— | mVn— |
| CF$_2$=CH— | VFF— |
| CF$_2$=CH—C$_n$H$_{2n}$— | VFFn— |
| F—C$_n$H$_{2n}$—CH=CH— | FnV— |

TABLE-continued

Methods for Description of Compounds using Symbols
R—(A$_1$)—Z$_1$—...—Z$_n$—(A$_n$)—R'

| | |
|---|---|
| C$_n$H$_{2n+1}$—CF=CH— | nFV— |
| F—C$_n$H$_{2n}$—CF=CH— | FnFV— |

| 2) Right-terminal Group —R' | Symbol |
|---|---|
| —C$_n$H$_{2n+1}$ | -n |
| —OC$_n$H$_{2n+1}$ | —On |
| —COOCH$_3$ | —EMe |
| —CH=CH$_2$ | —V |
| —CH=CH—C$_n$H$_{2n+1}$ | —Vn |
| —C$_n$H$_{2n}$—CH=CH$_2$ | —nV |
| —C$_m$H$_{2m}$—CH=CH—C$_n$H$_{2n+1}$ | —mVn |
| —CH=CF$_2$ | —VFF |
| —F | —F |
| —Cl | —CL |
| —OCF$_3$ | —OCF3 |
| —OCF$_2$H | —OCF2H |
| —CF$_3$ | —CF3 |
| —CF=CH—CF$_3$ | —FVCF3 |

| 3) Bonding Group —Z$_n$— | Symbol |
|---|---|
| —C$_n$H$_{2n}$— | n |
| —COO— | E |
| —CH=CH— | V |
| —CH$_2$O— | 1O |
| —OCH$_2$— | O1 |

| 4) Ring Structure —A$_n$— | Symbol |
|---|---|
| ⬡ | H |

TABLE-continued

Methods for Description of Compounds using Symbols
R—(A₁)—Z₁—...—Zₙ—(Aₙ)—R'

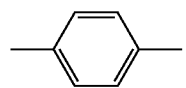 B

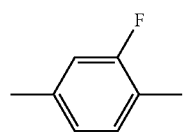 B(F)

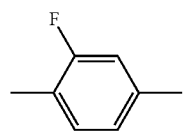 B(2F)

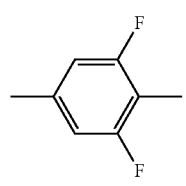 B(F,F)

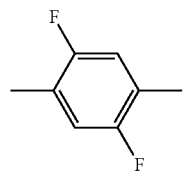 B(2F,5F)

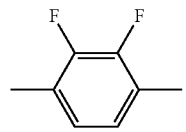 B(2F,3F)

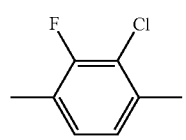 B(2F,3CL)

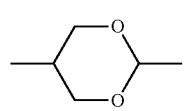 G

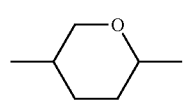 dh

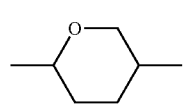 Dh

TABLE-continued

Methods for Description of Compounds using Symbols
R—(A₁)—Z₁—...—Zₙ—(Aₙ)—R'

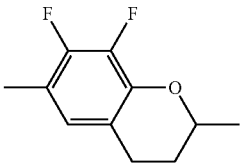 Cro(7F,8F)

5) Examples of Description

Example 1 F1V—HBB(2F,3F)—O2

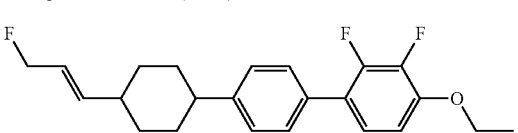

Example 2 F1FV—HBB(2F,3F)—O2

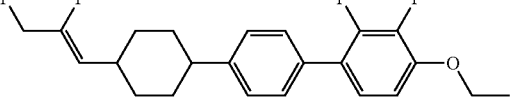

Example 3 3HH-4

Example 4 3-HBB(2F,3F)—O2

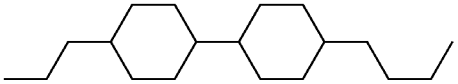 [SMILES: CCCCC1CCC(C2CCC(CCC)CC2)CC1]

Example 6

| | | |
|---|---|---|
| F1V-HBB(2F,3F)-O2 | (No. 141) | 5% |
| 3-HB-O1 | (13-5) | 13% |
| 3-HH-4 | (13-1) | 5% |
| 3-HB(2F,3F)-O2 | (6-1) | 11% |
| 5-HB(2F,3F)-O2 | (6-1) | 11% |
| 2-HHB(2F,3F)-1 | (7-1) | 11% |
| 3-HHB(2F,3F)-1 | (7-1) | 12% |
| 3-HHB(2F,3F)-O2 | (7-1) | 13% |
| 5-HHB(2F,3F)-O2 | (7-1) | 13% |
| 3-HHB-1 | (14-1) | 6% |

NI = 93.7° C.; Δn = 0.096; Δε = −3.6; η = 37.4 mPa·s.

Example 7

| | | |
|---|---|---|
| 1FV-HBB(2F,3F)-O2 | (No. 142) | 3% |
| 3-HH-4 | (13-1) | 7% |
| 3-H2B(2F,3F)-O2 | (6-4) | 22% |
| 5-H2B(2F,3F)-O2 | (6-4) | 22% |
| 2-HHB(2F,3CL)-O2 | (7-12) | 2% |
| 3-HHB(2F,3CL)-O2 | (7-12) | 3% |
| 4-HHB(2F,3CL)-O2 | (7-12) | 2% |

-continued

| | | |
|---|---|---|
| 5-HHB(2F,3CL)-O2 | (7-12) | 2% |
| 3-HBB(2F,3F)-O2 | (7-7) | 8% |
| 5-HBB(2F,3F)-O2 | (7-7) | 8% |
| V-HHB-1 | (14-1) | 6% |
| 3-HHB-3 | (14-1) | 6% |
| 3-HHEBH-3 | (15-6) | 3% |
| 3-HHEBH-4 | (15-6) | 3% |
| 3-HHEBH-5 | (15-6) | 3% |

NI = 92.2° C.; $\Delta n = 0.102$; $\Delta \epsilon = -4.1$; $\eta = 30.4$ mPa·s.

Example 8

| | | |
|---|---|---|
| F1FV-HBB(2F,3F)-O2 | (No. 143) | 5% |
| 2-HH-5 | (13-1) | 3% |
| 3-HH-4 | (13-1) | 12% |
| 3-HH-5 | (13-1) | 4% |
| 3-HB-O2 | (13-5) | 10% |
| 3-H2B(2F,3F)-O2 | (6-4) | 15% |
| 5-H2B(2F,3F)-O2 | (6-4) | 15% |
| 3-HHB(2F,3CL)-O2 | (7-12) | 5% |
| 2-HBB(2F,3F)-O2 | (7-7) | 3% |
| 3-HBB(2F,3F)-O2 | (7-7) | 9% |
| 5-HBB(2F,3F)-O2 | (7-7) | 9% |
| 3-HHB-1 | (14-1) | 3% |
| 3-HHB-3 | (14-1) | 4% |
| 3-HHB-O1 | (14-1) | 3% |

NI = 80.4° C.; $\Delta n = 0.100$; $\Delta \epsilon = -4.4$; $\eta = 23.7$ mPa·s.

Example 9

| | | |
|---|---|---|
| F1V-HB(2F,3F)-O2 | (No. 1) | 5% |
| 2-HH-3 | (13-1) | 18% |
| 3-HH-4 | (13-1) | 9% |
| 1-BB-5 | (13-8) | 9% |
| 3-HB-O2 | (13-5) | 2% |
| 3-BB(2F,3F)-O2 | (6-3) | 9% |
| 5-BB(2F,3F)-O2 | (6-3) | 6% |
| 2-HH1OB(2F,3F)-O2 | (7-5) | 13% |
| 3-HH1OB(2F,3F)-O2 | (7-5) | 19% |
| 3-HHB-1 | (14-1) | 5% |
| 3-HHB-O1 | (14-1) | 3% |
| 2-BBB(2F)-5 | (14-8) | 2% |

Example 10

| | | |
|---|---|---|
| F3V-HHB(2F,3F)-O2 | (No. 147) | 5% |
| 2-HH-3 | (13-1) | 15% |
| 7-HB-1 | (13-5) | 10% |
| 5-HB-O2 | (13-5) | 8% |
| 3-HB(2F,3F)-O2 | (6-1) | 15% |
| 5-HB(2F,3F)-O2 | (6-1) | 14% |
| 3-HHB(2F,3CL)-O2 | (7-12) | 3% |
| 4-HHB(2F,3CL)-O2 | (7-12) | 3% |
| 5-HHB(2F,3CL)-O2 | (7-12) | 2% |
| 3-HH1OCro(7F,8F)-5 | (10-12) | 5% |
| 5-HBB(F)B-2 | (15-5) | 10% |
| 5-HBB(F)B-3 | (15-5) | 10% |

Example 11

| | | |
|---|---|---|
| F1V-HBB(2F,3F)-O2 | (No. 141) | 5% |
| 1-BB-3 | (13-8) | 10% |
| 3-HH-V | (13-1) | 26% |
| 3-BB(2F,3F)-O2 | (6-3) | 11% |
| 2-HH1OB(2F,3F)-O2 | (7-5) | 20% |
| 3-HH1OB(2F,3F)-O2 | (7-5) | 14% |
| 3-HHB-1 | (14-1) | 8% |
| 2-BBB(2F)-2 | (14-8) | 6% |

NI = 81.9° C.; $\Delta n = 0.112$; $\Delta \epsilon = -3.2$; $\eta = 17.6$ mPa·s.

Example 12

| | | |
|---|---|---|
| 1FV-HBB(2F,3F)-O2 | (No. 142) | 5% |
| 2-HH-3 | (13-1) | 6% |
| 3-HH-V1 | (13-1) | 9% |
| 1V2-HH-1 | (13-1) | 8% |
| 1V2-HH-3 | (13-1) | 7% |
| 3-BB(2F,3F)-O2 | (6-3) | 8% |
| 5-BB(2F,3F)-O2 | (6-3) | 4% |
| 3-H1OB(2F,3F)-O2 | (6-5) | 7% |
| 2-HH1OB(2F,3F)-O2 | (7-5) | 8% |
| 3-HH1OB(2F,3F)-O2 | (7-5) | 16% |
| 3-HDhB(2F,3F)-O2 | (7-3) | 7% |
| 3-HHB-1 | (14-1) | 3% |
| 3-HHB-3 | (14-1) | 2% |
| 2-BB(2F,3F)B-3 | (8-1) | 10% |

NI = 85.6° C.; $\Delta n = 0.111$; $\Delta \epsilon = -4.4$; $\eta = 23.3$ mPa·s.

Example 13

| | | |
|---|---|---|
| F3V-HB(2F,3F)-O2 | (No. 7) | 5% |
| 2-HH-3 | (13-1) | 18% |
| 3-HH-4 | (13-1) | 9% |
| 1-BB-5 | (13-8) | 9% |
| 3-HB-O2 | (13-5) | 2% |
| 3-BB(2F,3F)-O2 | (6-3) | 9% |
| 5-BB(2F,3F)-O2 | (6-3) | 6% |
| 2-HH1OB(2F,3F)-O2 | (7-5) | 13% |
| 3-HH1OB(2F,3F)-O2 | (7-5) | 19% |
| 3-HHB-1 | (14-1) | 5% |
| 3-HHB-O1 | (14-1) | 3% |
| 2-BBB(2F)-5 | (14-8) | 2% |

Example 14

| | | |
|---|---|---|
| F3V2-HB(2F,3F)-O2 | (No. 20) | 5% |
| 2-HH-3 | (13-1) | 18% |
| 3-HH-4 | (13-1) | 9% |
| 1-BB-5 | (13-8) | 9% |
| 3-HB-O2 | (13-5) | 2% |
| 3-BB(2F,3F)-O2 | (6-3) | 9% |
| 5-BB(2F,3F)-O2 | (6-3) | 6% |
| 2-HH1OB(2F,3F)-O2 | (7-5) | 13% |
| 3-HH1OB(2F,3F)-O2 | (7-5) | 19% |
| 3-HHB-1 | (14-1) | 5% |
| 3-HHB-O1 | (14-1) | 3% |
| 2-BBB(2F)-5 | (14-8) | 2% |

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

INDUSTRIAL APPLICABILITY

A liquid crystal compound of the invention has a high stability to heat, light and so forth, a high clearing point, a low minimum temperature of a liquid crystal phase, a small viscosity, a suitable optical anisotropy, a large negative dielectric anisotropy, a suitable elastic constant and an excellent compatibility with other liquid crystal compounds. A liquid crystal composition of the invention contains the compound, and has a high maximum temperature of a nematic phase, a low minimum temperature of the nematic phase, a small viscosity, a suitable optical anisotropy, a large negative dielectric anisotropy, and a suitable elastic constant. The composition has a suitable balance regarding at least two of physical properties. A liquid crystal display device of the invention includes the composition, and has a wide temperature range in which the device can be used, a short response time, a large voltage holding ratio, a low threshold voltage, a large contrast ratio and a long service life. Therefore, the device can be widely applied to a display of a personal computer, a television and so forth.

What is claimed is:

1. A compound represented by formula (1):

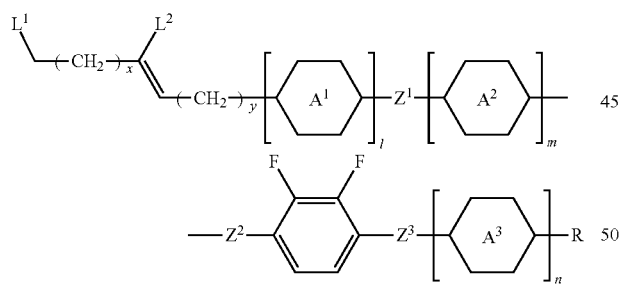

(1)

wherein, in formula (1),

R is hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;

ring $A^1$, ring $A^2$ and ring $A^3$ are independently 1,4-cyclohexylene, 1,4-cyclohexenylene, tetrahydropyran-2,5-diyl, 1,3-dioxane-2,5-diyl, pyrimidine-2,5-diyl, pyridine-2,5-diyl, naphthalene-2,6-diyl, decahydronaphthalene-2,6-diyl, 1,2,3,4-tetrahydronaphthalene-2,6-diyl, 1,4-phenylene, 2-fluoro-1,4-phenylene or 2,3-difluoro-1,4-phenylene;

$L^1$ and $L^2$ are independently hydrogen, fluorine or chlorine, and at least one of $L^1$ and $L^2$ is fluorine;

$Z^1$, $Z^2$, and $Z^3$ are independently a single bond, —$(CH_2)_2$—, —$CH_2O$—, —$OCH_2$—, —COO—, —OCO—, —$CF_2O$—, or —$OCF_2$—;

x and y are independently an integer from 0 to 10; and l and m are independently 0, 1 or 2, and n is independently 1 or 2, and a sum of l, m and n is 1, 2 or 3.

2. The compound according to claim 1, represented by formula (1-1):

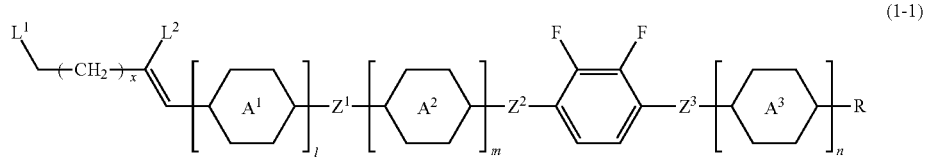

(1-1)

wherein, in formula (1-1),

R is hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;

ring $A^1$, ring $A^2$ and ring $A^3$ are independently 1,4-cyclohexylene, 1,4-cyclohexenylene, tetrahydropyran-2,5-diyl, 1,3-dioxane-2,5-diyl, pyridine-2,5-diyl, naphthalene-2,6-diyl, 1,4-phenylene, 2-fluoro-1,4-phenylene or 2,3-difluoro-1,4-phenylene;

$L^1$ and $L^2$ are independently hydrogen, fluorine or chlorine, and at least one of $L^1$ and $L^2$ is fluorine;

$Z^1$, $Z^2$, and $Z^3$ are independently a single bond, —$(CH_2)_2$—, —$CH_2O$—, —$OCH_2$—, —COO— or —OCO—;

x is an integer from 0 to 10; and l, m and n are independently 0, 1 or 2, and a sum of l, m and n is 1, 2 or 3.

3. The compound according to claim 1, represented by formula (1-2):

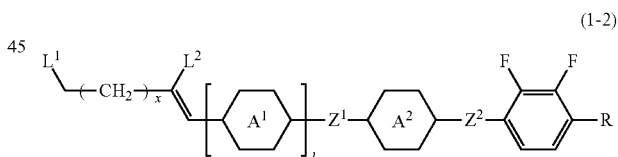

(1-2)

wherein, in formula (1-2),

R is hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;

ring $A^1$ and ring $A^2$ are independently 1,4-cyclohexylene, 1,4-cyclohexenylene, tetrahydropyran-2,5-diyl, 1,4-phenylene, 2-fluoro-1,4-phenylene or 2,3-difluoro-1,4-phenylene;

$L^1$ and $L^2$ are independently hydrogen or fluorine, at least one of $L^1$ and $L^2$ is fluorine;

$Z^1$ and $Z^2$ are independently a single bond, —$(CH_2)_2$—, —$CH_2O$—, —$OCH_2$—, —COO— or —OCO—; and l is 0 or 1 and x is an integer from 0 to 10.

4. The compound according to claim 1, represented by formula (1-3):

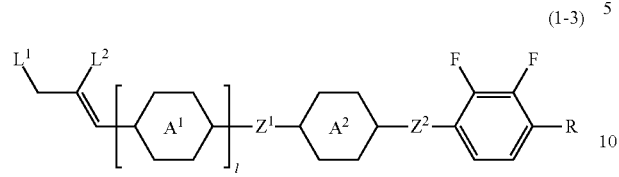
(1-3)

wherein, in formula (1-3),
R is hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;
ring $A^1$ and ring $A^2$ are independently 1,4-cyclohexylene, 1,4-cyclohexenylene, tetrahydropyran-2,5-diyl, 1,4-phenylene, 2-fluoro-1,4-phenylene or 2,3-difluoro-1,4-phenylene;
$L^1$ and $L^2$ are independently hydrogen or fluorine, and at least one of $L^1$ and $L^2$ is fluorine;
$Z^1$ and $Z^2$ are independently a single bond, —$(CH_2)_2$—, —$CH_2O$—, —$OCH_2$—, —COO— or —OCO—; and
l is 0 or 1.

5. A compound according to claim 4, represented by any one of formulas (1-4-1) to (1-4-6) and formulas (1-5-1) to (1-5-6):

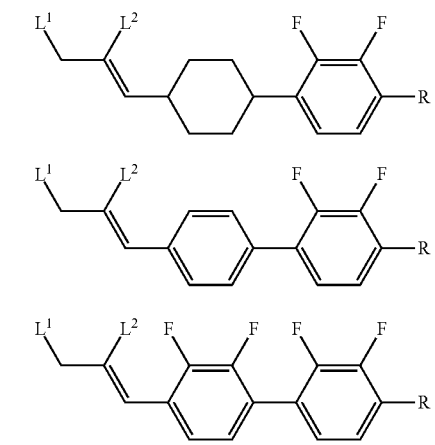
(1-4-1)

(1-4-2)

(1-4-3)

(1-4-4)

(1-4-5)

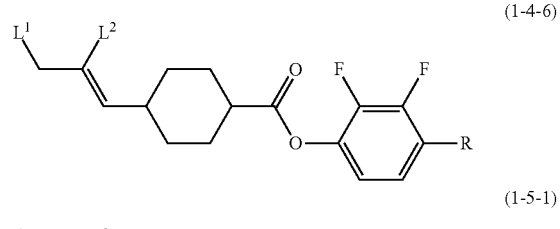
(1-4-6)

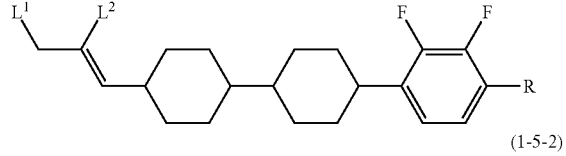
(1-5-1)

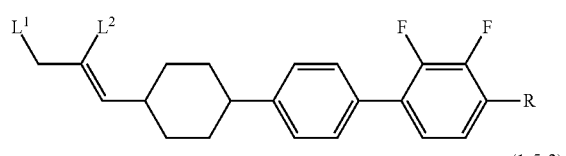
(1-5-2)

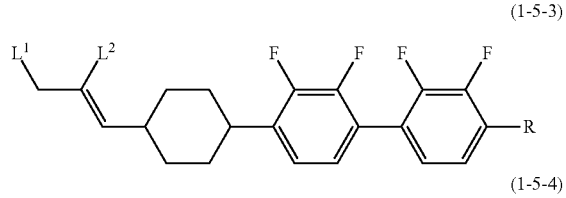
(1-5-3)

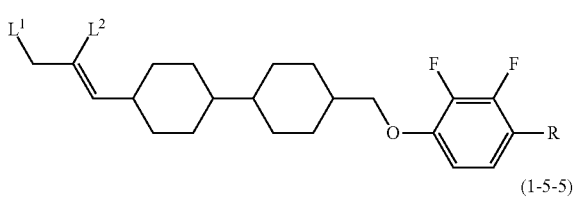
(1-5-4)

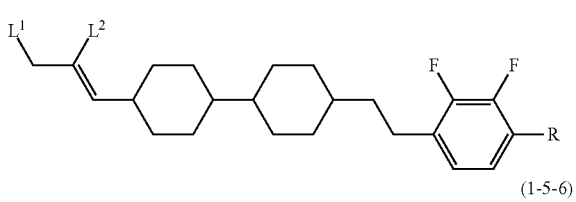
(1-5-5)

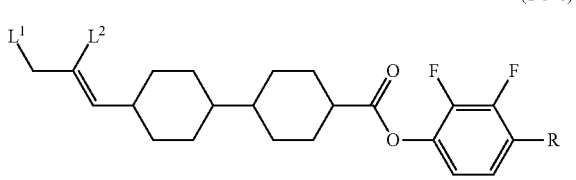
(1-5-6)

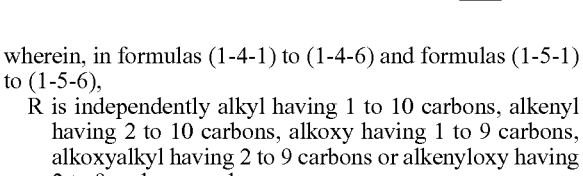

wherein, in formulas (1-4-1) to (1-4-6) and formulas (1-5-1) to (1-5-6),
R is independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; and
$L^1$ and $L^2$ are independently hydrogen or fluorine, and at least one of $L^1$ and $L^2$ is fluorine.

6. A liquid crystal composition comprising at least one of the compounds of claim 1, claim 2, claim 3, claim 4 or claim 5.

7. A liquid crystal composition, containing at least one compound according to claim 1.

8. The liquid crystal composition according to claim 7, further containing at least one compound selected from the group of compounds represented by formulas (2), (3) and (4):

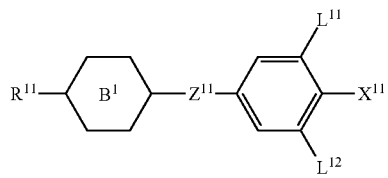
(2)

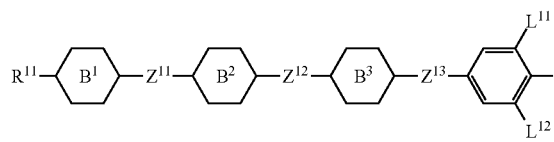
(3)

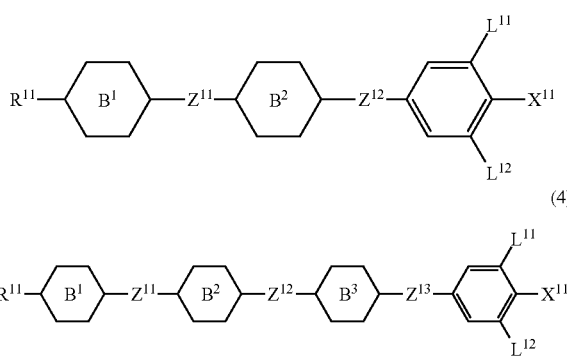
(4)

wherein, in formulas (2) to (4),
R$^{11}$ is alkyl having 1 to 10 carbons or alkenyl having 2 to 10 carbons, and in the alkyl and the alkenyl, at least one of hydrogen may be replaced by fluorine and at least one of —CH$_2$— may be replaced by —O—;
X$^{11}$ is fluorine, chlorine, —OCF$_3$, —OCHF$_2$, —CF$_3$, —CHF$_2$, —CH$_2$F, —OCF$_2$CHF$_2$ or —OCF$_2$CHFCF$_3$;
ring B$^1$, ring B$^2$ and ring B$^3$ are independently 1,4-cyclohexylene, 1,4-phenylene in which at least one of hydrogen may be replaced by fluorine, or tetrahydropyran-2,5-diyl, 1,3-dioxane-2,5-diyl or pyrimidine-2,5-diyl;
Z$^{11}$, Z$^{12}$ and Z$^{13}$ are independently a single bond, —CH$_2$CH$_2$—, —CH═CH—, —C≡C—, —COO—, —CF$_2$O—, —OCF$_2$—, —CH$_2$O— or —(CH$_2$)$_4$—; and L$^{11}$ and L$^{12}$ are independently hydrogen or fluorine, and
in formula (4),
when both of ring B$^1$ and ring B$^2$ are 2,3-difluoro-1,4-phenylene, ring B$^3$ is not 1-pyrane-2,5-diyl, and when both of ring B$^2$ and ring B$^3$ are 2,3-difluoro-1,4-phenylene and Z$^5$ is a single bond, ring B$^1$ is not 1-pyrane-2,5-diyl.

9. The liquid crystal composition according to claim 7, further containing at least one compound selected from the group of compounds represented by formula (5):

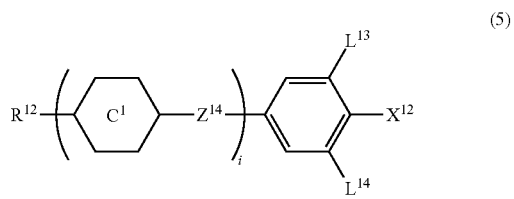
(5)

wherein, in formula (5),
R$^{12}$ is alkyl having 1 to 10 carbons or alkenyl having 2 to 10 carbons, and in the alkyl and the alkenyl, at least one of hydrogen may be replaced by fluorine, and at least one of —CH$_2$— may be replaced by —O—;
X$^{12}$ is —C≡N or —C≡C—C≡N;
ring C$^1$ is 1,4-cyclohexylene, 1,4-phenylene in which at least one of hydrogen may be replaced by fluorine, or tetrahydropyran-2,5-diyl, 1,3-dioxane-2,5-diyl or pyrimidine-2,5-diyl;
Z$^{14}$ is a single bond, —CH$_2$CH$_2$—, —C≡C—, —COO—, —CF$_2$O—, —OCF$_2$— or —CH$_2$O—;
L$^{13}$ and L$^{14}$ are independently hydrogen or fluorine; and
i is 1, 2, 3 or 4.

10. The liquid crystal composition according to claim 7, further containing at least one compound selected from the group of compounds represented by formulas (6) to (12):

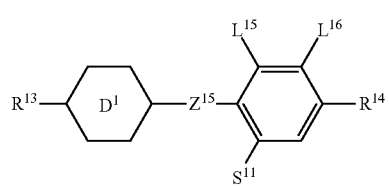
(6)

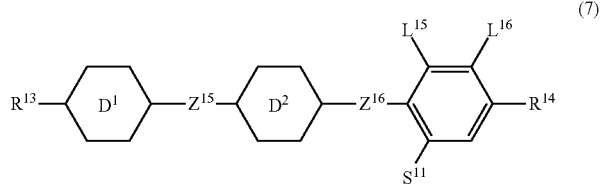
(7)

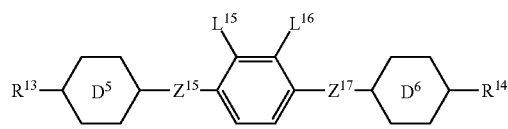
(8)

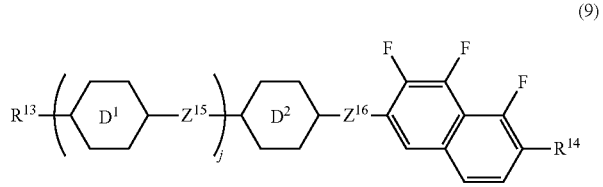
(9)

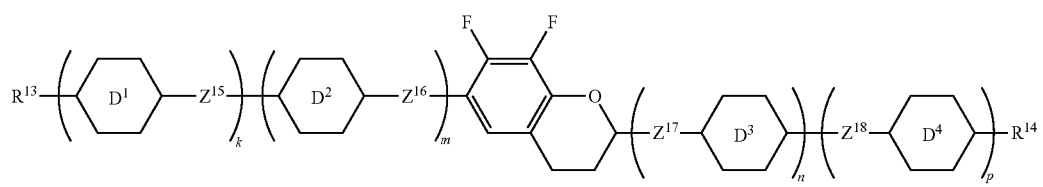

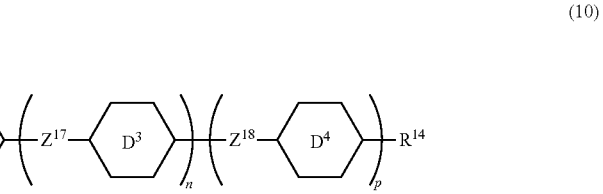
(10)

-continued

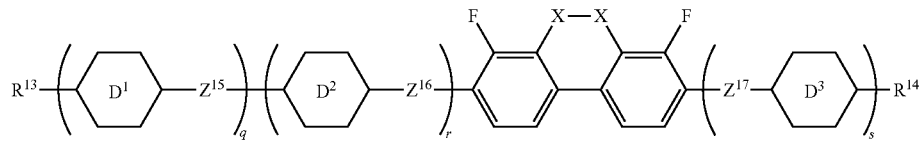
(11)

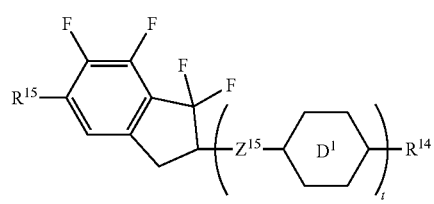
(12)

wherein, in formulas (6) to (12),
- $R^{13}$ and $R^{14}$ are independently alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;
- $R^{15}$ is hydrogen, fluorine, alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;
- $S^{11}$ is hydrogen or methyl;
- X is —O— or —CHF—;
- ring $D^1$, ring $D^2$, ring $D^3$ and ring $D^4$ are independently 1,4-cyclohexylene, 1,4-cyclohexenylene, 1,4-phenylene in which at least one of hydrogen may be replaced by fluorine, or tetrahydropyran-2,5-diyl or decahydronaphthalene-2,6-diyl;
- ring $D^5$ and ring $D^6$ are independently 1,4-cyclohexylene, 1,4-cyclohexenylene, 1,4-phenylene, tetrahydropyran-2,5-diyl or decahydronaphthalene-2,6-diyl;
- $Z^{15}$, $Z^{16}$, $Z^{17}$ and $Z^{18}$ are independently a single bond, —$CH_2CH_2$—, —COO—, —$CH_2O$—, —$OCF_2$— or —$OCF_2CH_2CH_2$—;
- $L^{15}$ and $L^{16}$ are independently fluorine or chlorine;
- j, k, m, n, p, q, r and s are independently 0 or 1, a sum of k, m, n and p is 1 or 2, a sum of q, r and s is 0, 1, 2 or 3, and t is 1, 2 or 3.

11. The liquid crystal composition according to claim 7, further containing at least one compound selected from the group of compounds represented by formulas (13) to (15):

wherein, in formulas (13) to (15),
- $R^{16}$ and $R^{17}$ are independently alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;
- ring $E^1$, ring $E^2$, ring $E^3$ and ring $E^4$ are independently 1,4-cyclohexylene, 1,4-phenylene, 2-fluoro-1,4-phenylene, 2,5-difluoro-1,4-phenylene or pyrimidine-2,5-diyl; and
- $Z^{19}$, $Z^{20}$ and $Z^{21}$ are independently a single bond, —$CH_2CH_2$—, —CH=CH—, —C≡C— or —COO—.

12. The liquid crystal composition according to claim 10, further containing at least one compound selected from the group of compounds represented by formulas (13), (14) and (15) according to claim 11.

13. The liquid crystal composition according to claim 7, further containing at least one optically active compound and/or at least one polymerizable compound.

14. The liquid crystal composition according to claim 7, further containing at least one antioxidant and/or at least one ultraviolet light absorber.

15. A liquid crystal display device, including the liquid crystal composition according to claim 7.

16. A liquid crystal composition, containing at least one compound according to claim 2.

17. A liquid crystal composition, containing at least one compound according to claim 3.

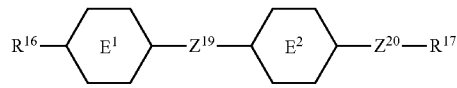
(13)

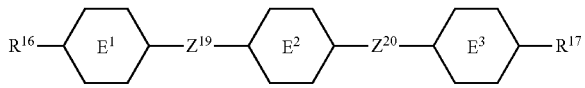
(14)

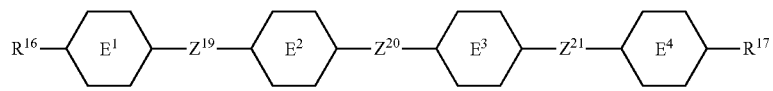
(15)

18. A liquid crystal composition, containing at least one compound according to claim 4.

19. A liquid crystal composition, containing at least one compound according to claim 5.

\* \* \* \* \*